(12) United States Patent
Lam et al.

(10) Patent No.: US 11,369,688 B2
(45) Date of Patent: Jun. 28, 2022

(54) HYBRID TELODENDRIMERS

(71) Applicant: THE REGENTS OF THE UNIVERSITY OF CALIFORNIA, Oakland, CA (US)

(72) Inventors: Kit S. Lam, Davis, CA (US); Yuanpei Li, Elk Grove, CA (US); Gaurav Bharadwaj, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 113 days.

(21) Appl. No.: 16/332,950

(22) PCT Filed: Sep. 15, 2017

(86) PCT No.: PCT/US2017/051862
§ 371 (c)(1),
(2) Date: Mar. 13, 2019

(87) PCT Pub. No.: WO2018/053316
PCT Pub. Date: Mar. 22, 2018

(65) Prior Publication Data
US 2019/0358338 A1    Nov. 28, 2019

Related U.S. Application Data

(60) Provisional application No. 62/395,237, filed on Sep. 15, 2016.

(51) Int. Cl.
| | |
|---|---|
| A61K 47/64 | (2017.01) |
| A61K 47/61 | (2017.01) |
| A61K 47/60 | (2017.01) |
| A61K 9/51 | (2006.01) |
| A61K 47/54 | (2017.01) |
| A61K 31/192 | (2006.01) |
| A61K 31/404 | (2006.01) |
| A61K 31/407 | (2006.01) |
| A61K 31/421 | (2006.01) |
| B82Y 5/00 | (2011.01) |

(52) U.S. Cl.
CPC .......... *A61K 47/641* (2017.08); *A61K 9/5146* (2013.01); *A61K 47/549* (2017.08); *A61K 47/60* (2017.08); *A61K 47/61* (2017.08); *A61K 31/192* (2013.01); *A61K 31/404* (2013.01); *A61K 31/407* (2013.01); *A61K 31/421* (2013.01); *A61K 2123/00* (2013.01); *B82Y 5/00* (2013.01)

(58) Field of Classification Search
CPC .............................. A61K 47/32; A61K 47/641
See application file for complete search history.

(56) References Cited

U.S. PATENT DOCUMENTS

| | | |
|---|---|---|
| 5,459,159 A | 10/1995 | Pandey et al. |
| 6,365,191 B1 | 4/2002 | Burman et al. |
| 6,630,128 B1 | 10/2003 | Love et al. |
| 7,824,709 B2 | 11/2010 | Ryan et al. |
| 8,895,055 B2 | 11/2014 | Lam et al. |
| 9,579,400 B2 * | 2/2017 | Lam .................. A61K 49/0032 |
| 9,642,916 B2 * | 5/2017 | Lam ........................ B82Y 5/00 |
| 10,106,650 B2 * | 10/2018 | Lam ........................ A61P 37/08 |
| 10,238,570 B2 | 3/2019 | Hathaway, III et al. |
| 10,238,750 B2 * | 3/2019 | Lam .................. A61K 41/0071 |
| 10,406,233 B2 * | 9/2019 | Luo ........................ A61K 47/595 |
| 10,556,021 B2 * | 2/2020 | Lam ........................ A61K 47/60 |
| 2002/0041898 A1 | 4/2002 | Unger et al. |
| 2003/0027863 A1 | 2/2003 | Cruz et al. |
| 2003/0073679 A1 | 4/2003 | Mody et al. |
| 2005/0281777 A1 | 12/2005 | Albrecht et al. |
| 2006/0013885 A1 | 1/2006 | Nah et al. |
| 2006/0127310 A1 | 6/2006 | Russell-jones et al. |
| 2008/0188399 A1 | 8/2008 | Sinko et al. |
| 2009/0203706 A1 | 8/2009 | Zhao et al. |
| 2010/0158994 A1 | 6/2010 | Watkin |
| 2011/0286915 A1 * | 11/2011 | Lam ........................ A61P 35/00 424/1.29 |
| 2012/0253191 A1 | 10/2012 | Zheng et al. |
| 2014/0363371 A1 | 12/2014 | Luo et al. |
| 2015/0045419 A1 | 2/2015 | Lam et al. |
| 2015/0056139 A1 | 2/2015 | Luo et al. |
| 2016/0038605 A1 | 2/2016 | Lam et al. |
| 2018/0036417 A1 | 2/2018 | Lam et al. |

FOREIGN PATENT DOCUMENTS

| | | |
|---|---|---|
| EP | 1230934 A1 | 8/2002 |
| EP | 1724295 A1 | 11/2006 |
| EP | 1967212 A2 | 9/2008 |
| EP | 2087912 A1 | 8/2009 |
| EP | 2793953 | 4/2016 |
| EP | 2931920 | 11/2016 |
| JP | 2001146556 A | 5/2001 |
| JP | 2005255810 A | 9/2005 |

(Continued)

OTHER PUBLICATIONS

Xiao et al., "Telodendrimer-based nanocarriers for the treatment of ovarian cancer," Author Manuscript, Published in final edited form as: Ther. Deliv., 4(10), pp. 1279-1292 (2013).
Li et al., "A novel size-tunable nanocarrier system for targeted anticancer drug delivery", Journal of Controlled Release, Jun. 15, 2010, vol. 144, No. 3, pp. 314-323.
International Search Report in PCT/US2017/051862 dated Jan. 11, 2018.
International Search Report and Written Opinion for International Application No. PCT/US2013/074762, dated Apr. 21, 2014.
International Search Report and Written Opinion for PCT/US12/70508, dated Feb. 27, 2013, 11 pages.
International Search Report and Written Opinion for PCT/US2012/037794, dated Jan. 28, 2013, 8 pages.

(Continued)

*Primary Examiner* — Rei Tsang Shiao
(74) *Attorney, Agent, or Firm* — Mintz Levin Cohn Ferris Glovsky and Popeo, P.C.

(57) ABSTRACT

Methods and compositions are provided for hybrid telodendrimers and nanocarriers containing such hybrid telodendrimers.

5 Claims, 28 Drawing Sheets

(56) References Cited

FOREIGN PATENT DOCUMENTS

| | | | |
|---|---|---|---|
| JP | 2012503603 A | 2/2012 | |
| WO | 9959550 A1 | 11/1999 | |
| WO | 2000008467 A2 | 2/2000 | |
| WO | 2007084126 A1 | 7/2007 | |
| WO | 2008062909 A1 | 5/2008 | |
| WO | 2008091246 A1 | 7/2008 | |
| WO | 2008091247 A1 | 7/2008 | |
| WO | 2009123934 A2 | 10/2009 | |
| WO | 2009155335 A2 | 12/2009 | |
| WO | 2010039496 A2 | 4/2010 | |
| WO | 2010148346 A2 | 12/2010 | |
| WO | 2012126115 A1 | 9/2012 | |
| WO | WO 2012/158622 A2 * | 11/2012 | ......... C08G 65/3348 |
| WO | 2013096388 A1 | 6/2013 | |
| WO | 2014093675 A1 | 6/2014 | |
| WO | 2016172635 A1 | 10/2016 | |
| WO | 2018136778 A1 | 7/2018 | |
| WO | 2019051121 A1 | 3/2019 | |

OTHER PUBLICATIONS

International Search Report dated May 6, 2010, issued in related International Patent Application No. PCT/US2009/057852, 19 pages.
Chapman et al. (1994) "Hydraamphiphiles: Novel Linear Dendritic Block Copolymer Surfactants", J. Am. Chem. Soc., 116:11195-11196.
Chen et al. (Feb. 23, 2008) "Fluorescence Study of Inclusion Complexes between Star-Shaped Cholic Acid Derivatives and Polycyclic Aromatic Fluorescent Probes and the Size Effects of Host and Guest Molecule", The Journal of Physical Chemistry B, 112(11):3402-3409.
Choi et al. (1999) "Poly(ethylene glycol)-block-poly(L-lysine) Dendrimer: Novel Linear Polymer/Dendrimer Block Copolymer Forming a Spherical Water-Soluble Polyionic Complex with DNA", Bioconjugate Chem., 10:62-65.
Duncan et al. (May 2003) "The Dawning Era of Polymer Therapeutics", Nature Reviews Drug Discovery, 2(5):347-360.
Giuntini et al. (2011) "Synthetic Approaches for the Conjugation of Porphyrins and Related Macrocycles to Peptides and Proteins", Photochemical & Photobiological Sciences, 10(5):759-791.
Gref et al. (Mar. 18, 1994) "Biodegradable Long-Circulating Polymeric Nanospheres", Science, 263(5153):1600-1603.
Gu et al. (Dec. 21, 2007) "pH-Triggered Reversible "Stealth" Polycationic Micelles", Biomacromolecules, 9(1):255-262.

Heffernan et al. (Oct. 2009) "Disulfide-Crosslinked Polyion Micelles for Delivery of Protein Therapeutics", Annals of Biomedical Engineering volume 37(10):1993-2002.
Huh et al. (Jan. 3, 2005) "Hydrotropic Polymer Micelle System for Delivery of Paclitaxel", Journal of Controlled Release, 101(1-3):59-68.
Kaminskas et al. (Dec. 3, 2009) "PEGylation of Polylysine Dendrimers Improves Absorption and Lymphatic Targeting Following SC Administration in Rats", Journal of Controlled Release, 140(2):108-116.
Kaminskas et al. (Apr. 5, 2008) "The Impact of Molecular Weight and PEG Chain Length on the Systemic Pharmacokinetics of PEGylated Poly L-lysine Dendrimers", Molecular Pharmaceutics, , 5(3):449-463.
Li et al. (Jun. 1999) "Antimicrobial Activities of Amine- and Guanidine-Functionalized Cholic Acid Derivatives", Antimicrobial Agents and Chemotherapy, 43(6):1347-1349.
Li et al. (Nov. 2007) "Dendrimer Generation Effects on Photodynamic Efficacy of Dendrimer Porphyrins and Dendrimer-Loaded Supramolecular Nanocarriers", Chemistry of Materials, 19(23):5557-5562.
Li et al. (2012) "Well-Defined, Reversible Boronate Crosslinked Nanocarriers for Targeted Drug Delivery in Response to Acidic Ph Values and Cis-Diols.", Angewandte Chemie, 51(12):2864-2869.
LI et al. (Jan. 17, 2012) "Well-Defined, Reversible Boronate Crosslinked Nanocarriers for Targeted Drug Delivery in Response to Acidic pH Values and cis-Diols", Angewandte Chemie, 124(12):2918-2923.
Li et al. (Sep. 2011) "Well-defined, Reversible Disulfide Crosslinked Micelles for On-demand Paclitaxel Delivery", Biomaterials, 32(27):6633-6645.
Luo et al. (2009) "Asymmetric Poly(ethylene glycol) Star Polymers with a Cholic Acid Core and Their Aggregation Properties", Biomacromolecules, 10(4):900-906.
Luo et al. (Jul. 21, 2010) "Well-defined, Size-tunable, Multifunctional Micelles for Efficient Paclitaxel Delivery for Cancer Treatment", Bioconjugate Chemistry, 21(7):1216-1224.
Vijayalakshmi et al. (Jun. 23, 2005) "A Simple Construction of a Bile Acid Based Dendritic Light Harvesting System", 7(13):2727-2730.
Xiao et al. (Oct. 2009) "A Self-assembling Nanoparticle for Paclitaxel Delivery in Ovarian Cancer", Biomaterials, 30(30):6006-6016.
Xiao et al. (Oct. 30, 2011) "PEG-oligocholic Acid Telodendrimer Micelles for the Targeted Delivery of Doxorubicin to B-cell Lymphoma", Journal of Controlled Release, 155(2):272-281.

* cited by examiner

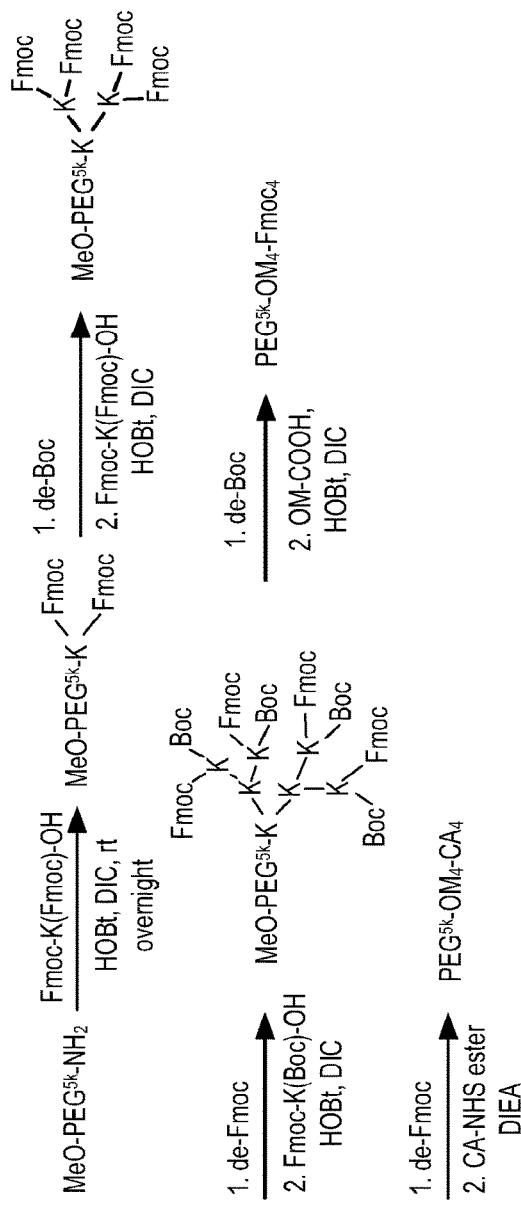
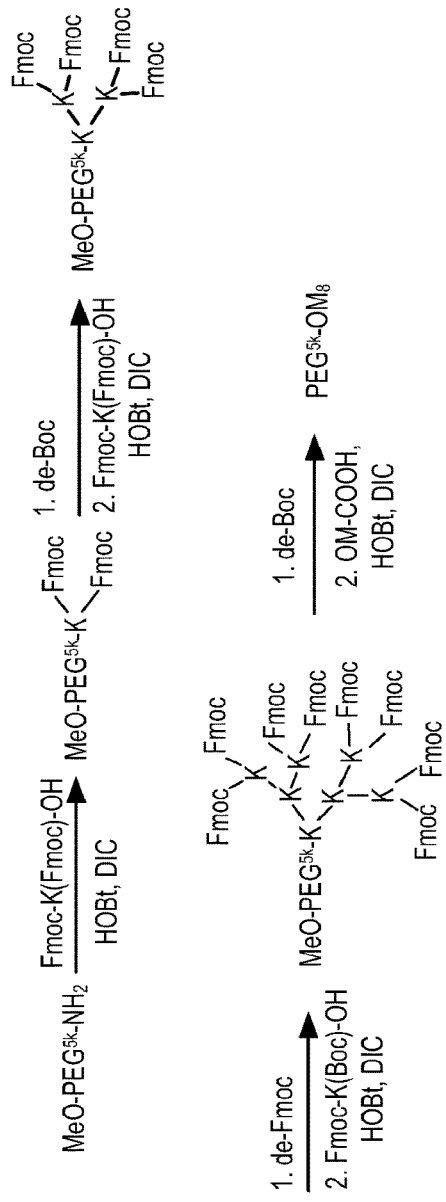

Fig. 11
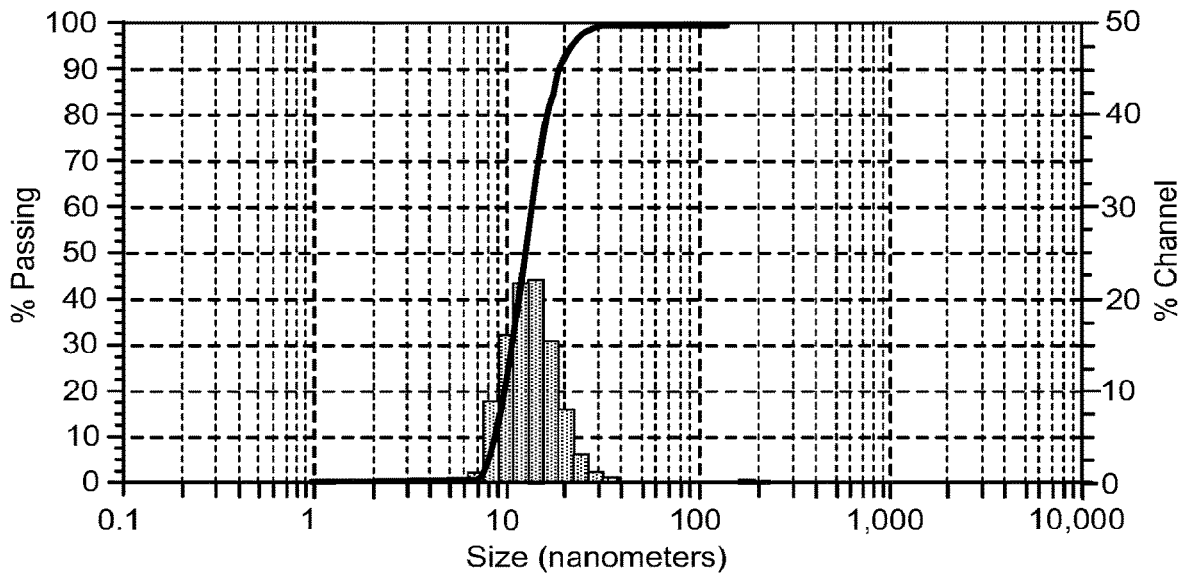
PEG$^{5K}$-(Cinnamic acid)$_4$/CA$_4$ with docetaxel
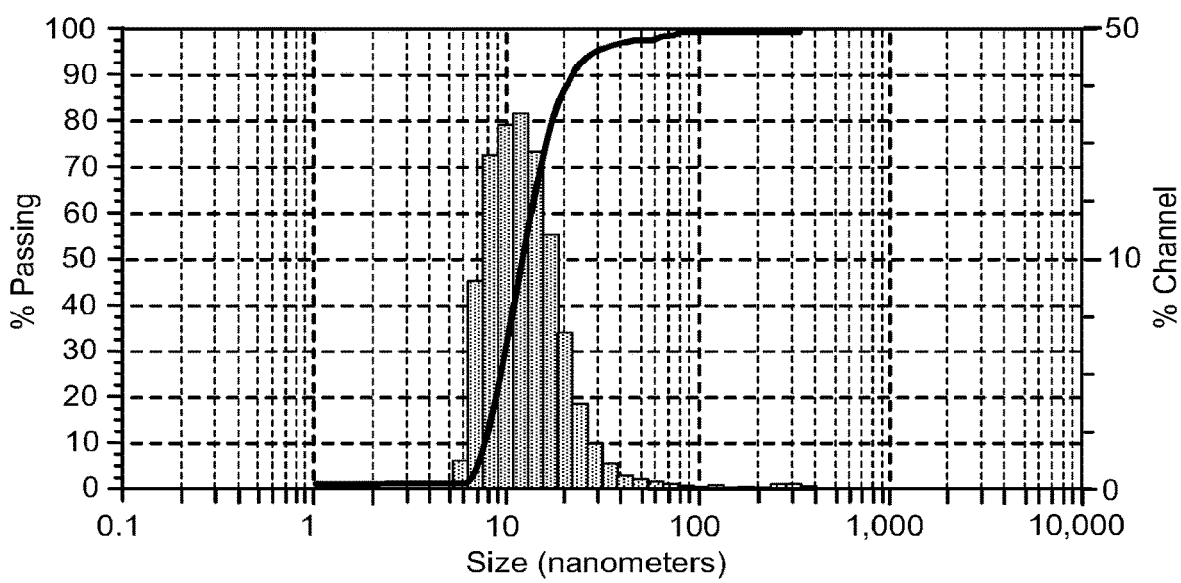
PEG$^{5K}$-(Lipoic acid)$_4$/CA$_4$ with docetaxel

Fig. 11 (Continued)
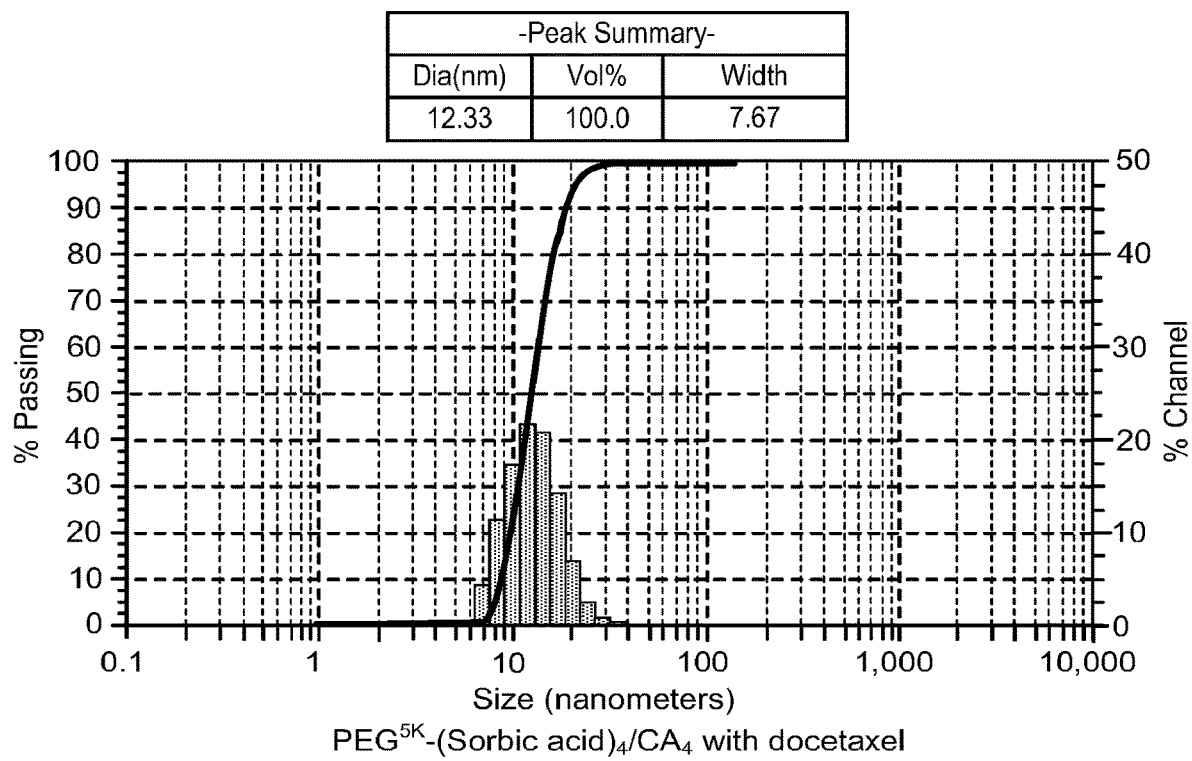
$PEG^{5K}$-(Sorbic acid)$_4$/CA$_4$ with docetaxel
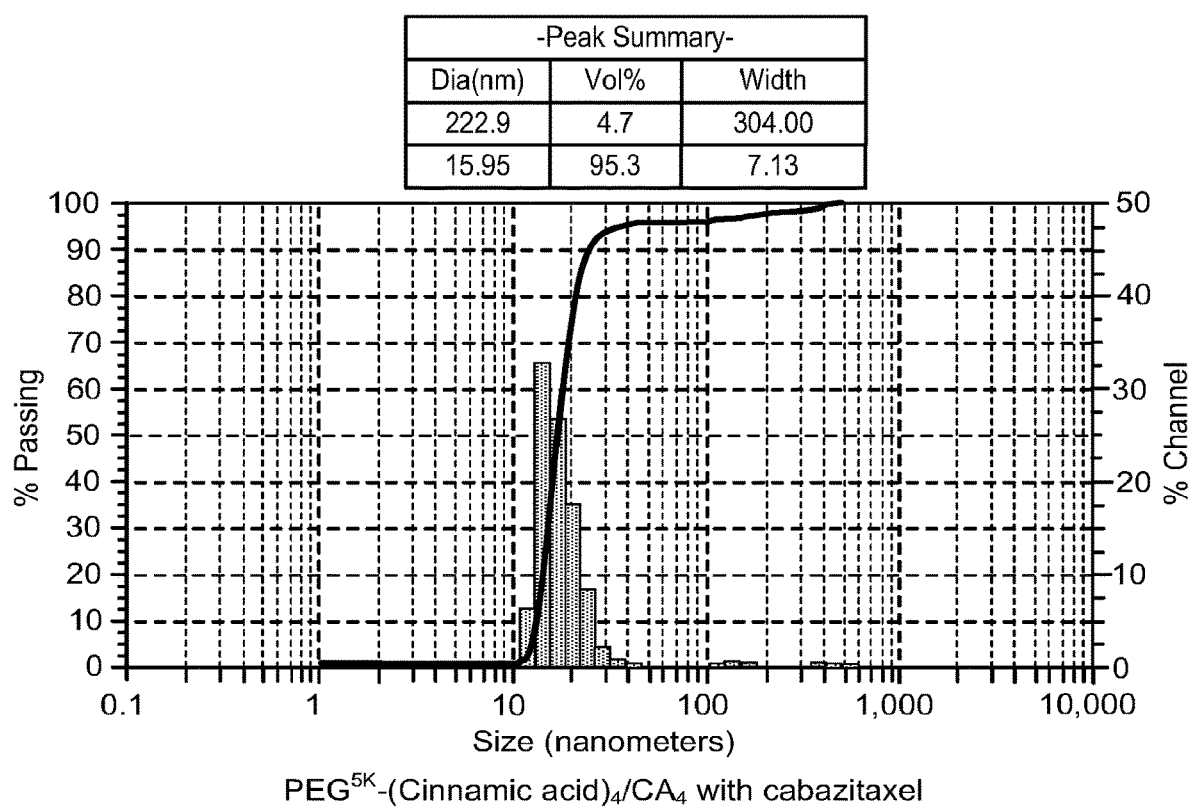
$PEG^{5K}$-(Cinnamic acid)$_4$/CA$_4$ with cabazitaxel PEG$^{5K}$-(Linoleic acid)$_4$/CA$_4$ with cabazitaxel PEG$^{5K}$-Succ$_4$-OM$_4$/CA$_4$ ○ Lysine
● Succinic acid
▨ Hydroxyl/NH$_2$ containing organic moiety
■ Cholic acid PEG$^{5K}$-OM$_4$/Cys4-Ebes4-CA$_4$ ○ Lysine
● Cysteine
● Linkers such as Ebes
▨ Organic moiety
■ Cholic acid PEG$^{5K}$-(Lipoic acid)$_4$/CA$_4$ Cross linked
PEG$^{5K}$-(Lipoic acid)$_4$/CA$_4$ PEG$^{5K}$-OM$_4$/Cys$_4$-CA$_4$ ○ Lysine ▨ Cysteine or N-acetyl Cysteine ■ Cholic acid ⬬ Aminocaproic acid,
5-aminopentanoic acid,
4-aminobutanoic acid or
β-Alanine

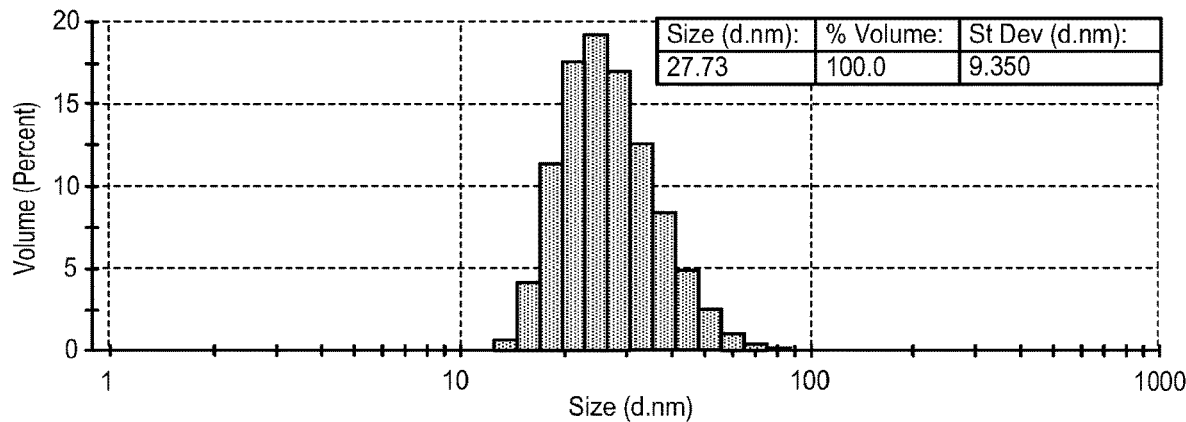
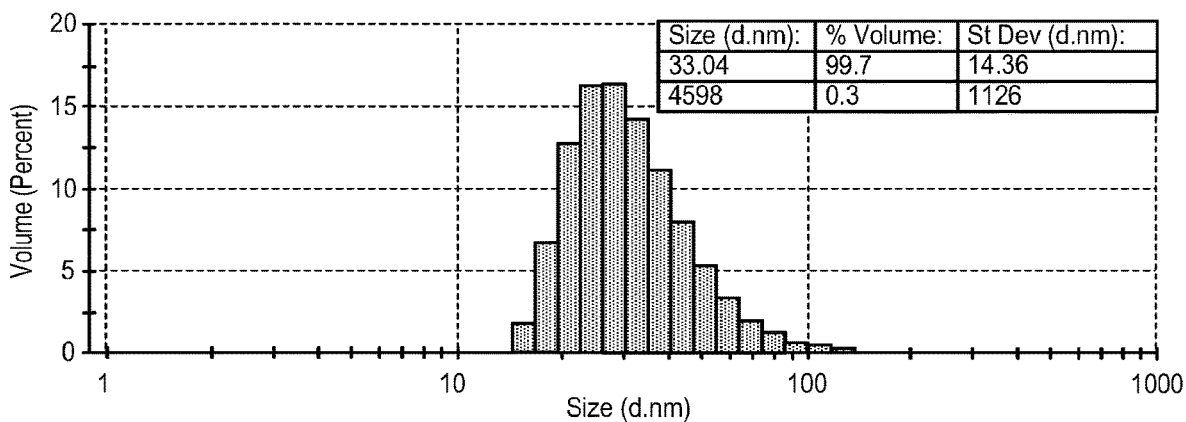
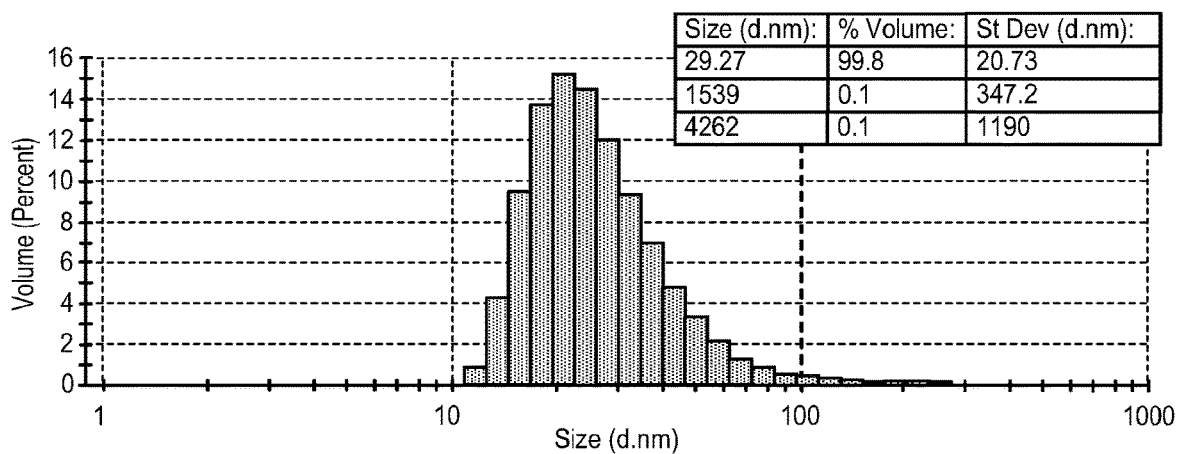

Size Distribution by Volume

Size Distribution by Volume

Size Distribution by Volume

Size Distribution by Volume

Size Distribution by Volume

HYBRID TELODENDRIMERS

CROSS-REFERENCE TO RELATED APPLICATIONS

This application is the U.S. National Stage Entry under § 371 of International Application No. PCT/US2017/051862, filed Sep. 15, 2017, which claims priority to U.S. Provisional Application No. 62/395,237, filed Sep. 15, 2016, each which is incorporated herein it its entirety for all purposes.

GOVERNMENT LICENSE RIGHTS

This invention was made with government support under Contract Nos. 2R01CA115483-08 and 1U01CA198880-01 awarded by the National Institutes of Health. The government has certain rights in the invention.

BACKGROUND OF THE INVENTION

Methods and compositions for delivery of small molecule drugs through a subject and to a targeted location is an important area of research. Taxane is a benchmark class of small molecule anti-cancer agent that works by interfering with normal microtubule breakdown during cell division. Currently three members of taxane family viz. paclitaxel (PTX), docetaxel (DTX), and cabazitaxel (CTX) have been approved by Federal Drug Administration for clinical use (FIG. 1), with the first two being widely prescribed as front line treatment options for many forms of cancers such as breast, ovarian and lung cancer. CTX is the latest member of taxane family that has been approved for the treatment of hormone refractory prostate cancer. Despite their widespread popularity, all three taxanes show very low solubility in water thereby making development of effective formulation for medicinal use challenging. They are either formulated in a mixture of Cremophor EL/absolute ethanol or in Polysorbate 80, both of which are associated with serious side effects (hypersensitivity reactions, peripheral neurotoxicity, etc). Application of nanomedicine in cancer field has led to the development and FDA approval of PTX loaded human serum albumin nano-aggregates (Abraxane®). Although more drug can be given (240 mg/m² PTX for Abraxane vs 175 mg/m² PTX for paclitaxel), these nanoparticles are relatively "large" (130 nm in diameter), and improvement in clinical efficacy is only marginal. A wide variety of PTX and DTX nanoformulations have been explored and more recently CTX nanoformulations have been attempted. However, to the best of our knowledge, there is not a single polymer or a nano-platform that can stably encapsulate all the members of taxane family with a high loading efficiency. The present invention meets this and other needs.

BRIEF SUMMARY OF THE INVENTION

In one embodiment, the present invention provides a compound of formula III:

$$(PEG)_m\text{-}A_p\text{-}L\text{-}D(Y^1)_q\text{---}(R)_n \quad (III)$$

wherein A is linked to at least one PEG group; D is a dendritic polymer having a single focal point group, a plurality of branched monomer units X, a plurality of crosslinkable groups $Y^1$, and a plurality of end groups R; L is a bond or a linker linked to the focal point group of the dendritic polymer; each PEG is a polyethyleneglycol (PEG) polymer, wherein each PEG polymer has a molecular weight of 1-50 kDa; each R is independently selected from R' and R", wherein each R' is independently an amphiphilic compound having a hydrophobic face and a hydrophilic face, and each R" is independently selected from the group consisting of a saturated or unsaturated fatty acid, a saturated or unsaturated carboxylic acid, a vitamin or metabolite thereof, an enzyme co-factor, an antibiotic, and a drug, wherein each R has a molecular weight of greater than 100 g/mol and less than 2000 g/mol; subscript n is an integer from 8 to 20, wherein subscript n is equal to the number of end groups on the dendritic polymer; each $Y^1$ is independently a crosslinkable group selected from the group consisting of a thiol, a boronic acid, a 1,2-diol, or a cysteine group; subscript m is an integer from 0 to 5; and; each of subscripts p and q are 0 or from 2 to 10.

In another embodiment, the present invention provides a compound of formula I:

$$(PEG)m\text{-}L\text{-}D\text{-}(R)n \quad (I),$$

wherein D is a dendritic polymer having a single focal point group, a plurality of branched monomer units X and a plurality of end groups R; L is a bond or a linker linked to the focal point group of the dendritic polymer; each PEG is a polyethyleneglycol (PEG) polymer, wherein each PEG polymer has a molecular weight of 1-50 kDa; each R is independently linked to a monomer X of the dendritic polymer directly or via a linker L'; each R is independently selected from R' and R", wherein R' is an amphiphilic compound having a hydrophobic face and a hydrophilic face, and R" is a saturated or unsaturated fatty acid, a saturated or unsaturated carboxylic acid, a vitamin or metabolite thereof, an enzyme co-factor, an antibiotic, or a drug; subscript n is an integer from 8 to 20, wherein subscript n is equal to the number of end groups on the dendritic polymer, and wherein at least one-fourth of the number n of R groups are R'; and subscript m is an integer from 0 to 5. In some embodiments, each R has a molecular weight of greater than 100 g/mol and less than 2000 g/mol.

In another embodiment, the present invention provides a compound of formula II:

$$(PEG)_m\text{-}A_p\text{-}L\text{-}D(Y^1)_q\text{---}(R)_n \quad (II),$$

wherein A is linked to at least one PEG group; D is a dendritic polymer having a single focal point group, a plurality of branched monomer units X and a plurality of end groups; L is a bond or a linker linked to the focal point group of the dendritic polymer; each PEG is a polyethyleneglycol (PEG) polymer, wherein each PEG polymer has a molecular weight of 1-50 kDa; each R is independently selected from R' and R", wherein each R' is independently an amphiphilic compound having a hydrophobic face and a hydrophilic face, and each R" is independently selected from the group consisting of a saturated or unsaturated fatty acid, a saturated or unsaturated carboxylic acid, a vitamin or metabolite thereof, an enzyme co-factor, an antibiotic, and a drug; subscript n is an integer from 8 to 20, wherein subscript n is equal to the number of end groups on the dendritic polymer, and wherein at least one-fourth of the number n of R groups are R'; each $Y^1$ is independently a crosslinkable group selected from the group consisting of a thiol, a boronic acid, a 1,2-diol, or a cysteine group; subscript m is an integer from 0 to 5; and each of subscripts p and q are 0 or from 2 to 10, such that one of subscripts p and q is from 2 to 10. In some embodiments, each R has a molecular weight of greater than 100 g/mol and less than 2000 g/mol.

In another embodiment, the present invention provides a compound of the following formula:

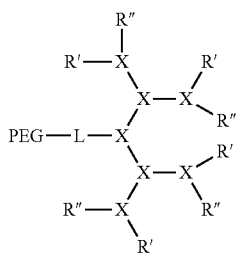

wherein X is a branched monomer unit; L is a bond or a linker; each PEG is a polyethyleneglycol (PEG) polymer, wherein each PEG polymer has a molecular weight of 1-50 kDa; each R' is independently an amphiphilic compound having a hydrophobic face and a hydrophilic face and each R' is independently linked to a different branched monomer unit X via a bond or a linker; and each R" is independently a crossslinkable group selected from the group consisting of a thiol, a cysteine, and an N-acetyl cysteine, wherein the crosslinkable groups are each independently linked to a different branched monomer unit X via a bond or a linker. In some embodiments, each R has a molecular weight of greater than 100 g/mol and less than 2000 g/mol.

The present invention also provides a nanocarrier comprising at least one, or at least two of the foregoing conjugates. In some embodiments, at least two conjugates of the nanocarrier comprise a crosslinkable group, wherein the crosslinkable groups of one conjugate are crosslinked to the crosslinkable groups of another conjugate. The present invention also provides drug loaded nanocarriers.

The present invention also provides methods for preparing any one or more of the foregoing compounds, or nanocarriers, including nanocarriers loaded with drug or imaging agent. The present invention also provides methods of administering any one or more of the foregoing compounds, or nanocarriers, including nanocarriers loaded with drug or imaging agent.

BRIEF DESCRIPTION OF THE DRAWINGS

FIG. 5A-B illustrates (A) a synthetic scheme for generating hybrid telodendrimers; and (B) a synthetic scheme for generating non-hybrid telodendrimers.

FIG. 23 illustrates the size distribution by volume for nanocarriers prepared using PEG$^{5K}$-(Etodolac)$_4$/(CA)$_4$.

FIG. 24 illustrates the size distribution by volume for nanocarriers prepared using PEG$^{5K}$-(Indomethacin)$_4$/(CA)$_4$.

FIG. 25 illustrates the size distribution by volume for nanocarriers prepared using PEG$^{5K}$-(Naproxen)$_4$/(CA)$_4$.

FIGS. 43A, 43B and 43C illustrate the results for an in vivo therapeutic study for an MB49 tumor using PEG$^{5K}$-(Ahx-(NAc-Cys))$_4$/CA$_4$ and PEG$^{5K}$-(Ahx-(NAc-Cys))$_4$/CA$_4$ loaded with vinblastine, and show tumor growth (FIG. 43A), survival curve (FIG. 43B) and body weight (FIG. 43C).

DETAILED DESCRIPTION OF THE INVENTION

I. General

Figure 1:
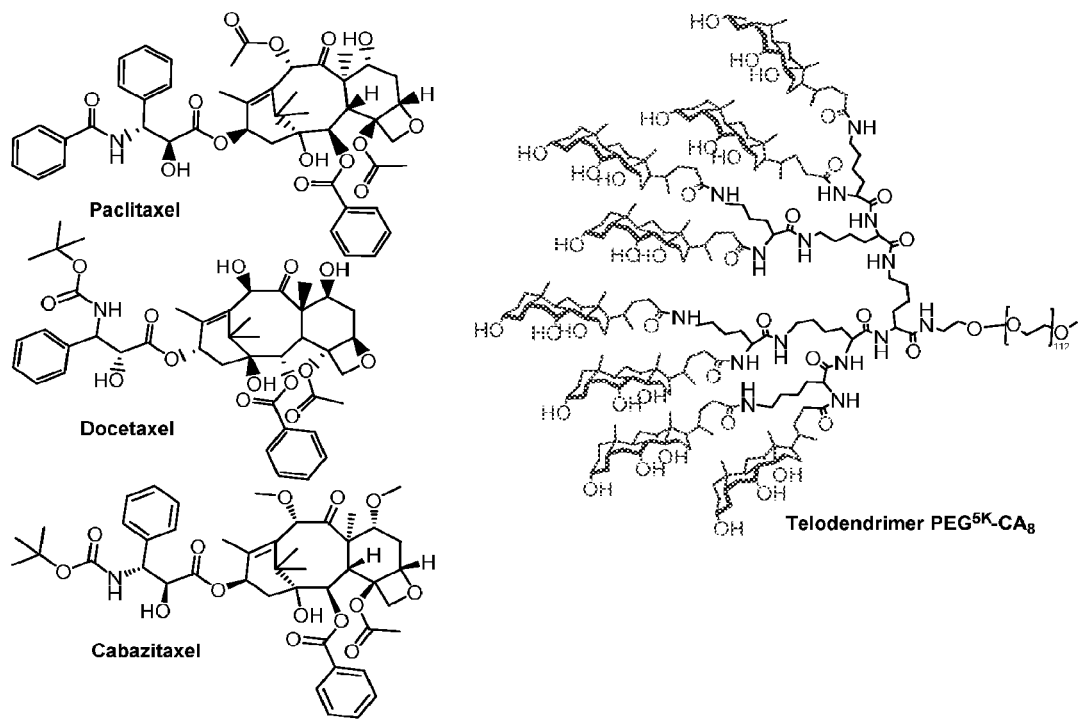
FIG. 1 illustrates chemical structures of FDA approved taxane drugs (left) and PEG$^{5k}$-CA$_8$ telodendrimer.

The present invention provides improved hybrid and non-hybrid and crosslinkable hybrid and non-hybrid telodendrimer conjugates having a hydrophilic poly(ethylene glycol) (PEG) segment, a dendrimer segment, and a plurality of end groups R. The PEG segment can have a branched or linear architecture including one or more PEG chains. At least a portion of (e.g., ¼, ⅓, ½, ⅔, ¾, or all) the end groups R can be cholic acid or a derivative thereof. The remaining end groups are organic moieties (OMs). The cholic acid or derivatives thereof and the PEG are connected by oligomers a dendrimer that can contain a variety of acid repeat units. Typically, the dendrimer comprises a diamino carboxylic acid, lysine. The telodendrimers can also be functionalized with a crosslinkable group. The telodendrimers can aggregate in solution to form micelles with a hydrophobic interior and a hydrophilic exterior, and can be used as nanocarriers to deliver drugs (e.g., taxanes) or other agents (e.g., imaging agents) having low water solubility. Following micelle formation, telodendrimers having crosslinkable groups can be crosslinked using the crosslinkable groups, forming a more stable micelle.

II. Definitions

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendrimer can be attached to other segments of the compounds of the invention, and the end groups may be further functionalized with additional chemical moieties.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and organic moieties. Different moieties may be selectively installed at a desired end group using orthogonal protecting group strategies.

As used herein, the term "nanocarrier" refers to a micelle resulting from aggregation of the dendrimer conjugates of the invention. The nanocarrier has a hydrophobic core and a hydrophilic exterior.

As used herein, the terms "monomer" and "monomer unit" refer to a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl) butyric acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as D-amino acids and other non-naturally occurring amino acids.

As used herein, the term "oligomer" refers to five or fewer monomers, as described above, covalently linked together. The monomers may be linked together in a linear or branched fashion. The oligomer may function as a focal point for a branched segment of a telodendrimer.

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives As used herein, the term "cholic acid" refers to (R)-4-((3R, 5S, 7R, 8R, 9S, 10S, 12S, 13R, 14S, 17R)-3, 7, 12-trihydroxy-10, 13-dimethylhexadecahydrp-1H-cyclopenta[a]phenanthren-1 7-yl)pentanoic acid. Cholic acid is also known as 3α,7α, 12α-trihydroxy-5P-cholanoic acid;

3-a,7-a, 12-a-Trihydroxy-5-cholan-24-oic acid; 17-β-(1-methyl-3-carboxypropyl)etiocholane-3 a,7 a, 12 a-triol; cholalic acid; and cholalin. Cholic acid derivatives and analogs, such as allocholic acid, pythocholic acid, avicholic acid, deoxycholic acid, chenodeoxycholic acid, are also useful in the present invention. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present invention include, but are not limited to, a taxane (e.g., paclitaxel, docetaxel, cabazitaxel, Baccatin III, 10-deacetylbaccatin, Hongdoushan A, Hongdoushan B, or Hongdoushan C), doxorubicin, etoposide, irinotecan, SN-38, cyclosporin A, podophyllotoxin, Carmustine, Amphotericin, Ixabepilone, Patupilone (epothelone class), rapamycin and platinum drugs. Other drugs includes nonsteroidal anti-inflammatory drugs, and vinca alkaloids such as vinblastine and vincristine. The drugs of the present invention also include prodrug forms. One of skill in the art will appreciate that other drugs are useful in the present invention.

As used herein, the term "crosslinkable group" or "crosslinking group" refers to a functional group capable of binding to a similar or complementary group on another molecule, for example, a first crosslinkable group on a first dendritic polymer linking to a second crosslinkable group on a second dendritic polymer. Groups suitable as crosslinkable and crosslinking groups in the present invention when incorporated into the interior of a dendrimer include thiols such as cysteine, boronic acids and 1,2-diols including 1,2-dihydroxybenzenes such as catechol. Groups suitable as crosslinkable and crosslinking groups in the present invention when incorporated at one or more end groups of a dendrimer include thiols such as cysteine and N-acetyl-cysteine. When the crosslinkable and crosslinking groups combine, they form cross-linked bonds such as disulfides and boronic esters. Other crosslinkable and crosslinking groups are suitable in the present invention.

As used herein, the term "bond cleavage component" refers to an agent capable of cleaving the cross-linked bonds formed using the crosslinkable and crosslinking groups of the present invention. The bond cleavage component can be a reducing agent, such as glutathione, when the cross-linked bond is a disulfide, or mannitol when the cross-linked bond is formed from a boronic acid and 1,2-diol.

As used herein, the term "imaging agent" refers to chemicals that allow body organs, tissue or systems to be imaged. Exemplary imaging agents include paramagnetic agents, optical probes, and radionuclides.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "organic moiety," "OM," and the like refers to an end group that is not a cholic acid or derivative thereof, and is selected from the group consisting of a saturated or unsaturated fatty acid, a saturated or unsaturated carboxylic acid, a vitamin or metabolite thereof, an enzyme co-factor, an antibiotic, and a drug. The organic moieties end groups of the present invention generally have a molecular weight between 100 and 2000 g/mol, preferably between 130 and 500 g/mol.

III. Hybrid Telodendrimers

The present invention provides improved hybrid and non-hybrid and crosslinkable hybrid and non-hybrid telodendrimer conjugates having a hydrophilic poly(ethylene glycol) (PEG) segment, a dendrimer segment, and a plurality of end groups R. The PEG segment can have a branched or linear architecture including one or more PEG chains. At least a portion of (e.g., ¼, ⅓, ½, ⅔, ¾, or all) the end groups R can be cholic acid or a derivative thereof. The remaining end groups are organic moieties (OMs). The cholic acid or derivatives thereof and the PEG are connected by oligomers a dendrimer that can contain a variety of acid repeat units. Typically, the dendrimer comprises a diamino carboxylic acid, lysine. The telodendrimers can also be functionalized with a crosslinkable group. The telodendrimers can aggregate in solution to form micelles with a hydrophobic interior and a hydrophilic exterior, and can be used as nanocarriers to deliver drugs (e.g., taxanes) or other agents (e.g., imaging agents) having low water solubility. Following micelle formation, telodendrimers having crosslinkable groups can be crosslinked using the crosslinkable groups, forming a more stable micelle.

In some embodiments, the present invention provides a compound of formula III:

$$(PEG)_m\text{-}A_p\text{-}L\text{-}D(Y^1)_q\text{—}(R)_n \qquad \text{(III)}$$

wherein A is linked to at least one PEG group; D is a dendritic polymer having a single focal point group, a plurality of branched monomer units X, a plurality of crosslinkable groups $Y^1$, and a plurality of end groups R; L is a bond or a linker linked to the focal point group of the dendritic polymer; each PEG is a polyethyleneglycol (PEG) polymer, wherein each PEG polymer has a molecular weight of 1-50 kDa; each R is independently selected from R' and R", wherein each R' is independently an amphiphilic compound having a hydrophobic face and a hydrophilic face, and each R" is independently selected from the group consisting of a saturated or unsaturated fatty acid, a saturated or unsaturated carboxylic acid, a vitamin or metabolite thereof, an enzyme co-factor, an antibiotic, and a drug, wherein each R has a molecular weight of greater than 100 g/mol and less than 2000 g/mol; subscript n is an integer from 8 to 20, wherein subscript n is equal to the number of end groups on the dendritic polymer; each $Y^1$ is independently a crosslinkable group selected from the group consisting of a thiol, a boronic acid, a 1,2-diol, or a cysteine group; subscript m is an integer from 0 to 5; and each of subscripts p and q are 0 or from 2 to 10.

In some embodiments, the present invention provides a compound of formula IIIa:

$$(PEG)_m\text{-L-D}(Y^1)_q\text{—}(R)_n \qquad (IIIa).$$

In some embodiments, the compound has the following structure:

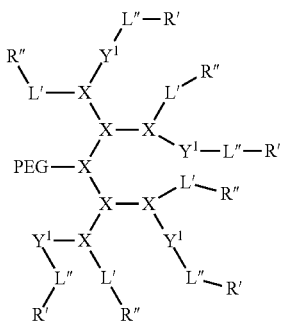

wherein each L' and L" is independently a bond or a linker Ebes, aminocaproic acid, 5-aminopentanoic acid, 4-aminobutanoic acid, β-alanine, or succinic acid; PEG has a molecular weight of 1-50 kDa; each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH$_2$); each R" is independently selected from the group consisting of a saturated or unsaturated fatty acid, a saturated or unsaturated carboxylic acid, a vitamin or metabolite thereof, an enzyme co-factor, an antibiotic, and a drug; each branched monomer unit X is lysine; and each $Y^1$ is absent or a thiol, boronic acid, a 1,2-diol, or a cysteine.

In some embodiments, each L' is independently a bond or aminocaproic acid, 5-aminopentanoic acid, 4-aminobutanoic acid, β-alanine, or succinic acid; each L" is independently a bond or a linker Ebes; PEG has a molecular weight of 1-50 kDa; each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH$_2$); each R" is independently selected from the group consisting of a saturated or unsaturated fatty acid, a saturated or unsaturated carboxylic acid, a vitamin or metabolite thereof, an enzyme co-factor, an antibiotic, and a drug; each branched monomer unit X is lysine; and each $Y^1$ is absent a thiol, boronic acid, a 1,2-diol, or a cysteine.

In some embodiments, L' is a bond and L" is a bond. In some embodiments, L' is a bond and L" is Ebes. In some embodiments, L' is aminocaproic acid, 5-aminopentanoic acid, 4-aminobutanoic acid, β-alanine, or succinic acid, and L" is a bond. In some embodiments, L' is succinic acid and L" is a bond. In some embodiments, L' is aminocaproic acid, 5-aminopentanoic acid, 4-aminobutanoic acid, β-alanine, or succinic acid, and L" is Ebes. In some embodiments, L' is succinic acid and L" is Ebes.

In some embodiments, each $Y^1$ is a bond. In some embodiments, each $Y^1$ is a thiol, boronic acid, a 1,2-diol, or a cysteine. In some embodiments, each $Y^1$ is cysteine.

In some embodiments, each L" is a bond and each $Y^1$ is a bond. In some embodiments, each L" is a Ebes and each $Y^1$ is a bond. In some embodiments, each L" is a bond and each $Y^1$ is cysteine. In some embodiments, each L" is Ebes and each $Y^1$ is cysteine.

In some embodiments, each L' is a bond, each L" is a bond, and each $Y^1$ is a bond. In some embodiments, each L' is succinic acid, each L" is a bond, and each $Y^1$ is a bond. In some embodiments, each L' is a bond, each L" is Ebes, and each $Y^1$ is cysteine. In some embodiments, each L' is succinic acid, each L" is Ebes, and each $Y^1$ is cysteine.

In each embodiment of the present invention, each R' can be Cholic acid, CA-4OH, CA-5OH, or CA-3OH—NH$_2$; and each R" can be selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, aminocaproic acid, riboflavin, pyridoxine, and cholecalciferol.

In each embodiment of the present invention, R' can be cholic acid.

In some embodiments, the compound has the structure:

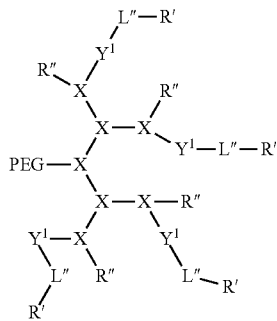

wherein each L" is independently a bond or a linker Ebes; PEG has a molecular weight of 1-50 kDa; each R' is cholic acid; each R" is selected from the group consisting of cinnamic acid and linoleic acid; each branched monomer unit X is lysine; and each $Y^1$ is cysteine.

A. Organic Moiety Hybrids

The present invention provides a PEGylated dendrimer, referred to as a telodendrimer, containing cholic acid groups and other organic moieties (OMs) at the dendrimer periphery. In some embodiments, the invention provides a compound of formula I:

$$(PEG)_m\text{-L-D-}(R)_n \qquad (I)$$

wherein radical D of formula I is a dendritic polymer having a single focal point group, a plurality of branched monomer units X and a plurality of end groups R. Radical L of formula l is a bond or a linker linked to the focal point group of the dendritic polymer. Each PEG of formula I is a polyethyleneglycol (PEG) polymer, wherein each PEG polymer has a molecular weight of 1-50 kDa. Each R of formula I has a molecular weight of greater than 100 g/mol and less than 2000 g/mol. Each R is also independently linked to a monomer X of the dendritic polymer either directly via a bond, or indirectly via a linker L'. Each R is also independently selected from an end group R' and an end group R", wherein each R' is independently an amphiphilic compound having a hydrophobic face and a hydrophilic face, and each R" is independently a saturated or unsaturated fatty acid, a saturated or unsaturated carboxylic acid, a vitamin or metabolite thereof, an enzyme co-factor, an antibiotic, or a drug. Subscript m of formula I is an integer from 0 to 5. Subscript n of formula I is an integer from 8 to 20, wherein subscript n is equal to the number of end groups on the dendritic polymer. In some embodiments, at least one-fourth (e.g., ¼, ⅓, ½, ⅔, ¾, or all) the number n of R groups are R'. In some embodiments, at least one-fourth (e.g., ¼, ⅓, ½, ⅔, ¾, or all) the number n of R groups are R".

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes, saturated and unsaturated fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R, 5S, 7R, 8R, 9S, 10S, 12S, 13R, 14S, 17R)-3,7,12-trihydroxy-10,13-dimethylhexadecahydro-1H-cyclopenta[a]phenanthren-17-yl)pentanoic acid, having the structure:

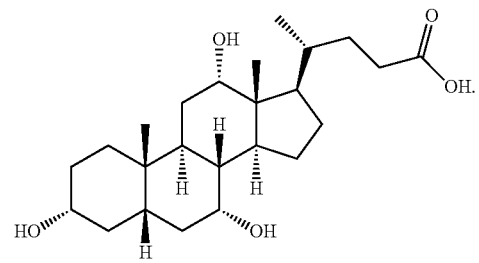

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

Telodendrimer end groups may also include drugs such as aminocaproic acid. One of skill in the art will appreciate that other drugs are useful in the present invention. Telodendrimer end groups can also include saturated and unsaturated carboxylic acids, vitamins, enzyme co-factors, and metabolites.

In some embodiments, each R' can be cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), (3α, 5β, 7α, 12α)-7,12-dihydroxy-3-(3-amino-2-hydroxy-1-propoxy)-cholic acid (CA-3OH—NH$_2$).

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. Subscript n can be about 2, 3, 4, 5, 6, 7, 8, 9, 10, 15, or 20. In some embodiments, subscript n can be from 2 to 10, 2 to 8, 4-10, or 4 to 8. In some embodiments, n is 4-20, or 8-10. In some embodiments, n is 8-20. In some embodiments, n is 8.

In some embodiments, each R' group is the same. Similarly, in some embodiments, each R" group is the same. In some embodiments, at least two different R' groups are present, such as two different amphiphilic groups. In some embodiments, at least two different R" groups are present, such as an unsaturated carboxylic acid (cinnamic acid) and a saturated fatty acid (lauric acid).

The linker L can include any suitable linker. In general, the linkers are bifunctional linkers, having two functional groups for reaction with each of two telodendrimer segments. In some embodiments, the linker can be a heterobifunctional linker. In some embodiments, the linker can be a homobifunctional linker. In some embodiments, the linker L can be polyethylene glycol, polyserine, polyglycine, poly(serine-glycine), aliphatic amino acids, 6-amino hexanoic acid, 5-amino pentanoic acid, 4-amino butanoic acid or beta-alanine. One of skill in the art will recognize that the size and chemical nature of the linker can be varied based on the structures of the telodendrimer segments to be linked.

In some embodiments, linker L is the Ebes linker having the formula:

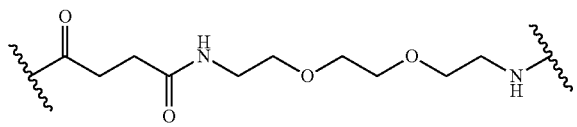 [SMILES: *NCCOCCOCCNC(=O)CCC(*)=O]

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 5 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

Any suitable number of PEG groups can be present. For example, subscript m can be 0, 1, 2, 3, 4, 5, 10, 15, or 20. Subscript m can also be from 0 to 5, 0 to 4, 0 to 3, 0 to 2, 1 to 5, 1 to 4, or 1 to 3. In some embodiments, subscript m is 1.

In some embodiments, the compound of formula I has the structure:

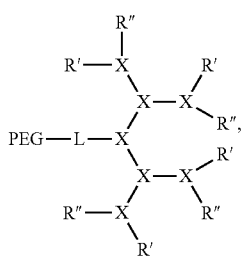

wherein R' is an amphiphilic compound having a hydrophobic face and a hydrophilic face and R" is a saturated or unsaturated fatty acid, a saturated or unsaturated carboxylic acid, a vitamin or metabolite thereof, an enzyme co-factor, an antibiotic, or a drug. In some cases, each branched monomer unit X is lysine. In some cases, each amphiphilic compound having a hydrophobic face and a hydrophilic face (R') is independently selected from the group consisting of cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH) and (3α, 5β, 7α, 12α)-7,12-dihydroxy-3-(3-amino-2-hydroxy-1-propoxy)-cholic acid (CA-3OH—NH$_2$).

In some embodiments, the compound of formula I has the structure:

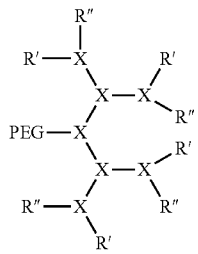

wherein each X is lysine; PEG is PEG5k; each R' is Cholic acid, CA-4OH, CA-5OH, or CA-3OH—NH$_2$; and each R" is selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, aminocaproic acid, riboflavin, pyridoxine, cholecalciferol and a non-steroidal anti-inflammatory drug.

Non-steroidal anti-inflammatory drugs (NSAIDs) useful in the present invention include any known NSAID. Representative NSAIDs include, but are not limited to, etodolac, indomethacin, naproxen, oxaprozin, sulindac, acetylsalicylic acid, fiflunisal, salicylic acid, salsalate, ibuprofen, dexibruprofen, fenoprofen, ketoprofen, dexketoprofen, flubbiprofen, oxaprozin, loxoprofen, tolmetin, ketorolac, diclofenac, aceclofenac, mefenamic acid, meclofenamic acid, flufenamic acid, tolfenamic acid, among others. In some embodiments, the NSAID can be etodolac, indomethacin, naproxen, oxaprozin, sulindac, acetylsalicylic acid, fiflunisal, salicylic acid, salsalate, ibuprofen, dexibruprofen, fenoprofen, ketoprofen, dexketoprofen, flubbiprofen, oxaprozin, loxoprofen, tolmetin, ketorolac, diclofenac, or aceclofenac. In some embodiments, the NSAID can be etodolac, indomethacin, naproxen, oxaprozin, or sulindac.

In some embodiments, the compound of formula I has the structure:

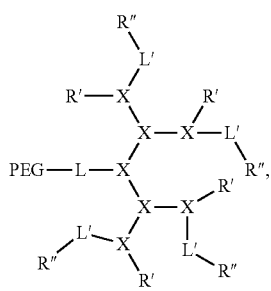

wherein each branched monomer unit X is lysine; and each L' is a bond or a linker. In some embodiments, each L' is a linker Ebes or succinic acid. In some embodiments, each L' is a linker Ebes. In some embodiments, each L' is a succinic acid. In some cases, wherein L' is a succinic acid, R" is an organic moiety (OM) that lacks a carboxylic group, or an OM having a hydroxyl or amine group. In some cases, wherein L' is a succinic acid, R" is an organic moiety (OM) independently selected from the group consisting of riboflavin, pyridoxine, and cholecalciferol. In some cases, wherein L' is a bond or a linker Ebes, R" is an organic moiety (OM) independently selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, and aminocaproic acid. In some cases, wherein L' is a bond or a linker Ebes, R" is a drug.

In some embodiments, the compound of formula I has the structure:

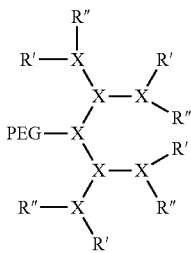

wherein each X is lysine; PEG is PEG5k; each R' is Cholic acid, CA-4OH, CA-5OH, or CA-3OH—NH$_2$; and each R" is selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, aminocaproic acid, riboflavin, pyridoxine and cholecalciferol.

In some embodiments, the compound of formula I has the structure:

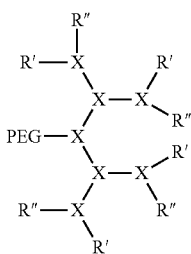

wherein each X is lysine; PEG is PEG5k; each R' is Cholic acid; and each R" is selected from the group consisting of etodolac, indomethacin, naproxen, oxaprozin and sulindac.

In some embodiments, the present invention provides one or more of the telodendrimers of Table A, and/or nanocarriers containing one or more, or at least two, of the telodendrimers of Table A:

TABLE A

| Telodendrimers | |
|---|---|
| Entry | Polymer |
| 2 | PEG$^{5K}$-Biotin$_4$/CA$_4$ |
| 3 | PEG$^{5K}$-(Cinnamic acid)$_4$/CA$_4$ |
| 4 | PEG$^{5K}$-(Lauric acid)$_4$/CA$_4$ |
| 5 | PEG$^{5K}$-(Linoleic acid)$_4$/CA$_4$ |
| 6 | PEG$^{5K}$-(Lipoic acid)$_4$/CA$_4$ |
| 7 | PEG$^{5K}$-(Nicotinic acid)$_4$/CA$_4$ |
| 8 | PEG$^{5K}$-(Octanoic acid)$_4$/CA$_4$ |
| 9 | PEG$^{5K}$-(Oleic acid)$_4$/CA$_4$ |
| 10 | PEG$^{5K}$-(Retinoic acid)$_4$/CA$_4$ |
| 11 | PEG$^{5K}$-(Sorbic acid)$_4$/CA$_4$ |
| 12 | PEG$^{5K}$-(Biotin)$_8$ |
| 13 | PEG$^{5K}$-(Chenodeoxycholic acid)$_8$ |
| 14 | PEG$^{5K}$-(Glycocholic acid)$_8$ |
| 15 | PEG$^{5K}$-(Nicotinic acid)$_8$ |
| 16 | PEG$^{5K}$-(Piromidic Acid$_4$)/CA$_4$ |
| 17 | PEG$^{5K}$-(Caffeic acid$_4$)/CA$_4$ |
| 18 | PEG$^{5K}$-(Ricinoleic acid$_4$)/CA$_4$ |
| 19 | PEG$^{5K}$-(Pantothenic acid$_4$)/CA$_4$ |
| 20 | PEG$^{5K}$-Succ$_4$-(Riboflavin$_4$)/CA$_4$ |
| 21 | PEG$^{5K}$-Succ$_4$-(Pyridoxine$_4$)/CA$_4$ |
| 22 | PEG$^{5K}$-Succ$_4$-(Cholecalciferol$_4$)/CA$_4$ |

B. Surface Crosslinkable Hybrids

In some embodiments, the present invention provides various crosslinkable telodendrimers. Crosslinkable telodendrimers can be incorporated into various nanocarriers such that each micelle nanocarrier contains at least two crosslinkable telodendrimer molecules. The crosslinkable groups of the crosslinkable telodendrimers can then be crosslinked to increase the stability of the nanocarrier. In some cases, the crosslinks are reversible crosslinks, thus providing reversibly crosslinked nanocarriers. For example, where the crosslinks are disulfide bonds, the crosslinks in a nanocarrier can be reduced with a reducing agent.

Crosslinkable groups suitable in the compounds of the present invention include any functional group capable of forming a covalent bond with the same functional group on another telodendrimer, or with a complementary functional group on another telodendrimer. Functional groups capable of forming a covalent bond with the same functional group include thiols. Thiols useful in the compounds of the present invention include any thiols, such as cysteine. In some cases, where the thiol is an end group of a telodendrimer, the thiol can be N-acetyl cysteine.

Complementary functional groups useful as Y$^1$ or Y$^2$ crosslinkable groups and capable of forming a covalent bond include any one or more of the foregoing thiols. Alternatively, complementary functional groups useful as Y$^1$ or Y$^2$ crosslinkable groups and capable of forming a covalent bond include boronic acids and a 1,2-diols. Boronic acids useful in the compounds of the present invention include, but are not limited to, phenylboronic acid, 2-thienylboronic acid, methylboronic acid, and propenylboronic acid. Suitable 1,2-diols include alkyl-1,2-diol and phenyl-1,2-diols such as catechol.

In some embodiments, each crosslinkable group Y$^1$ and Y$^2$ can be any of boronic acid, dihydroxybenzene or a thiol. In some embodiments, each crosslinkable group Y$^1$ and Y$^2$ can be any of boronic acid or dihydroxybenzene. In some embodiments, each crosslinkable group Y$^1$ and Y$^2$ can be phenylboronic acid or dihydroxybenzene. In some embodiments, each crosslinkable group Y$^1$ can be phenylboronic acid or dihydroxy benzene. In some embodiments, each crosslinkable group Y$^1$ can be carboxyphenylboronic acid, carboxynitrophenyl boronic acid or 3,4-dihydroxybenzoic acid. In some embodiments, each crosslinkable group $Y^1$ and $Y^2$ can be a thiol. In some embodiments, each crosslinkable group $Y^1$ and $Y^2$ can be cysteine. In some embodiments, each crosslinkable group $Y^2$ can be cysteine.

In some embodiments, the present invention provides a compound of the following formula:

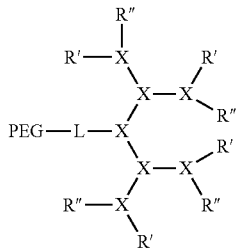

wherein X is a branched monomer unit; L is a bond or a linker; each PEG is a polyethyleneglycol (PEG) polymer, wherein each PEG polymer has a molecular weight of 1-50 kDa; each R' is independently an amphiphilic compound having a hydrophobic face and a hydrophilic face and each R' is independently linked to a different branched monomer unit X via a bond or a linker; and each R" is independently a crossslinkable group selected from the group consisting of a thiol, a cysteine, and an N-acetyl cysteine, wherein the crosslinkable groups are each independently linked to a different branched monomer unit X via a bond or a linker.

In some embodiments, the present invention provides a compound of the following formula:

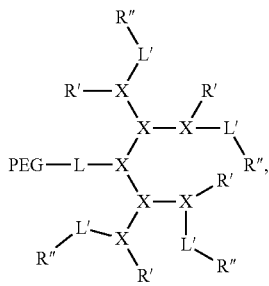

wherein X is a branched monomer unit; L is a bond or a linker; each L' is a bond or a linker; each PEG is a polyethyleneglycol (PEG) polymer, wherein each PEG polymer has a molecular weight of 1-50 kDa; each R' is independently an amphiphilic compound having a hydrophobic face and a hydrophilic face and each R' is independently linked to a different branched monomer unit X via a bond or a linker; and each R" is independently a crossslinkable group selected from the group consisting of a thiol, a cysteine, and an N-acetyl cysteine, wherein the crosslinkable groups are each independently linked to a different branched monomer unit X via a bond or a linker. In some embodiments, the linker L' can be Ebes, aminocaproic acid, 5-aminopentanoic acid, 4-aminobutanoic acid, or β-alanine. In some embodiments, the linker L' can be aminocaproic acid, 5-aminopentanoic acid, 4-aminobutanoic acid, or β-alanine. In some embodiments, the linker L' can be aminocaproic acid. In some embodiments, the linker L' can be 6-aminohexanoic acid (Ahx).

In some embodiments, each R" is independently linked to a different branched monomer unit X via a linker Ebes, aminocaproic acid, 5-aminopentanoic acid, 4-aminobutanoic acid, or β-alanine. In some embodiments, each R' is independently linked to a different branched monomer unit X via a linker Ebes, aminocaproic acid, 5-aminopentanoic acid, 4-aminobutanoic acid, or β-alanine. In some embodiments, each R' is independently linked to a different branched monomer unit via a linker, and each R" is independently linked to a different branched monomer unit via a linker, and each linker is independently selected from the group consisting of Ebes, aminocaproic acid, 5-aminopentanoic acid, 4-aminobutanoic acid, or β-alanine.

In some embodiments, each branched monomer unit X is independently selected from the group consisting of a diamino carboxylic acid, a dihydroxy carboxylic acid and a hydroxyl amino carboxylic acid. In some embodiments, each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. In some embodiments, each dihydroxy carboxylic acid is independently selected from the group consisting of glyceric acid, 2,4-dihydroxybutyric acid, 2,2-Bis(hydroxymethyl)propionic acid, and 2,2-Bis(hydroxymethyl)butyric acid. In some embodiments, each hydroxyl amino carboxylic acid is independently selected from the group consisting of serine, threonine, and homoserine. In some embodiments, diamino carboxylic acid is an amino acid. In some embodiments, each branched monomer unit X is lysine.

In some embodiments, each R' is independently selected from the group consisting of cholic acid, (3α, 5β, 7α, 12α)-7,12-dihydroxy-3-(2,3-dihydroxy-1-propoxy)-cholic acid, (3α, 5β, 7α, 12α)-7-hydroxy-3,12-di(2,3-dihydroxy-1-propoxy)-cholic acid, and (3α, 5β, 7α, 12α)-7,12-dihydroxy-3-(3-amino-2-hydroxy-1-propoxy)-cholic acid. In some embodiments, each R' is cholic acid. In some embodiments, the PEG is from 1-50 kDa. In other embodiments, the PEG is from 1-10 kDa. In some other embodiments, the PEG is, or is about, 5 kDa.

In some embodiments, the compound has the following structure:

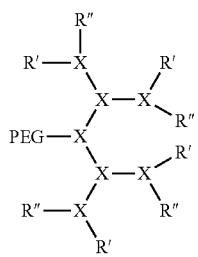

wherein PEG is $PEG_{5k}$, X is lysine, R' is cholic acid, R" is cysteine or N-acetylcysteine, and R" is linked to the corresponding monomer X via a linker selected from the group consisting of aminocaproic acid, 5-aminopentanoic acid, 4-aminobutanoic acid, and β-alanine.

In some embodiments, the compound has the following structure:

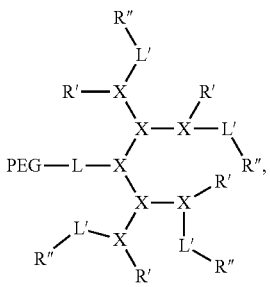

wherein each branched monomer unit X is lysine; L is a bond or a linker; linker L' is 6-amino hexanoic acid; PEG is PEG5k; each R' is cholic acid; and each R" is N-acetyl cysteine.

In some embodiments, the present invention provides one or more of the crosslinkable telodendrimers of Table B, and/or nanocarriers containing one or more, or at least two, of the crosslinkable telodendrimers of Table B:

TABLE B

Cross-linkable hybrid telodendrimers containing a crosslinkable group R"

| Entry | Polymer |
|---|---|
| 23 | PEG$^{5K}$-CA$_4$/Ebes$_4$-Cysteine$_4$ |
| 24 | PEG$^{5K}$-CA$_4$/(Aminocaproic acid)$_4$-Cysteine$_4$ |
| 25 | PEG$^{5K}$-CA$_4$/(5-Aminopentanoic acid)$_4$-Cysteine$_4$ |
| 26 | PEG$^{5K}$-CA$_4$/(4-Aminobutanoic acid)$_4$-Cysteine$_4$ |
| 27 | PEG$^{5K}$-CA$_4$/(β-alanine)$_4$-Cysteine$_4$ |
| 28 | PEG$^{5K}$-CA$_4$/Ebes$_4$-N-acetylcysteine$_4$ |
| 29 | PEG$^{5K}$-CA$_4$/(Aminocaproic acid)$_4$-N-acetylcysteine$_4$ |
| 30 | PEG$^{5K}$-CA$_4$/(5-Aminopentanoic acid)$_4$-N-acetylcysteine$_4$ |
| 31 | PEG$^{5K}$-CA$_4$/(4-Aminobutanoic acid)$_4$-N-acetylcysteine$_4$ |
| 32 | PEG$^{5K}$-CA$_4$/(β-alanine)$_4$-N-acetylcysteine$_4$ |

A. Crosslinkable Organic Moiety Hybrids

In some embodiments, the present invention provides a compound of formula II:

$$(PEG)_m\text{-}A_p\text{-}L\text{-}D(Y^1)_q\text{---}(R)_n \quad (II)$$

wherein A is linked to at least one PEG group; D is a dendritic polymer having a single focal point group, a plurality of branched monomer units X, a plurality of crosslinkable groups $Y^1$, and a plurality of end groups R; L is a bond or a linker linked to the focal point group of the dendritic polymer; each PEG is a polyethyleneglycol (PEG) polymer, wherein each PEG polymer has a molecular weight of 1-50 kDa; each R has a molecular weight of greater than 100 g/mol and less than 2000 g/mol; each R is independently selected from R' and R", wherein each R' is independently an amphiphilic compound having a hydrophobic face and a hydrophilic face, and each R" is independently selected from the group consisting of a saturated or unsaturated fatty acid, a saturated or unsaturated carboxylic acid, a vitamin or metabolite thereof, an enzyme co-factor, an antibiotic, and a drug; subscript n is an integer from 8 to 20, wherein subscript n is equal to the number of end groups on the dendritic polymer; each $Y^1$ is independently a crosslinkable group selected from the group consisting of a thiol, a boronic acid, a 1,2-diol, or a cysteine group; subscript m is an integer from 0 to 5; and; each of subscripts p and q are 0 or from 2 to 10, such that one of subscripts p and q is from 2 to 10. In some embodiments, at least one-fourth (e.g., ¼, ⅓, ½, ⅔, ¾, or all) the number n of R groups are R'. In some embodiments, at least one-fourth (e.g., ¼, ⅓, ½, ⅔, ¾, or all) the number n of R groups are R".

In some embodiments, each branched monomer unit X is independently selected from the group consisting of a diamino carboxylic acid, a dihydroxy carboxylic acid and a hydroxyl amino carboxylic acid. In some embodiments, each branched monomer unit X is lysine. In some embodiments, each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. In some embodiments, each dihydroxy carboxylic acid is independently selected from the group consisting of glyceric acid, 2,4-dihydroxybutyric acid, 2,2-Bis(hydroxymethyl)propionic acid, and 2,2-Bis(hydroxymethyl)butyric acid. In some embodiments, each hydroxyl amino carboxylic acid is independently selected from the group consisting of serine, threonine, and homoserine. In some embodiments, the diamino carboxylic acid is an amino acid.

In some embodiments, each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH$_2$). In some embodiments, each R' is cholic acid.

In some embodiments, linker L is selected from the group consisting of polyethylene glycol, polyserine, polyglycine, poly(serine-glycine), aliphatic amino acids, 6-amino hexanoic acid, 5-amino pentanoic acid, 4-amino butanoic acid and beta-alanine. In some embodiments, linker L is the Ebes linker having the formula:

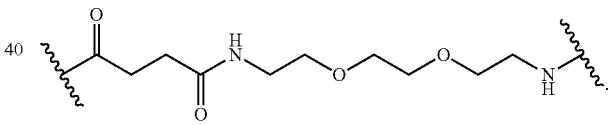

In some embodiments, the compound of formula II is a compound of formula IIb:

$$PEG\text{-}D(Y^1)_q\text{---}(R)_n \quad (IIb)$$

wherein subscript q is an integer from 2 to 10.

In some embodiments, the compound has the following structure:

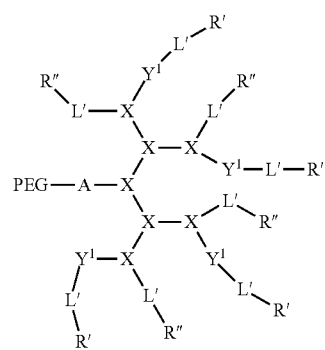

wherein A is a monomer or oligomer of lysine or absent; each L' is independently a bond or a linker Ebes, aminocaproic acid, 5-aminopentanoic acid, 4-aminobutanoic acid, β-alanine, or succinic acid; PEG has a molecular weight of 1-50 kDa; each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH2); each R" is independently selected from the group consisting of a saturated or unsaturated fatty acid, a saturated or unsaturated carboxylic acid, a vitamin or metabolite thereof, an enzyme co-factor, an antibiotic, and a drug; each branched monomer unit X is a diaminocarboxylic acid; and each $Y^1$ is a thiol, a boronic acid, a 1,2-diol, or a cysteine.

In some embodiments, the compound has the following structure:

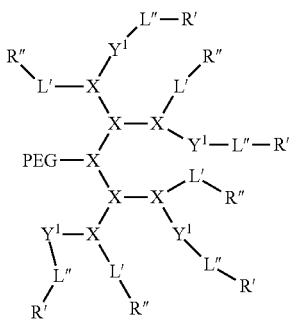

wherein each L' and L" is independently a bond or a linker Ebes, aminocaproic acid, 5-aminopentanoic acid, 4-aminobutanoic acid, β-alanine, or succinic acid; PEG has a molecular weight of 1-50 kDa; each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—NH$_2$); each R" is independently selected from the group consisting of a saturated or unsaturated fatty acid, a saturated or unsaturated carboxylic acid, a vitamin or metabolite thereof, an enzyme co-factor, an antibiotic, and a drug; each branched monomer unit X is a diaminocarboxylic acid; and each $Y^1$ is a thiol, boronic acid, a 1,2-diol, or a cysteine.

In some embodiments, the PEG is from 1-50 kDa. In other embodiments, the PEG is from 1-10 kDa. In some other embodiments, the PEG is, or is about, 5 kDa. In some embodiments, each R" is independently selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, aminocaproic acid, riboflavin, pyridoxine, and cholecalciferol. In some embodiments, each R' is cholic acid. In some embodiments, A is absent. In some embodiments, each branched monomer unit X is lysine.

In some embodiments, the linker L' is succinic acid and each R" is independently selected from the group consisting of riboflavin, pyridoxine, and cholecalciferol. In some embodiments, the linker L' is a bond or a linker Ebes, aminocaproic acid, 5-aminopentanoic acid, 4-aminobutanoic acid, or β-alanine, and each R" is independently selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, and aminocaproic acid. In some embodiments, the linker L' is a bond, and the linker L" is a linker Ebes, aminocaproic acid, 5-aminopentanoic acid, 4-aminobutanoic acid, or β-alanine. In some cases, the linker L" is a linker Ebes.

In some embodiments, the present invention provides one or more of the crosslinkable telodendrimers of Table C, and/or nanocarriers containing one or more, or at least two, of the crosslinkable telodendrimers of Table C:

TABLE C

Cross-linkable hybrid telodendrimers containing crosslinkable group $Y^2$

| Entry | Polymer |
|---|---|
| 33 | PEG$^{5K}$-(Biotin)$_4$/Cys$_4$-Ebes$_4$-CA$_4$ |
| 34 | PEG$^{5K}$-(Cinnamic acid)$_4$/Cys$_4$-Ebes$_4$-CA$_4$ |
| 35 | PEG$^{5K}$-(Lauric acid)$_4$/Cys$_4$-Ebes$_4$-CA$_4$ |
| 36 | PEG$^{5K}$-(Linoleic acid)$_4$/Cys$_4$-Ebes$_4$-CA$_4$ |
| 37 | PEG$^{5K}$-(Nicotinic acid)$_4$/Cys$_4$-Ebes$_4$-CA$_4$ |
| 38 | PEG$^{5K}$-(Octanoic acid)$_4$/Cys$_4$-Ebes$_4$-CA$_4$ |
| 39 | PEG$^{5K}$-(Oleic acid)$_4$/Cys$_4$-Ebes$_4$-CA$_4$ |
| 40 | PEG$^{5K}$-(Retinoic acid)$_4$/Cys$_4$-Ebes$_4$-CA$_4$ |
| 41 | PEG$^{5K}$-(Sorbic acid)$_4$/Cys$_4$-Ebes$_4$-CA$_4$ |
| 42 | PEG$^{5K}$-(Piromidic Acid$_4$)/Cys$_4$-Ebes$_4$-CA$_4$ |
| 43 | PEG$^{5K}$-(Caffeic acid$_4$) Cys$_4$-Ebes$_4$-/CA$_4$ |
| 44 | PEG$^{5K}$-(Ricinoleic acid$_4$)/Cys$_4$-Ebes$_4$-CA$_4$ |
| 45 | PEG$^{5K}$-(Pantothenic acid$_4$)/Cys$_4$-Ebes$_4$-CA$_4$ |
| 46 | PEG$^{5K}$-(Aminocaproic acid$_4$)/Cys$_4$-Ebes$_4$-CA$_4$ |
| 47 | PEG$^{5K}$-(Succinate$_4$-Riboflavin$_4$)/Cys$_4$-Ebes$_4$-CA$_4$ |
| 48 | PEG$^{5K}$-(Succinate$_4$-Pyridoxine$_4$)/Cys$_4$-Ebes$_4$-CA$_4$ |
| 49 | PEG$^{5K}$-(Succinate$_4$-Cholecalciferol$_4$)/Cys$_4$-Ebes$_4$-CA$_4$ |

IV. Nanocarriers

The telodendrimers of the present invention aggregate to form nanocarriers with a hydrophobic core and a hydrophilic exterior. In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, the nanocarrier includes a hydrophobic drug or an imaging agent, such that the hydrophobic drug or imaging agent is sequestered in the hydrophobic pocket of the nanocarrier. Hydrophobic drugs useful in the nanocarrier of the present invention includes any drug having low water solubility. In some embodiments, the hydrophobic drug in the nanocarrier can be bortezomib, paclitaxel, SN38, camptothecin, etoposide and doxorubicin, docetaxel, daunorubicin, VP16, prednisone, dexamethasone, vincristine, vinblastine, temsirolimus and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the present invention.

Other drugs useful in the present invention also include radionuclides, such as $^{67}Cu$, $^{90}Y$, $^{123}I$, $^{125}I$, $^{131}I$, $^{177}Lu$, $^{188}Re$, $^{186}Re$ and $^{211}At$. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

In some embodiments, the present invention provides a nanocarrier having an interior and an exterior, the nanocarrier comprising at least two conjugates, wherein at least one conjugate is a compound of formula III, wherein each conjugate comprises a polyethylene glycol (PEG) polymer; at least two R', wherein R' is an amphiphilic compound having a hydrophobic face and a hydrophilic face; and a dendritic polymer covalently attached to the PEG, and the amphiphilic compounds, wherein each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier. In some embodiments, each conjugate is a conjugate of formula III. In some embodiments, each R' is cholic acid.

In some embodiments, the present invention provides a nanocarrier having an interior and an exterior, the nanocarrier comprising at least two conjugates, wherein at least one conjugate is a compound of formula I, wherein each conjugate comprises a polyethylene glycol (PEG) polymer; at least two R', wherein R' is an amphiphilic compound having a hydrophobic face and a hydrophilic face; and a dendritic polymer covalently attached to the PEG, and the amphiphilic compounds, wherein each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier. In some embodiments, each conjugate is a conjugate of formula I. In some embodiments, each R' is cholic acid.

In some embodiments, the present invention provides a reversibly crosslinked nanocarrier having an interior and an exterior, the nanocarrier comprising at least two conjugates, wherein at least one conjugate is a compound of formula II, wherein each conjugate comprises a polyethylene glycol (PEG) polymer; at least two R', wherein each R' is independently an amphiphilic compound having a hydrophobic face and a hydrophilic face; crosslinkable groups $Y^1$; and a dendritic polymer covalently attached to the PEG, the R' and R" groups, wherein the conjugates self-assemble in an aqueous solvent to form the nanocarrier such that a hydrophobic pocket is formed in the interior of the nanocarrier by the orientation of the hydrophobic face of each R' towards each other, and wherein the PEG of each conjugate self-assembles on the exterior of the nanocarrier wherein at least two conjugates are reversibly crosslinked via the crosslinkable groups. In some embodiments, each conjugate is a compound of formula II. In some embodiments, the nanocarrier includes crosslinked thiol groups. In some embodiments, each R' is cholic acid.

In some embodiments, the present invention provides a reversibly crosslinked nanocarrier having an interior and an exterior, the nanocarrier comprising at least two conjugates, wherein at least one conjugate is a compound of

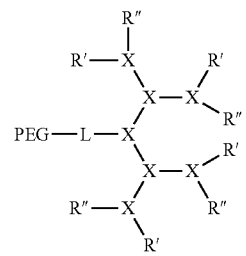

as described above, wherein each conjugate comprises amphiphilic compounds R' having a hydrophobic face and a hydrophilic face; crosslinkable groups R"; and a polyethylene glycol (PEG) polymer, wherein each conjugate self-assembles in an aqueous solvent to form the nanocarrier such that a hydrophobic pocket is formed in the interior of the nanocarrier by the orientation of the hydrophobic face of each amphiphilic compound towards each other, wherein the PEG of each conjugate self-assembles on the exterior of the nanocarrier, and wherein at least two conjugates are reversibly crosslinked via the crosslinkable groups. In some embodiments, each R' is cholic acid. In some embodiments, each conjugate is a compound of

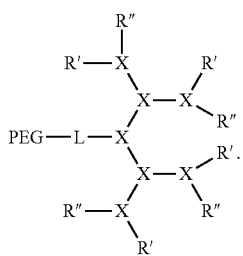

V. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier. In some embodiments, the drug is a hydrophobic drug sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present invention are useful for the treatment of infection by pathogens such as viruses, bacteria, fungi, and parasites. Other diseases can be treated using the nanocarriers of the present invention.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Method of Imaging

In some embodiments, the present invention provides a method of imaging, including administering to a subject to be imaged, an effective amount of a nanocarrier of the present invention, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DID (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

VII. Examples

General Methods

The following examples use procedures outlined in Therapeutic Delivery 2013, 10, 1279-1292; Nanomedicine (Lond) 2014, 9, 1807-1820; Biomaterials 2015, 67, 183-93; and Nanotechnology 2016, 27(42), 425103.

Telodendrimers of the present invention are made according to the procedures outlined below or according to the procedures described in Li Y, et al., "Well-defined, reversible disulfide cross-linked micelles for on-demand paclitaxel delivery", Biomaterials 2011, 32(27), 6633-6645 and Bharadwaj G, et al., "Cholic acid-based novel micellar nanoplatform for delivering FDA-approved taxanes", Nanomedicine (London, England) 2017 using suitable reagents.

Example 1: Preparation of Organic Moiety Hybrid Telodendrimers

Taxanes (paclitaxel, docetaxel, cabazitaxel) are an important class of chemotherapeutic drugs that remained a cornerstone in the treatment of wide variety of cancers. However, serious side-effects arising from the drug and the excipient are often observed in the clinics. The development of cholic acid (CA) based micellar nano-carrier for effective encapsulation and delivery of paclitaxel has been previously reported. This nanoplatform is assembled from telodendrimers (PEG$^{5K}$-CA$_8$) comprised of a 5000 dalton linear PEG with a cluster of eight cholic acids on one end. Described herein is a series of novel hybrid telodendrimers (PEG$^{5K}$-OM$_4$/CA$_4$) with improved physicochemical properties, drug-loading capacity and efficiency, produced by replacement of four of the eight cholic acids with biocompatible organic moiety (OM). Some of these hybrid telodendrimers can generate micelles with narrow size distributions, low critical micelle concentration (CMC) values (0.9-6.4 µM), better hemato-compatibility (up to 2 mg/ml as tested) and lack of in vitro cytotoxicity (up to 2 mg/ml). Along with PEG$^{5K}$-CA$_8$, the cholic acid based hybrid nanoplatform described herein is the first of its kind that can stably capsulate all three FDA-approved taxanes with nearly 100% efficiency up to 20% (w/w) loading.

Materials

Docetaxel and cabazitaxel were purchased from Adooq Bioscience. Monomethyl terminated polyethylene glycol monoamine (MeO-PEG-NH$_2$, molecular weight 5 KDa) was purchased from Rapp Polymere (Tubingen, Germany). (Fmoc)lysine(Fmoc)OH and 6-Cl-HOBt were purchased from Aapptec. (Fmoc)lysine(Boc)OH was purchased from Combi-Blocks Inc. N,N'-Diisopropylcarbodiimide (DIC), Retinoic acid, cinnamic acid, biotin, lipoic acid, niacin, octanoic acid, oleic acid and linoleic acid were purchased from Sigma Aldrich. Lauric acid was purchased from Acros Organics. Sorbic acid was purchased from TCI America. Chendeoxycholic acid and glycocholic acid were purchased from Chem-Ipex International. Sequence grade DMF and diethyl ether were purchased from Fisher Scientific. MTS reagent was purchased from Promega. Human breast cancer cell line MDA-MB-231 from American Type Culture Collection (ATCC) was cultured in Eagle's Minimum Essential Medium (ATCC 30-2003) supplemented with 10% fetal bovine serum (FBS) (ATCC 30-2020), 1% penicillin-streptomycin (PS) (Life Technologies), and 1% nonessential amino acids (NEAA) (Life Technologies) at 37° C. with 5% CO$_2$.

Synthesis of PEG$^{5K}$-OM$_4$/CA$_4$ and PEG$^{5K}$-OM$_8$

Hybrid TDs PEG$^{5K}$-OM$_4$/CA$_4$ were synthesized using MeO-PEG$^{5K}$-NH$_2$ as the starting material via solution-phase peptide coupling (FIG. 5A) followed by ether precipitation and removal of the uncoupled reagents by centrifugation after each coupling reaction. In brief, (Fmoc)Lys(Fmoc)-OH (3 eq.) was coupled on the N-terminus of MeO-PEG$^{5K}$-NH$_2$ using DIC and HOBt as coupling reagents overnight until a negative Kaiser test result was obtained, indicating completion of the coupling reaction. Completion of reaction was further verified by TLC using DCM/MeOH (9:1) as eluent. PEGylated molecules were precipitated by adding cold ether. After removal of supernatant, residue was re-dissolved in DMF and precipitated again by adding cold ether. Re-dissolving and precipitation was carried out once more before final washing with cold ether twice. Fmoc groups were removed by the treatment with 20% (v/v) 4-methylpiperidine in dimethylformamide (DMF) for 3 h, and the PEGylated molecules were precipitated and washed in the same way as above. White powder precipitate was dried under vacuum and one coupling of (Fmoc)Lys(Fmoc)-OH and one coupling of (Fmoc)lys(Boc)-OH were carried out sequentially, to generate a third generation of dendritic polylysine terminated with four Boc and Fmoc groups on one end of PEG. Boc group was subsequently removed using 50% (v/v) TFA/DCM followed by ether precipitation and washing as above. Organic building block with free —COOH was then coupled to the free primary amine of the PEG-oligolysine dendrimer using DIC and HOBt as coupling reagents. CA-NHS ester was finally coupled to the remaining terminal primary amines after removal of Fmoc with 20% (v/v) 4-methylpiperidine. The TD solution was then dialysed against 4 L water in a dialysis tube with molecular weight cut off of 7000 KDa; reservoir water was refreshed completely four times in 48 h. Finally, the TD was lyophilized to yield white to light yellow colored hybrid TDs.

PEG$^{5K}$-OMs polymers were synthesized in the similar manner (FIG. 5B) as mentioned above with (Fmoc)Lys (Fmoc)-OH being used instead of (Fmoc)Lys(Boc)-OH to generate a third generation of dendritic polylysine terminated with eight Fmoc group. Removal of Fmoc followed by DIC mediated coupling of organic acid yielded the desired PEG$^{5K}$-OM$_8$ polymers.

Characterization of Polymers

Mass Spectrometry

The mass spectra of the TDs were collected on UltraFlex MALDI-TOF/TOF mass spectrometer (linear mode) using sinapic acid or 2,5-dihydroxybenzoic acid (DHB) as the matrix.

Particle Size and Critical Micellar Concentration (CMC)

Particle size and size distribution of the micelles were measured by dynamic light scattering (DLS) instruments (Microtrac). The micelle concentrations were kept at 1.0 mg/mL in PBS buffer for DLS measurements. Particle size was recorded at room temperature, with triplicate measurements.

CMC value for all the prepared micellar solution was measured fluorometrically according to previously published procedure by using pyrene as a hydrophobic fluorescent probe. In short, stock solution of pyrene was made in methanol and was kept under dark conditions. Aliquots of pyrene were added per well into 96 well black plates and methanol was evaporated at 37° C. Aqueous micellar solutions at different concentrations ($5 \times 10^{-7}$ M to $5 \times 10^{-4}$ M) were added to each well such that resulting pyrene concentration is $6 \times 10^{-6}$ M per well. Plates were left at room temperature under dark conditions overnight. Intensity of fluorescence emissions of the pyrene at 391 nm was collected following excitation at 332 and 336 nm respectively. Plot of I336/I332 vs. concentration was used to calculate cmc values as previously reported.

Hemolysis

Hemolysis from newly prepared hybrid TD PEG$^{5K}$-OM$_4$/CA$_4$ and PEG$^{5K}$-OM$_8$ was performed using fresh citrated blood from mice. The red blood cells (RBCs) from the blood were collected by centrifugation at 1000 rpm for 10 min, washed three times with PBS, and then brought to a final concentration of 2% in PBS. Different concentrations (0.2 and 2.0 mg/mL) of polymers were added to 200 µL of erythrocyte suspension and incubated for 4 h at 37° C. Samples were centrifuged at 1000 rpm for 5 min, and 100 µL of supernatant of all samples was transferred to a 96-well plate for free hemoglobin analysis. Absorbance at 540 nm was recorded for all the samples using a micro-plate reader (SpectraMax M2, Molecular Devices, USA). RBC incubation with Triton-100 (2%) and PBS were used as the positive and negative controls, respectively. The percent hemolysis of RBCs by each sample was calculated using the following formula:

$$(OD_{sample} - OD_{negative\ control})/(OD_{positive\ control} - OD_{negative\ control}) \times 100\%$$

Cytotoxicity

The cytotoxicity of blank nanoparticles was evaluated on human breast cancer cell MDA-MB-231. The CellTiter 96® AQueous One Solution Cell Proliferation Assay (MTS) from Promega was used to determine cell viability. Stock solutions for polymers were prepared at 20 mg/ml in PBS buffer. Cells were seeded at a density of 8000 cells/well in a 96-well plate and then incubated for 24 h at 37° C. After 24 h media was replaced and various concentration of different nanoparticles formulation in fresh medium was added and further incubated for 48-72 h. At the desired time point (48 or 72 h), the medium was changed and supplemented with the MTS/PMS reagent (20:1 ratio) according to the manufacturer recommendation. The samples were then kept in dark at 37° C. with 5% $CO_2$ for 4 hr. The results were obtained using the Spectramax M3 Microplate reader (Molecular Devices).

Drug Loading

Drug (DTX and CTX) was loaded into the nanoparticles using well established solvent evaporation method. Varying amount of drugs (1.5-3 mg) and fixed amount of polymer (15 mg) were added to a 10 ml round bottom flask. Chloroform or methanol (1 ml) was then added to dissolve the sample. Solvent was evaporated under high vacuum to form a thin film. PBS buffer (1 ml) was added to re-constitute the film. Sample was sonicated if necessary and passed through a 0.22 μm filter. The amount of drug loaded in each micelle was analyzed on an HPLC system (Waters) after releasing the drugs from the micelles by adding 9 times of dimethylsulfoxide (DMSO) followed by 10 min sonication. The drug loading was calculated according to the calibration curve generated previously between the HPLC area values and concentrations of drug standard.

Results and Discussion

With the development of several nano-carriers based on liposomes, micelles, polymers, hydrogels and others, many hydrophobic cancer drugs can now be stably encapsulated and delivered site-specifically to cancer site via active or passive targeting. We have recently reported a robust micellar nanoparticle platform that can stably encapsulate a range of hydrophobic agents in the hydrophobic core. This nanoplatform is assembled from amphiphilic TD comprised of natural surfactant CA and dendritic lysines linked to a linear polyethylene glycol (PEG), represented by the formula $PEG^{nK}$-$CA_y$ (where n=molecular weight in kilodaltons (K), y=number of CA units). $PEG^{5K}$-$CA_8$ (FIG. 1), one of our most studied TD can stably encapsulate a range of cancer drugs including paclitaxel (PTX), a taxane and a number of other small molecules, drugs, or chemotherapeutic agents. TD encapsulated PTX with exhibited almost 100% loading efficiency when the initial amount of PTX was <25 wt % of $PEG^{5K}$-$CA_8$ (20 mg/ml), with superior stability (longer than six months) and a size of 20-60 nm. $PEG^{5K}$-$CA_8$ showed superior loading capability with PTX, but it failed to do so with docetaxesl (DTX) and cabazitaxel (CTX) (see table 3 and 5). Given that all three taxanes are structurally quite similar (FIG. 1), this result is somewhat surprising. It does however, illustrate that the success of nanoformulation can depend on the compatibility of the carrier and the small moleculce payload.

Figure 2:
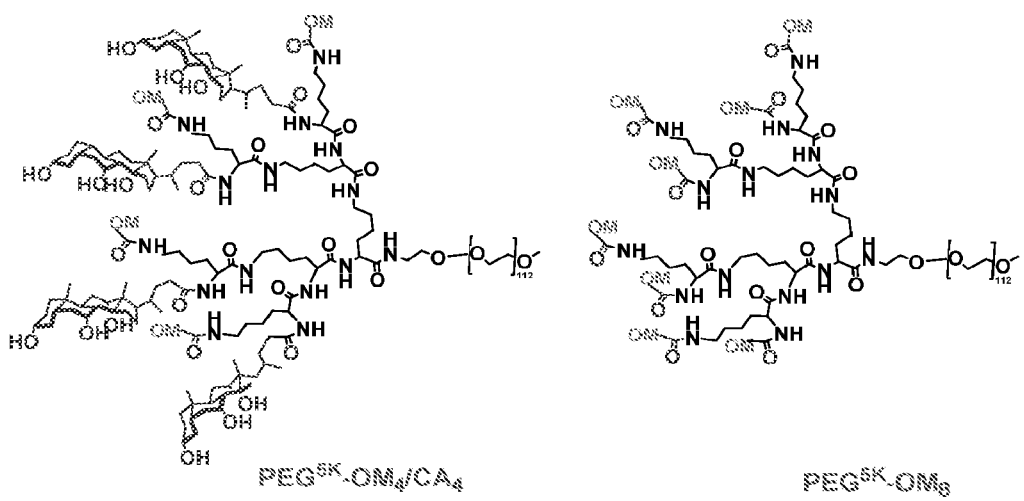
FIG. 2 illustrates two different embodiments of amphiphilic polymers disclosed herein; (left) hybrid telodendrimers, in which the telodendrimer contains cholate (CA) and organic moiety (OM) end groups; and (right) non-hybrid telodendrimers, in which the telodendrimer end groups are all organic moieties (OM).

In the literature, many amphiphilic polymers used in micellar nanoparticles are formed by block co-polymerization and therefore are not well-defined. One unique feature of our amphiphilic polymers is that except for the heterogenous PEG moiety, they are chemically well-defined. Because they are prepared by step-wise peptide-synthesis, one can easily modify the synthesis scheme and introduce different linkers, amphiphilic building blocks or organic moiety (OM) to the termini of the PEG-oligolysine dendrimer. We believe such modification will enable us to generate novel TDs that are tailored towards specific drug or groups of drugs. Here, we focused our effort on developing TDs that can encapsulate all three taxanes: PTX, DTX and CTX. Replacing four of the eight $CA_8$ in $PEG^{5K}$-$CA_8$ with OMs generated TDs (hybrid TDs), represented as $PEG^{5K}$-$OM_4$/$CA_4$ (FIG. 2). We also developed structural analogues of $PEG^{5K}$-$CA_8$ where all the eight CA were replaced with OM (polymers designated as $PEG^{5K}$-$OM_8$) to examine the contribution of CA to drug loading. To minimize toxicity from these newer TDs, we selected only those OMs that are either produced endogenously or consumed by human as part of their diet, or are FDA-approved. Chemical structure of simple aliphatic or aromatic OMs used to prepare different hybrid TDs are shown in Table 1. For our initial study we focused on small set of saturated and unsaturated fatty acids (Table 1; entry 3, 4, 7 & 8), cyclic vitamins (Table 1; entry 1, 6 and 9 with 1 and 6 also being heterocyclic compounds), flavoring agent and food preservative (Table 1; entry 2 & 10 respectively), and lastly a co-factor (Table 1; entry 5 which is also heterocyclic compound). We also included natural surfactant chenodeoxycholic acid and glycocholic acid as an alternative to CA (Table 2, entry 12 & 14) for the polymer class PEG5K-$OM_8$. All the polymers were prepared according to our well established published procedures. See FIGS. 6-10.

TABLE 1

Characterization of micelles formed by hybrid TDs (PEG5K-OM4/CA4)

| Entry | Organic Moiety (OM) | Polymer | Molecular weight (Da; Theo) | Molecular weight (Da; Exp) | CMC (μM) | Particle size (volume %, width) |
|---|---|---|---|---|---|---|
| 1 | Biotin (Vitamin H) | $PEG^{5K}$-(Biotin)$_4$/$CA_4$ | 8416 | 7984 | 3.0 μM | 11.2 (100, 7.13) nm |
| 2 | trans-Cinnamic acid (used as flavoring agent) | $PEG^{5K}$-(Cinnamic acid)$_4$/$CA_4$ | 8033 | 7758 | 0.9 μM | 0.99 (100, 0.26) nm |
| 3 | Lauric acid (saturated fatty acid) | $PEG^{5K}$-(Lauric acid)$_4$/$CA_4$ | 8241 | 7919 | 2.9 μM | 20.8 (100, 32.7) nm |
| 4 | Linoleic acid (polyunsaturated fatty acid) | $PEG^{5K}$-(Linoleic acid)$_4$/$CA_4$ | 8561 | 8146 | 1.4 μM | 0.99 (99, 0.22) nm |
| 5 | Lipoic acid (cofactor) | $PEG^{5K}$-(Lipoic acid)$_4$/$CA_4$ | 8265 | 7819 | 1.7 μM | 11.8 (100, 10.3) nm |
| 6 | Nicotinic acid (Vitamin B3) | $PEG^{5K}$-(Nicotinic acid)$_4$/$CA_4$ | 7931 | 7788 | 3.7 μM | 10.6 (100, 6.37) nm |
| 7 | Octanoic acid (saturated fatty acid) | $PEG^{5K}$-(Octanoic acid)$_4$/$CA_4$ | 8016 | 7548 | 2.2 μM | 10.7 (100, 11.6) nm |

TABLE 1-continued

Characterization of micelles formed by hybrid TDs (PEG5K-OM4/CA4)

| Entry | Organic Moiety (OM) | Polymer | Molecular weight (Da; Theo) | Molecular weight (Da; Exp) | CMC (μM) | Particle size (volume %, width) |
|---|---|---|---|---|---|---|
| 8 | Oleic acid (mono unsaturated fatty acid) | $PEG^{5K}$-(Oleic acid)$_4$/CA$_4$ | 8569 | 8472 | 2.8 μM | 15.9 (100, 22.7) nm |
| 9 | Retinoic acid (Vitamin A metabolite) | $PEG^{5K}$-(Retinoic acid)$_4$/CA$_4$ | 8641 | 7961 | 6.4 μM | 7.9 (95.7, 7.69) nm/ 2048 (4.3, 720) nm |
| 10 | Sorbic acid (food preservative) | $PEG^{5K}$-(Sorbic acid)$_4$/CA$_4$ | 7891 | 7620 | 3.9 μM | 6.9 (89, 4.7) nm/32.1 (11, 15.9) nm |

TABLE 2

Characterization of micelles formed by polymers (PEG5K-OM8)

| Entry | Polymer | Molecular weight (Da; Theo) | Molecular weight (Da; Exp) | CMC (μM) | Particle size (volume %, width) |
|---|---|---|---|---|---|
| 11 | $PEG^{5K}$-(Biotin)$_8$ | 7760 | 7769 | 1.6 μM | 12.5 (100, 10.8) nm |
| 12 | $PEG5^K$-(Chenodeoxycholic acid)$_8$ | 8946 | 8600 | 2.3 μM | 32.5 (100, 25.1) nm |
| 13 | $PEG^{5K}$-(Cinnamic acid)$_8$ | 6991 | 6994 | 22.1 μM | 17.2 (97.5, 28.9) nm/ 5810 (2.5, 973) nm |
| 14 | $PEG^{5K}$-(Glycocholic acid)$_8$ | 9531 | 9472 | 1.2 μM | 18.1 (100, 8.4) nm |
| 15 | $PEG^{5K}$-(Lauric acid)$_8$ | 7409 | 7445 | 13 μM | 10.3 (9.7, 2.3) nm/ 27.8 (90.3, 31) nm |
| 16 | $PEG^{5K}$-(Linoleic acid)$_8$ | 8050 | N.O. | ND | 19.1 (97.4, 28.9) nm/ 5780 (2.6, 3170) nm$^a$ |
| 17 | $PEG^{5K}$-(Lipoic acid)$_8$ | 7457 | N.O. | ND | Wide range of distribution from 21 nm to 5700 nm$^a$ |
| 18 | $PEG^{5K}$-(Nicotinic acid)$_8$ | 6791 | 6867 | 2.9 μM | (32.3, 0.3) nm/ 75.3 (56.3, 81) nm/377 (11.4, 229) nm |
| 19 | $PEG^{5K}$-(Octanoic acid)$_8$ | 6960 | 6915 | 3.0 μM | 15.3 (12.3, 5.2) nm/ 44.7 (82.7, 49.1) nm/ 5970 (5, 676) nm |
| 20 | $PEG^{5K}$-(Oleic acid)$_8$ | 8066 | 7944 | 3.0 μM | 40.9 (89.4, 43.5) nm/ 1249 (3.3, 527 nm)/ 5740 (7.3, 1096) nm |
| 21 | $PEG^{5K}$-(Retinoic acid)$_8$ | 8209 | 7800 | ND | 28 (89.9, 32.7) nm/ 456 (5.7, 298.7) nm/ 1842 (4.4, 1644) nm$^a$ |
| 22 | $PEG^{5K}$-(Sorbic acid)$_8$ | 6703 | 6396 | ND | 25.3 (86.2, 3 3.4) nm/ 5810 (13.8, 958) nm$^a$ |

NO.: Not observable
ND: Not determined a measured at around 0.2 mg/ml

Hemolysis

Figure 3:
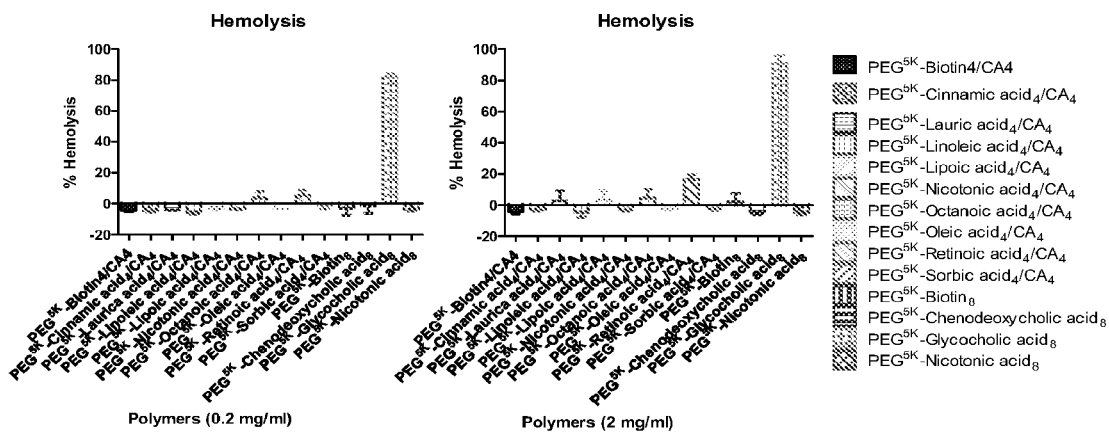
FIG. 3 illustrates the results of an hemolysis assay of the indicated telodendrimers.

Hemato-compatibility is necessary for clinical translation of polymer based drug-carrier. Amphiphilic polymers have the potential to cause disruption of plasma membranes, particularly that of red blood cells (RBC). Hemolysis induced by hybrid TDs and selected $PEG^{5K}$-OM$_8$ polymers were examined to gain insight into their hemato-compatibility. Hemolysis was detected through spectrophotometric measurement of the hemoglobin present in the supermatant of red blood cells treated with the inicellar nanoparticles. Previously, we have shown a dose-dependent red blood cell (RBC) lysis from standard TD $PEG^{5K}$-CA$_8$. The percentage of hemolysis from $PEG^{5K}$-CA$_8$ increased from 9.0% to 16.3% with the increasing concentrations from 0.2 mg/mL to 1.0 mg/mL. For the current set of polymers, hemolytic studies were performed at concentration of 0.2 and 2 mg/ml. FIG. 3 shows the observed hemolytic activity from the hybrid TDs and $PEG^{5K}$-OM$_8$ polymers. At concentration 0.2 mg/ml, most of the polymers showed no hemolytic activity except $PEG^{5K}$-(Glycocholic acid)$_8$ polymer (81.9%). Hemolysis from $PEG^{5K}$-(Octanoic acid)$_4$/CA$_4$ and $PEG^{5K}$-(Retinoic acid)$_4$/CA$_4$ were significantly lower (4.0 and 5.5% respectively). At higher polymer concentration (2 mg/ml), except for $PEG^{5K}$-(Retinoic acid)$_4$/CA$_4$ that showed hemolysis in double digits (16.2%) and $PEG^{5K}$-(Glycocholic acid)$_8$ that showed even higher hemolysis (90.9%), most of the hybrid TDs and PEG5K-OM$_8$ were either devoid of hemolytic activity or only induced minimal hemolysis (2.7, 3.4 and 4.7% for lauric, lipoic and octanoic based hybrid TDs respectively, and 1.9% for $PEG^{5K}$-(Biotin)$_8$). The high hemolytic activity of $PEG^{5K}$-(Retinoic acid)$_4$/CA$_4$ and $PEG^{5K}$-(Glycocholic acid)$_8$ may be of concern, but can likely be mitigated by introducing di-sulfide cross-links in the hydrophobic core as previously reported for our standard TD.

In Vitro Cytotoxicity

Figure 4:
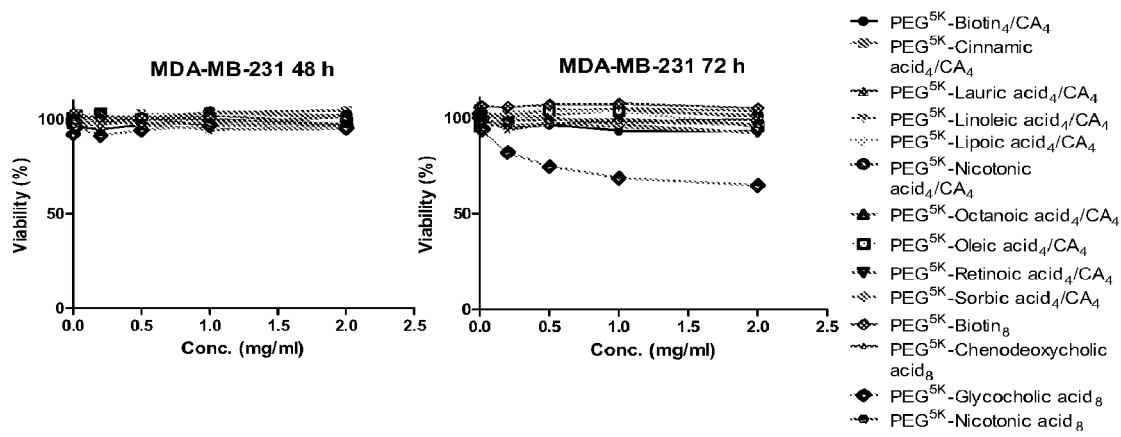
FIG. 4 illustrates the cytotoxicity of the indicated telodendrimers against MDA-MB-231 breast cancer cells. Values reported are the mean f SD for triplicate samples.
Figure 6:
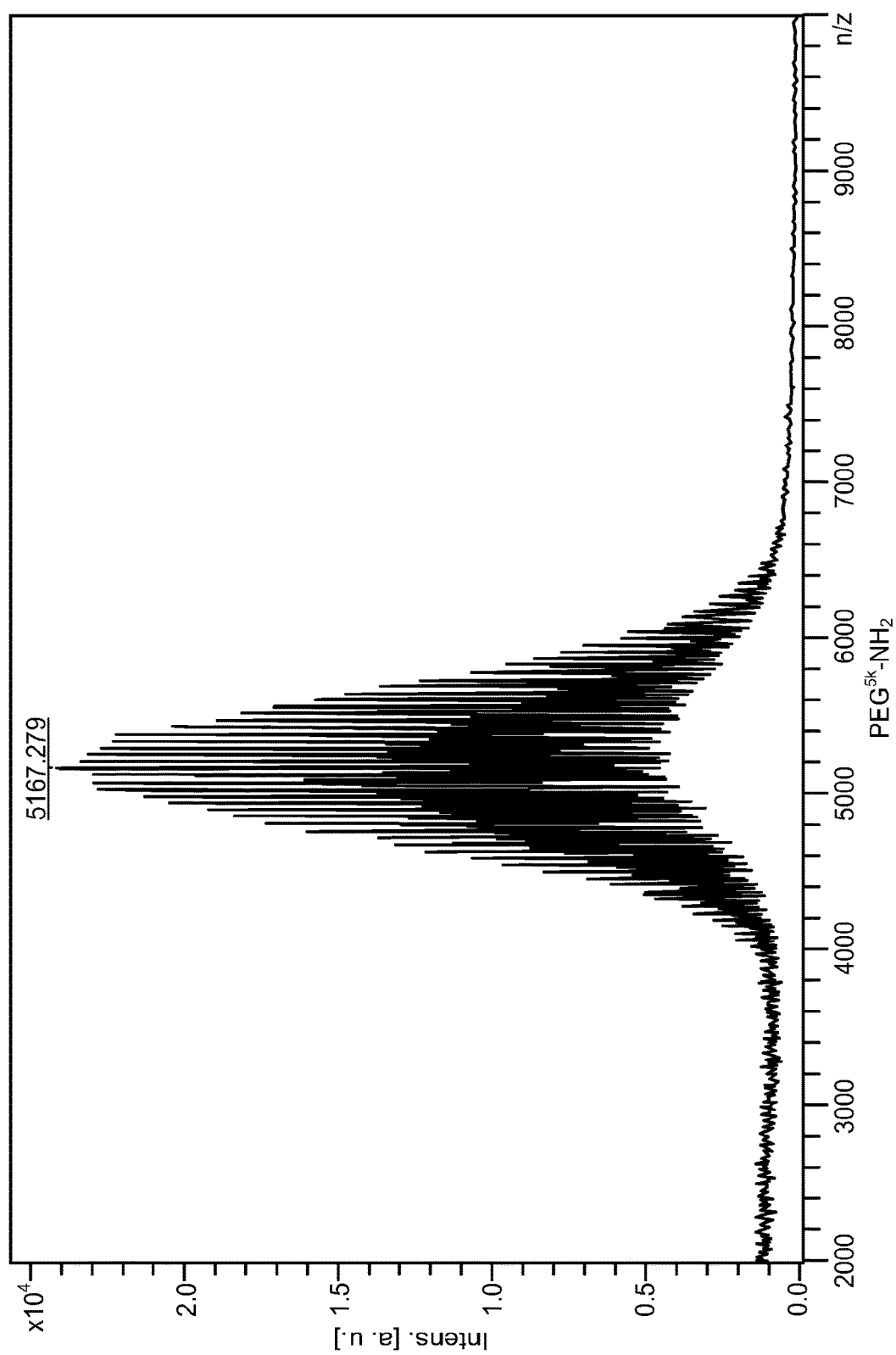
FIG. 6 illustrates MALDI-TOF MS data for PEG polymer PEG$^{5k}$-NH$_2$.
Figure 7:
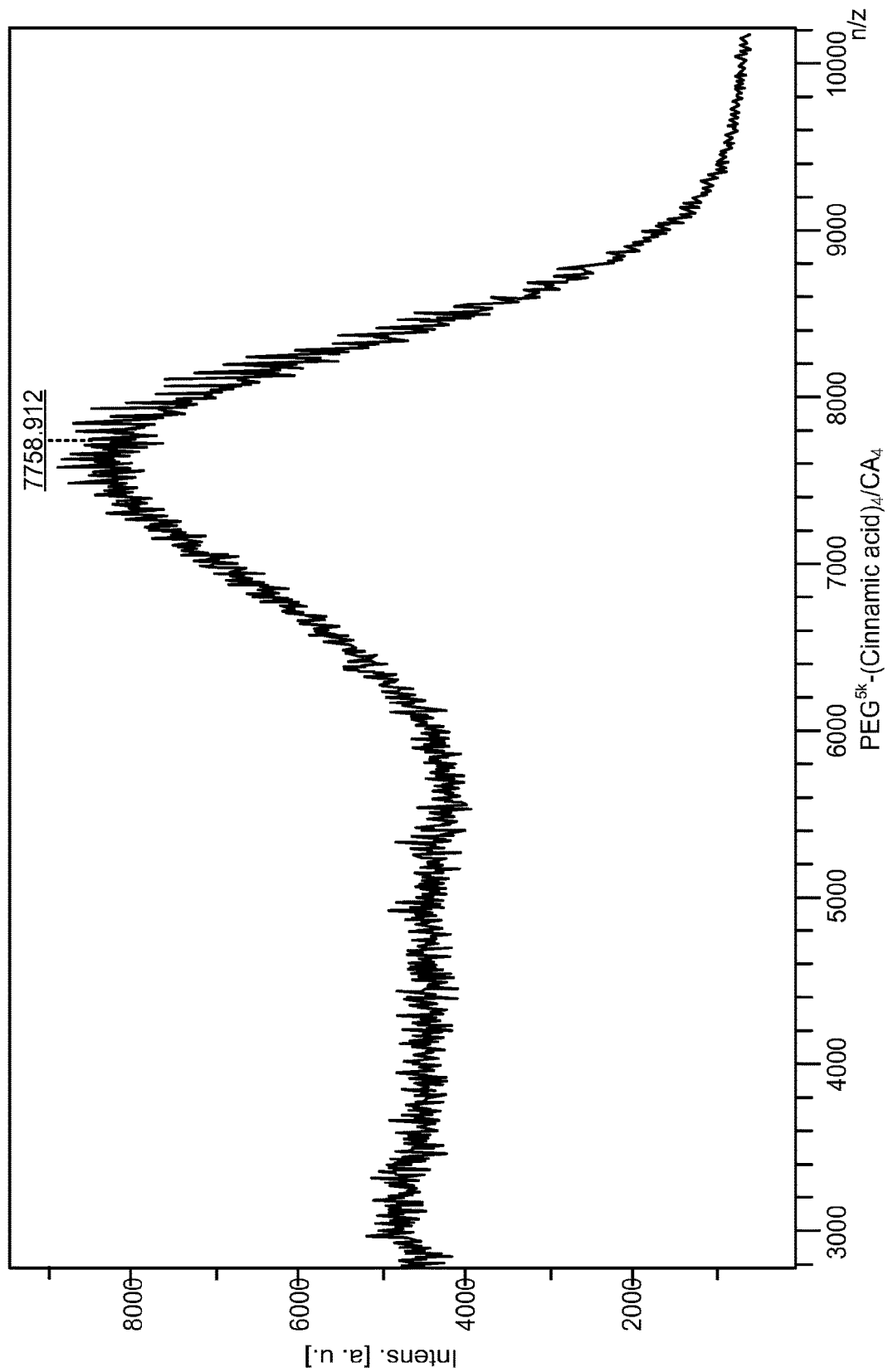
FIG. 7 illustrates MALDI-TOF MS data for hybrid telodendrimer PEG$^{5k}$-(cinnamic acid)$_4$-CA$_4$.
Figure 8:
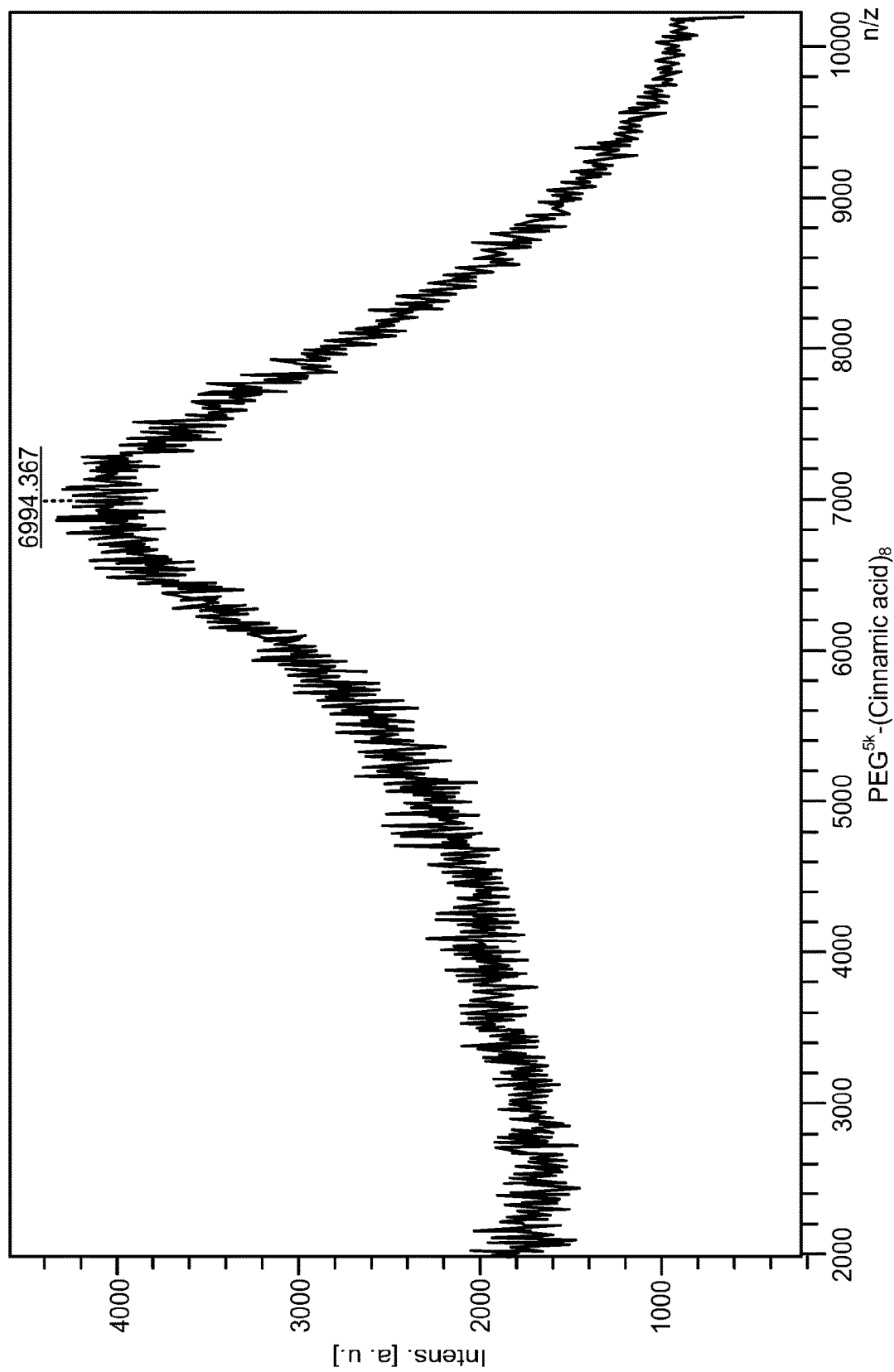
FIG. 8 illustrates MALDI-TOF MS data for non-hybrid telodendrimer PEG$^{5k}$-(cinnamic acid)$_8$.
Figure 9:
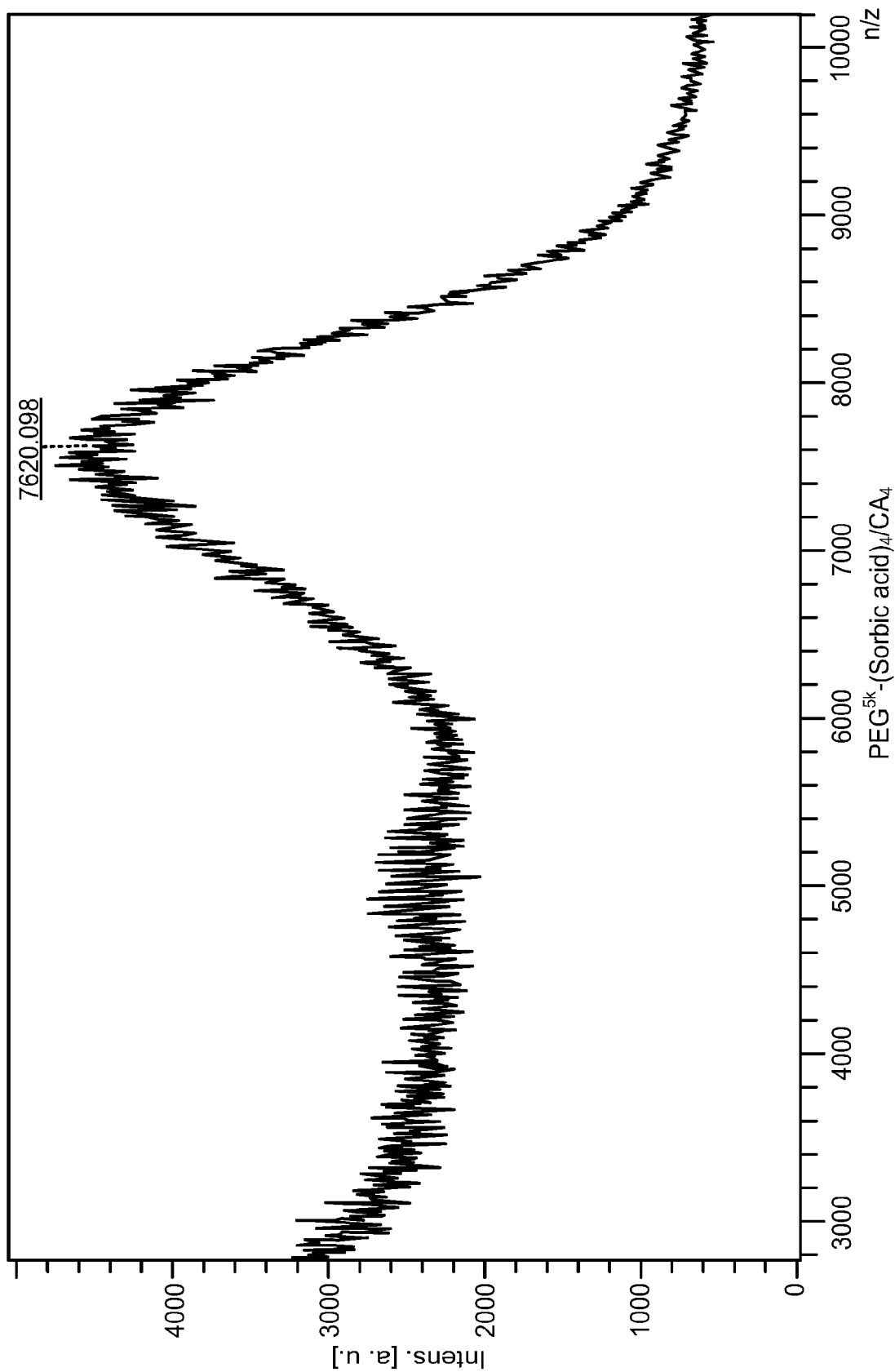
FIG. 9 illustrates MALDI-TOF MS data for hybrid telodendrimer PEG$^{5k}$-(sorbic acid)$_4$-CA$_4$.
Figure 10:
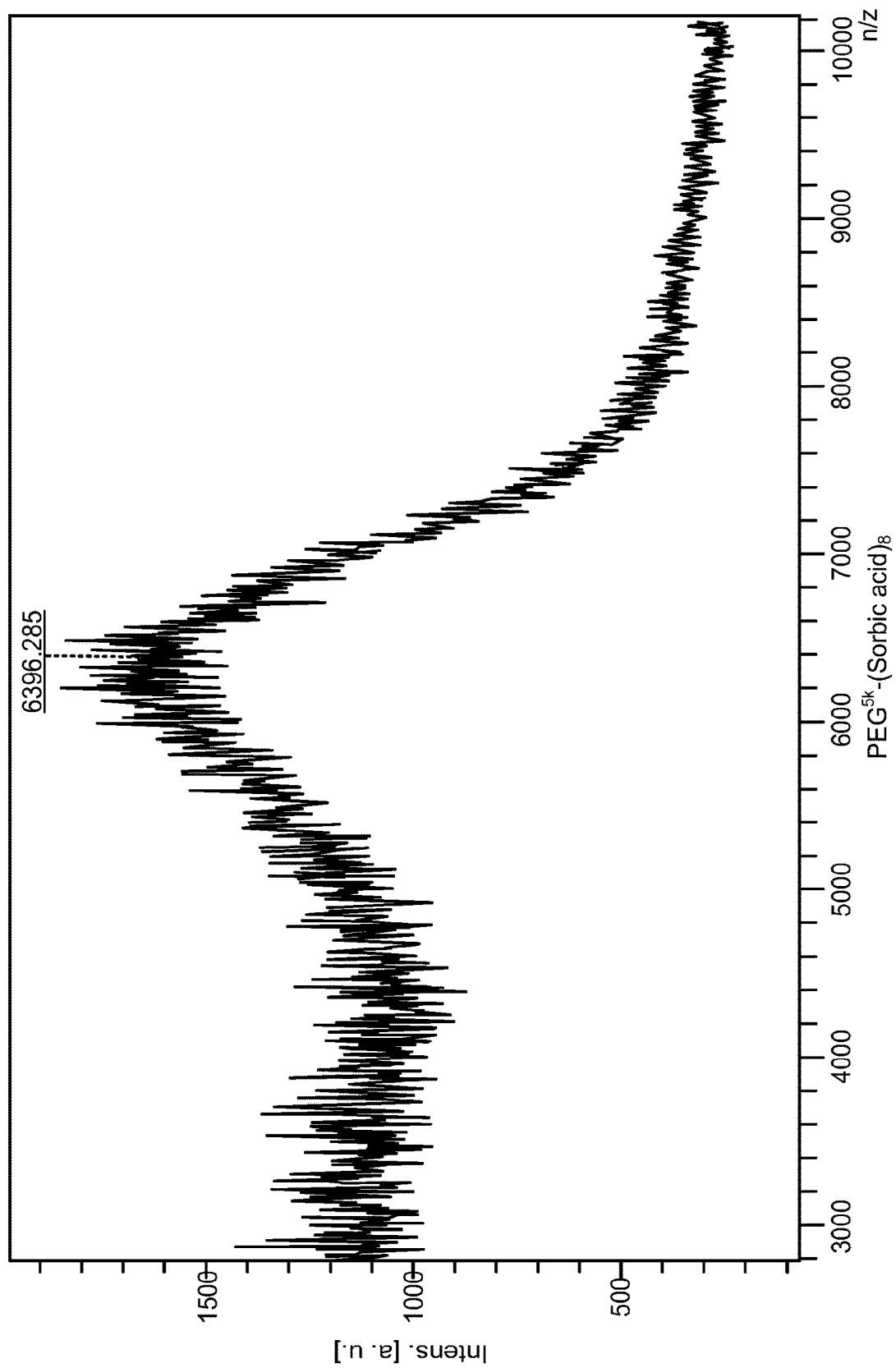
FIG. 10 illustrates MALDI-TOF MS data for non-hybrid telodendrimer PEG$^{5k}$-(sorbic acid)$_8$.

Empty nanoparticles assembled from hybrid TDs were evaluated for their cytotoxicity against human breast cancer cells MDA-MB-231 using MTS assay. As shown in FIG. 4, the nanocarriers did not exhibit detectable cytotoxicity up to at least 2 mg/ml for incubation over 48 h or 72 h, except for PEG$^{5K}$-(Glycocholic acid)$_8$, which showed some toxicity at 72 h time point. Lack of cytotoxicity from these micelles indicates their potential usage as drug carrier for nanoformulation.

Over the past several years we have successfully loaded a number of hydrophobic drugs (PTX, doxoruicin, vincristine, daunorubicin etc.) in our standard nanomicelles assembled from PEG$^{5K}$-CA$_8$ and these nano-formulations were proven to be efficacious in several xenograft models. However, we have also found PEG$^{5K}$-CA$_8$ does not work for all hydrophobic drugs such as DTX (Table 3, entry 1), CTX (Table 5, entry 1), or SN-38 (data not shown). In order to show versatility and flexibility of our nanomicelles, we evaluated a small set of polymers for their ability to encapsulate DTX (Table 3 & 4) and CTX (Table 5 & 6).

As shown in Table 3, loading efficiency of the standard TD PEG$^{5K}$-CA$_8$ for DTX at 10% drug:polymer ratio (w/w) was found to be 68.9%. At the very same drug:polymer ratio, six different hybrid TDs were found to have higher drug loading capacity than that of PEG$^1$K-CA$_8$ (entry 2, 3, 6, 7, 8 and 11). Among the PEG$^{5K}$-CA$_8$ class, PEG$^{5K}$-(Glycocholic acid)$_8$ has better loading efficiency than that of standard TD. Other than PEG$^{5K}$-(Octanoic acid)$_4$/CA$_4$ (entry 8), all other favorable candidates had particle size <20 nm with narrow size distribution. Moreover three of them viz. 3 (PEG$^{5K}$-(Cinnamic acid)$_4$/CA$_4$), 6 (PEG$^{5K}$-(Lipoic acid)$_4$/CA$_4$) and 11 (PEG$^{5K}$-(Sorbic acid)$_4$/CA$_4$) encapsulated DTX with 100% efficiency. These three polymers were selected for loading at higher drug concentration (Table 4). At DTX loading of 3 mg/15 mg polymer, both 3 and 6 still retained the higher drug loading (93.3 and 88.4% respectively), but loading efficiency of 11 was found to drop to 56.7%. Based on the DTX screening, we identified two polymers, 3 and 6, that can stably encapsulate DTX at high loading capacity (nearly 20% w/w) without any visual precipitate; stability was monitored by DLS (data not shown).

TABLE 3

DTX loading (1.5 mg/15 mg polymer)

| Entry | Polymer | Particle size (volume %, width) | Drug/polymer (w/w) % | Loading efficiency |
|---|---|---|---|---|
| 1 | PEG$^{5K}$-CA$_8$ | 13.3 (100, 8.01) nm | 10 | 68.9 |
| 2 | PEG$^{5K}$-Biotin$_4$/CA$_4$ | 10.5 (100, 7.91) nm | 10 | 73.9 |
| 3 | PEG$^{5K}$-(Cinnamic acid)$_4$/CA$_4$ | 12.9 (100, 7.88) nm | 10 | 100 |
| 4 | PEG$^{5K}$-(Lauric acid)$_4$/CA$_4$ | 19.6 (95, 16.67) nm/ 295.4 (5, 312) nm | 10 | 0 |
| 5 | PEG$^{5K}$-(Linoleic acid)$_4$/CA$_4$ | 9.35 (100, 7.78) nm | 10 | Precipitated |
| 6 | PEG$^{5K}$-(Lipoic acid)$_4$/CA$_4$ | 11.8 (100, 10.3) nm | 10 | 100 |
| 7 | PEG$^{5K}$-(Nicotinic acid)$_4$/CA$_4$ | 10.8 (100, 8.3) nm | 10 | 76.7 |
| 8 | PEG$^{5K}$-(Octanoic acid)$_4$/CA$_4$ | 13.6 (95.1, 12.53) nm/ 122.8 (4.9, 206.5) nm | 10 | 90.1 |
| 9 | PEG$^{5K}$-(Oleic acid)$_4$/CA$_4$ | 13 (100, 10.33) nm | 10 | 2.2 |
| 10 | PEG$^{5K}$-(Retinoic acid)$_4$/CA$_4$ | 12.4 (93.9, 9.65) nm/ 338 (6.1, 226.5) nm | 10 | 61.5 |
| 11 | PEG$^{5K}$-(Sorbic acid)$_4$/CA$_4$ | 12.3 (100, 7.67) nm | 10 | 100 |
| 12 | PEG$^{5K}$-(Biotin)$_8$ | 11 (95.9, 9.42) nm/ 1087 (4.1, 2586) nm | 10 | 20.9 |
| 13 | PEG$^{5K}$-(Chenodeoxycholic acid)$_8$ | 16.1 (100, 9.07) nm | 10 | 1.5 |
| 14 | PEG$^{5K}$-(Glycocholic acid)$_8$ | 19.7 (100, 8.88) nm | 10 | 85 |
| 15 | PEG$^{5K}$-(Nicotinic acid)$_8$ | 6.5 (19.8, 2) nm/ 11.3 (24.2, 5.4) nm/ 33.6 (50.5, 27.8) nm/ 173.6 (5.5, 109.9) nm | 10 | 18.1 |

TABLE 4

DTX loading (3 mg/15 mg polymer)

| Polymer | 3 mg DTX Drug/polymer (w/w) % | Loading efficiency % |
|---|---|---|
| PEG$^{5K}$-(Cinnamic acid)$_4$/CA$_4$ | 20 | 93.3 |
| PEG$^{5K}$-(Lipoic acid)$_4$/CA$_4$ | 20 | 88.4 |
| PEG$^{5K}$-(Sorbic acid)$_4$/CA$_4$ | 20 | 56.7 |

Figure 11:
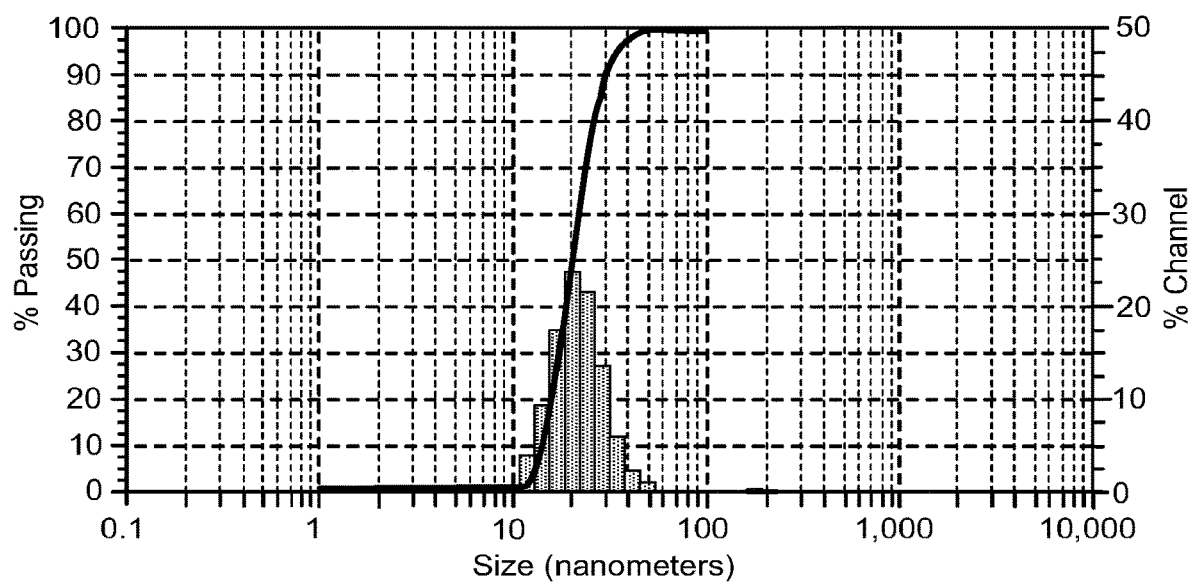
FIG. 11 illustrates particle sizes determined by dynamic light scattering (DLS) for representative indicated drug-loaded hybrid and non-hybrid telodendrimers.
Figure 12:
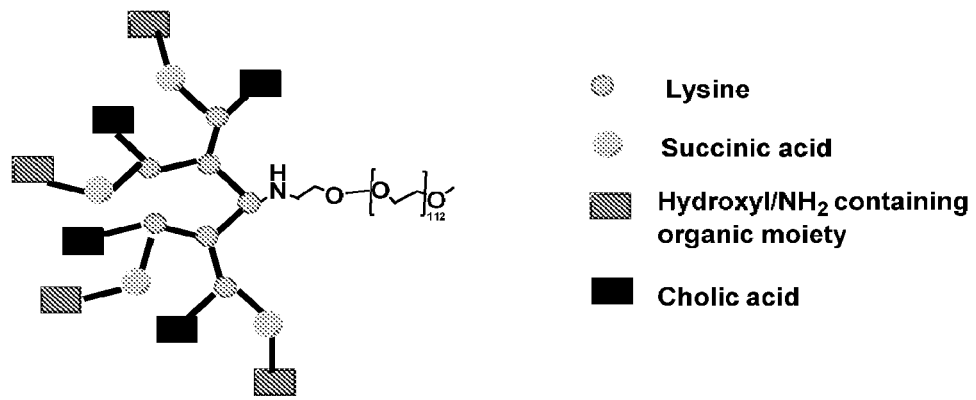
FIG. 12 illustrates one embodiment of a class of hybrid telodendrimer containing cholate (CA) and hydroxyl- or amine-containing containing end groups.
Figure 13:
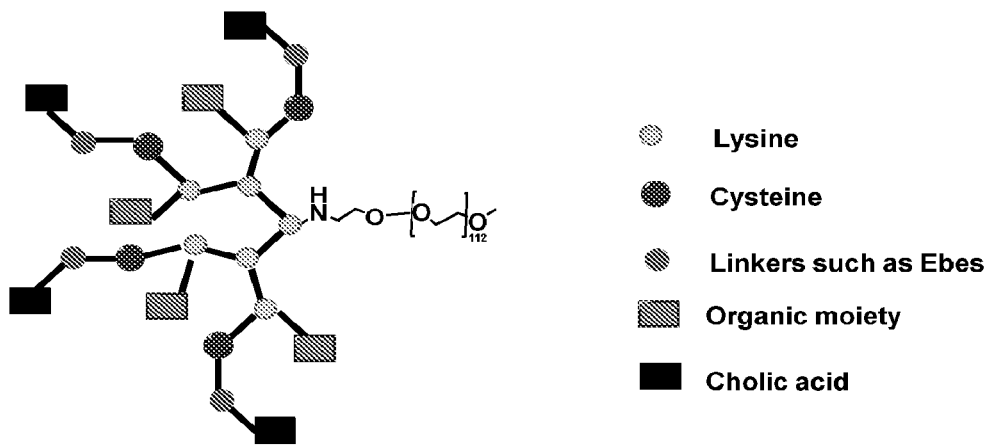
FIG. 13 illustrates one embodiment of a class of disulfide-based crosslinkable hybrid telodendrimers.
Figure 14:
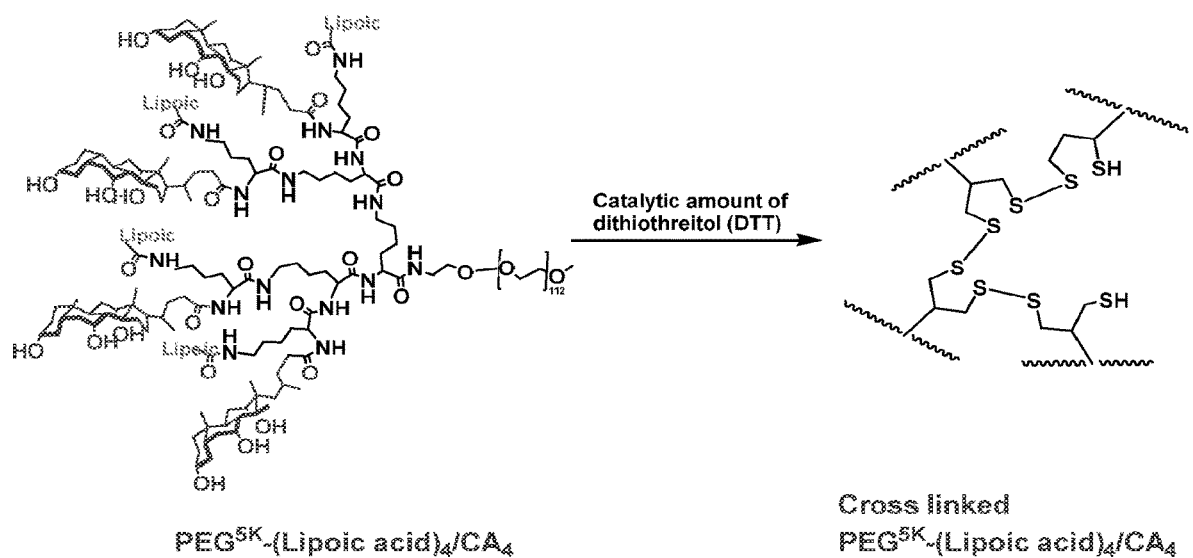
FIG. 14 (left) illustrates one embodiment of a class of lipoic acid based crosslinkable hybrid telodendrimers; (right) illustrates a reaction scheme for crosslinking three or more lipoic acid based crosslinkable hybrid telodendrimers.
Figure 15:
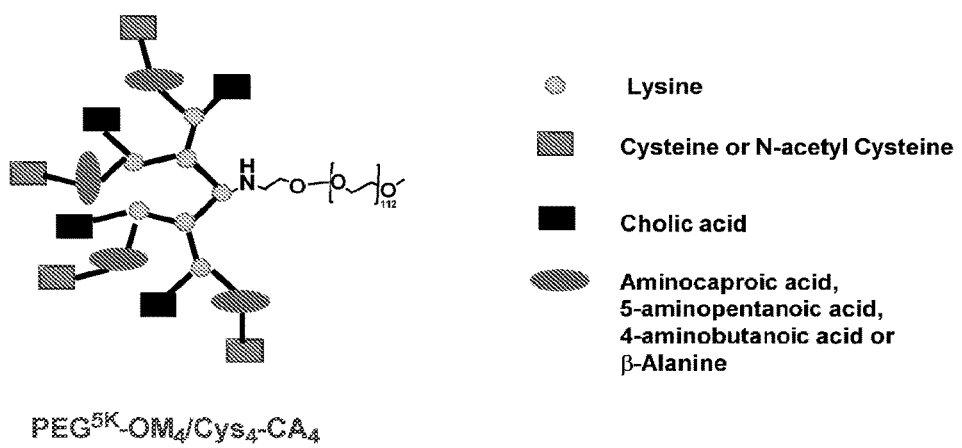
FIG. 15 illustrates one embodiment of a class of reduction sensitive disulfide-based hybrid telodendrimers.

CTX, another member of taxane family and recently approved for the treatment of prostate cancer was screened next. Compared to DTX, CTX had a better drug loading (entry 1, Table 5) in standard TD PEG$^{5K}$-CA$_8$ (79.5% at 2.0 mg of CTX compared to 68.9% at 1.5 mg of DTX per 15 mg of polymer). Despite better loading for CTX over DTX by PEG$^{5K}$-CA$_8$, broader size distribution of the final nanoparticles was observed in CTX. Compared to PEG$^{5K}$-CA$_8$, 4 other hybrid TDs viz. 3, 5, 6 and 8 showed better loading efficiency while PEG$^{5K}$-(Oleic acid)$_4$/CA4 (entry 9) showed similar loading efficiency. On the other hand none of the PEG$^{5K}$-OM$_8$ polymers showed better drug loading then PEG$^{5K}$-CA$_8$. PEG$^{5K}$-(Cinnamic acid)$_4$/CA$_4$ (entry 3) and PEG$^{5K}$-(Linoleic acid)$_4$/CA$_4$ (entry 5), both of which showed 100 percent loading efficiency, were tested further for higher drug loading. Both of these hybrid TDs were found to retain nearly 100% loading efficiency at 3 mg of drug and 15 mg of polymer (Table 5). Based on CTX screening, two polymers with a very high loading efficiency (nearly 20% w/w) were identified and loading was even better when compared to the results of DTX. For representative DLS data on drug loaded samples, see FIG. 11.

TABLE 5

CTX loading (2.0 mg/15 mg polymer)

| Entry | Polymer | Particle size (volume, %, width) | Drug/polymer (w/w) % | Loading efficiency |
|---|---|---|---|---|
| 1 | PEG$^{5K}$-CA$_8$ | 15.8 (96.2, 33) nm/ 348 (3.8, 1983) nm. | 13.35 | 79.5 |
| 2 | PEG$^{5K}$-Biotin$_4$/CA$_4$ | 23.9 (100, 28.9) nm | 13.35 | 56.5 |
| 3 | PEG$^{5K}$-(Cinnamic acid)$_4$/CA$_4$ | 15.9 (95.3, 7.13) nm/ 222.9 (4.7, 304) nm | 13.35 | 100 |

TABLE 5-continued

CTX loading (2.0 mg/15 mg polymer)

| Entry | Polymer | Particle size (volume, %, width) | Drug/polymer (w/w) % | Loading efficiency |
|---|---|---|---|---|
| 4 | PEG$^{5K}$-(Lauric acid)$_4$/CA$_4$ | 16.9 (15.4, 4.2) nm/ 49.8 (84.6, 74.4) nm | 13.35 | 38 |
| 5 | PEG$^{5K}$-(Linoleic acid)$_4$/CA$_4$ | 20.73 (100, 12.15) | 13.35 | 100 |
| 6 | PEG$^{5K}$-(Lipoic acid)$_4$/CA$_4$ | 0.99 (31, 0.22) nm/ 15.38 (69, 11.87) nm | 13.35 | 89.5 |
| 7 | PEG$^{5K}$-(Nicotinic acid)$_4$/CA$_4$ | 11.87 (100, 10.6) | 13.35 | 41.5 |
| 8 | PEG$^{5K}$-(Octanoic acid)$_4$/CA$_4$ | 18.0 (100, 14.4) | 13.35 | 82 |
| 9 | PEG$^{5K}$-(Oleic acid)$_4$/CA$_4$ | 25.27 (100, 69.9) nm | 13.35 | 80 |
| 10 | PEG$^{5K}$-(Retinoic acid)$_4$/CA$_4$ | 23.3 (100, 24.0) nm | 13.35 | 66 |
| 11 | PEG$^{5K}$-(Sorbic acid)$_4$/CA$_4$ | 16.2 (100, 10.0) nm | 13.35 | 74 |
| 12 | PEG$^{5K}$-(Biotin)$_8$ | 27.9 (95.3, 56.1) nm/ 1399 (4.7, 1193) nm | 13.35 | 31 |
| 13 | PEG$^{5K}$-(Chenodeoxycholic acid)$_8$ | 23.98 (100, 27.6) nm | 13.35 | 70 |
| 14 | PEG$^{5K}$-(Glycocholic acid)$_8$ | 0.96 (100, 0.21) nm | 13.35 | 55 |
| 15 | PEG$^{5K}$-(Nicotinic acid)$_8$ | 84.4 (94.6, 70) nm/ 396 (5.4, 229.4) nm | 13.35 | 69 |

TABLE 6

CTXloading (3 mg/15 mg polymer)

3 mg CTX

| Polymer | Drug/polymer (w/w) % | Loading efficiency % |
|---|---|---|
| PEG$^{5K}$-(Cinnamic acid)$_4$/CA$_4$ | 20 | 92 |
| PEG$^{5K}$-(Linoleic acid)$_4$/CA$_4$ | 20 | 97 |

Example 2: Additional Organic Moiety Hybrid Telodendrimers

Additional hybrid telodendrimers are proposed for carboxyl-containing organic moieties (OMs). Table 7 shows five such hybrid telodendrimers.

TABLE 7

Hybrid telodendrimers for carboxyl containing organic moiety (OM)

| Entry | OM | Polymer |
|---|---|---|
| 16 | Piromidic Acid (antibiotic) | PEG$^{5K}$-(Piromidic Acid$_4$)/CA$_4$ |
| 17 | Caffeic acid (present in coffee) | PEG$^{5K}$-(Caffeic acid$_4$)/CA$_4$ |
| 18 | Ricinoleic acid (castor oil) | PEG$^{5K}$-(Ricinoleic acid$_4$)/CA$_4$ |
| 19 | Pantothenic acid (Vitamin B5) | PEG$^{5K}$-(Pantothenic acid$_4$)/CA$_4$ |
| 20 | Aminocaproic acid (FDA approved drug) | PEG$^{5K}$-(Aminocaproic acid$_4$)/CA$_4$ |

Entry 17 was synthesized and characterized by mass spectrometry and dynamic light scattering (DLS). The results are as follows:

Molecular weight (Da; Theo): 8161

Molecular weight (Da; Exp): 8134

Particle size (volume %, width): 15.6 (100, 8.1) nm.

Example 3: Lipid Profile of Paclitaxel Loaded Nanocarriers of Organic Moiety Hybrid Telodendrimers Select telodendrimers were used to nanoformulate paclitaxel. The resulting nanocarrier-encapsulated drugs were injected intravenously into Balb/C mice at a dose of 10 mg/Kg of loaded paclitaxel and 200 mg/kg polymer. Blood was drawn at 8 h and 24 hr post-injection and serum samples were tested for lipid panel. The blood sample was analyzed to generate a lipid profile. At 8 hr post-injection, all polymers except for PEG$^{5K}$-(Linoleic acid)$_4$/CA$_4$ increased cholesterol and triglyceride levels. At 24 hours, both cholesterol and triglyceride levels decreased to near normal levels for most polymers, except PEG$^{5K}$-Cys$_4$-Ebes$_4$-CA$_8$, which remained 6-fold above the normal range. LDL levels increased in most of the polymers except for linoleic and disulfide crosslinked polymer (PEG$^{5K}$-Cys$_4$-Ebes$_4$-CA$_8$). The low lipid values for the porphyrin hybrid telodendrimer (PEG$^{5K}$-Por$_4$/CA$_4$) could be due to interference with the assay due to the absorbance of the porphyrin moieties at the assay wavelengths. The results are provided in Table 8:

TABLE 8

| Polymer | Post-Injection Time (hours) | Cholesterol (mg/dL) | HDL (mg/dL) | LDL (mg/dL) | NEFA (mEq/L) | TG (mg/dL) |
|---|---|---|---|---|---|---|
| PEG5K-CA$_8$ | 8 | 207.4 | 1.1 | ND | 0.6 | 1401.9 |
| PEG$^{5K}$-(Cinnamic acid)$_4$/CA$_4$ | 8 | 298.0 | 86.4 | 4.7 | 4.6 | 2252.2 |
| PEG$^{5K}$-Cys$_4$-Ebes$_4$-CA$_8$ | 8 | 323.4 | 144.8 | 2.9 | 3.5 | 3451.1 |
| PEG$^{5K}$-(Linoleic acid)$_4$/CA$_4$ | 8 | 116.3 | 20.0 | 11.2 | 1.7 | 233.6 |
| PEG$^{5K}$-(Lipoic acid)$_4$/CA$_4$ | 8 | 249.7 | 97.1 | 10.0 | 4.7 | 905.8 |
| PEG$^{5K}$-Por$_4$/CA$_4$ | 8 | 23.7 | 94.1 | ND | 1.1 | 41.9 |
| PBS | 8 | 105.6 | 99.5 | 4.3 | 1.4 | 40.3 |
| PEG5$^K$-CA$_8$ | 24 | 282.1 | 58.1 | 54.2 | 3.1 | 40.3 |
| PEG$^{5K}$-(Cinnamic acid)$_4$/CA$_4$ | 24 | 159.1 | 93.9 | 25.6 | 3.2 | 317.9 |
| PEG$^{5K}$-Cys$_4$-Ebes$_4$-CA$_8$ | 24 | 245.0 | 73.2 | 11.5 | 6.1 | 1953.7 |
| PEG$^{5K}$-(Linoleic acid)$_4$/CA$_4$ | 24 | 115.5 | 38.9 | 5.7 | 2.9 | 381.6 |
| PEG5$^K$-(Lipoic acid)$_4$/CA$_4$ | 24 | 148.8 | 99.4 | 32.5 | 3.2 | 271.6 |
| PEG$^{5K}$-Por$_4$/CA$_4$ | 24 | 73.5 | 99.5 | ND | 1.5 | 88.4 |

TABLE 8-continued

| Polymer | Post-Injection Time (hours) | Cholesterol (mg/dL) | HDL (mg/dL) | LDL (mg/dL) | NEFA (mEq/L) | TG (mg/dL) |
|---|---|---|---|---|---|---|
| PBS | 24 | 124.8 | 109.2 | 6.1 | 2.4 | 109.9 |
| Normal range | | 89.1-179.5 | 77.8-176 | 0.5-21.4 | 0.44-.82 | 57-293 |

ND: None Detected; NEFA: Non-esterified Fatty Acids; TG: triglycerides

Example 4: NSAID Hybrid Telodendrimers

Figure 21:
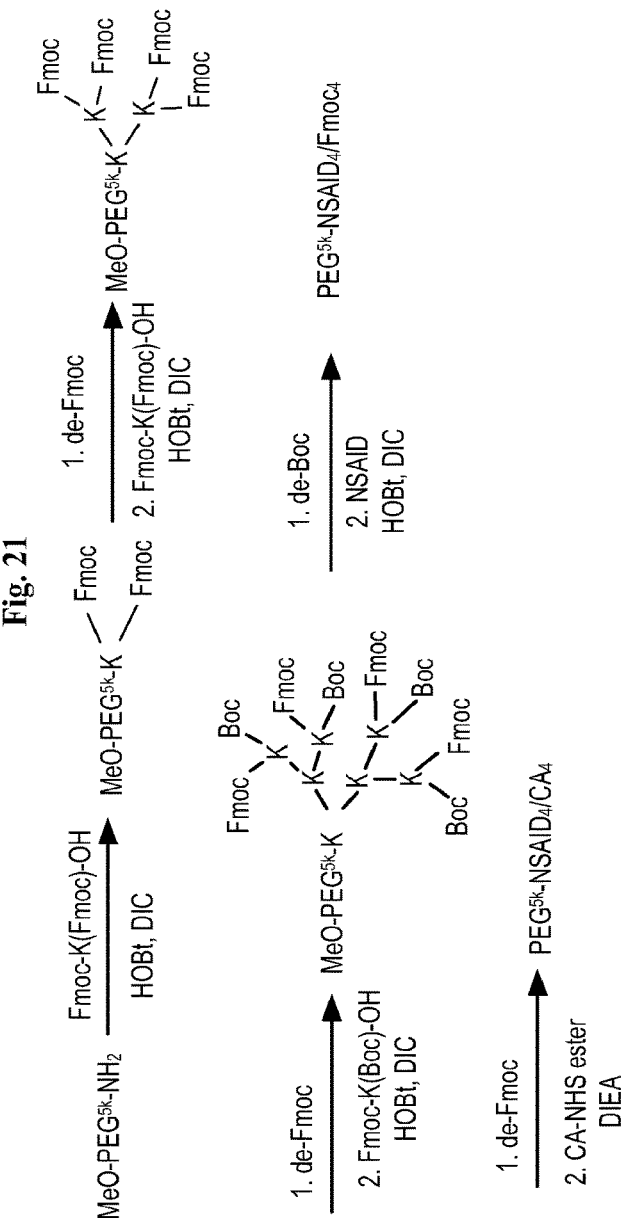
FIG. 21 illustrates preparation of NSAID hybrid telodendrimers.
Figure 22:
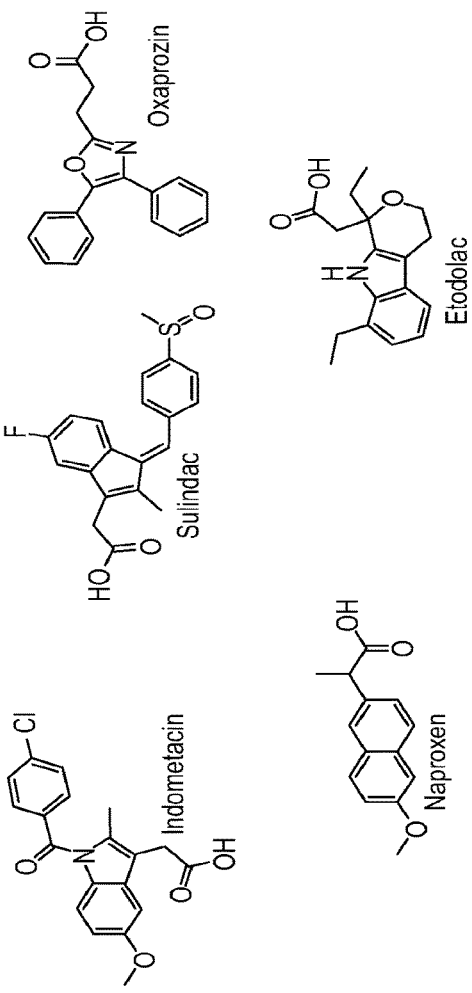
FIG. 22 illustrates NSAIDS useful in the present invention.
Figure 26:
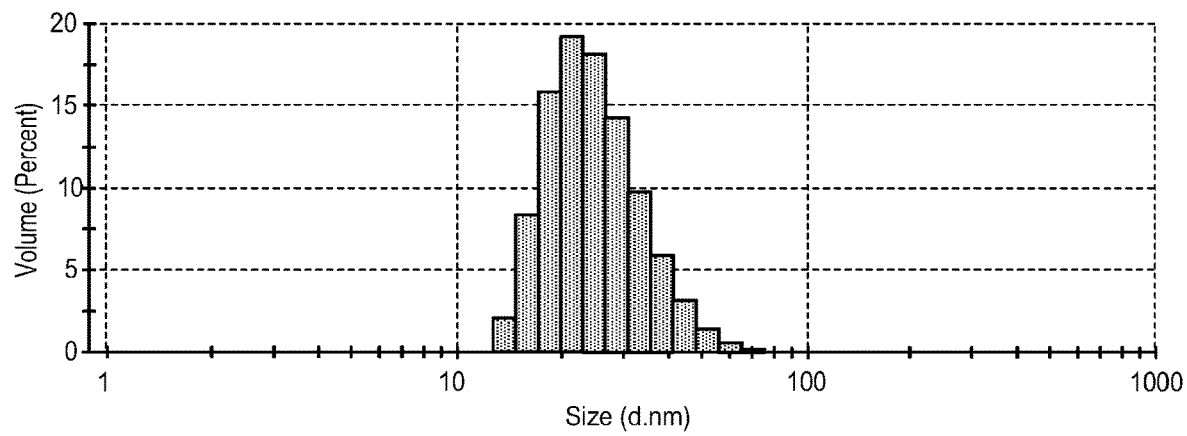
FIG. 26 illustrates the size distribution by volume for nanocarriers prepared using PEG$^{5K}$-(Oxaprozin)$_4$/(CA)$_4$.
Figure 27:
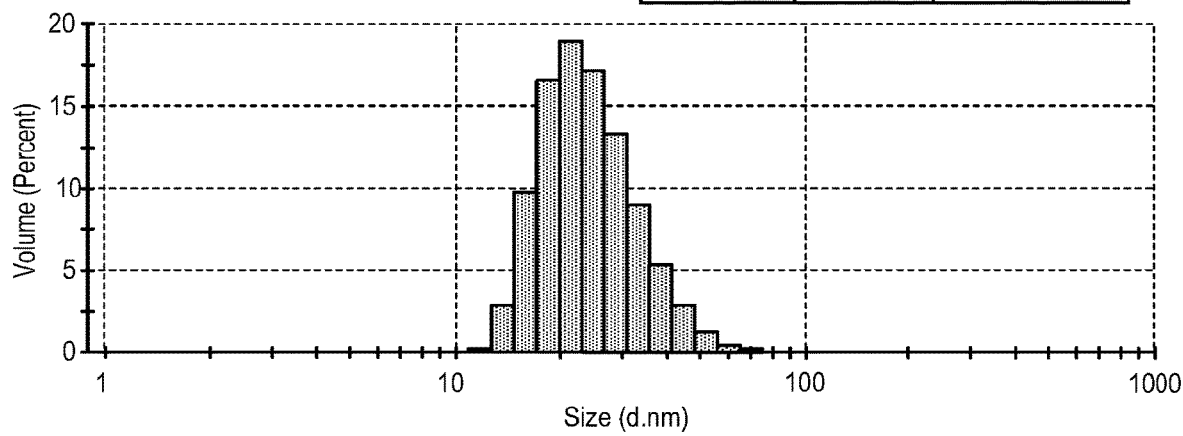
FIG. 27 illustrates the size distribution by volume for nanocarriers prepared using PEG$^{5K}$-(Sulindac)$_4$/(CA)$_4$.

Preparation of PEG$^{5K}$-(NSAID)$_4$/CA$_4$ telodendrimers was performed according to the scheme outlined in FIG. 21 using known methods and known NSAIDS (FIG. 22). Nanocarriers were also prepared from the corresponding telodendrimers. The molecular weight of the telodendrimers and and the particle size of the corresponding nanocarriers are provided in the table below.

| PEG$^{5K}$-(NSAIDs)$_4$/CA$_4$ | Molecular weight Exp (Theo) Da | Particle size |
|---|---|---|
| PEG5K-(Etodolac)$_4$/CA$_4$ | 8277 (8590) | Error! Reference source not found. |
| PEG$^{5K}$-(Indomethacin)$_4$/CA$_4$ | 8545 (8872) | Error! Reference source not found. |
| PEG$^{5K}$-(Naproxen)$_4$/CA$_4$ | 8153 (8362) | Error! Reference source not found. |
| PEG$^{5K}$-(Oxaprozin)$_4$/CA$_4$ | 8376 (8362) | Error! Reference source not found. |
| PEG$^{5K}$-(Sulindac)$_4$/CA$_4$ | 8600 (8866) | Error! Reference source not found. |

The nanocarriers were then loaded with niclosamide using the methods described above at 2 mg/20 mg polymer (n=1):

| Polymer | Particle size (volume %, width) nm | Drug/polymer (w/w) % | Loading efficiency % |
|---|---|---|---|
| PEG5K-(Etodolac)$_4$/CA$_4$ | 43.3 (100, 25.2) | 10 | ~80% |
| PEG$^{5K}$-(Indomethacin)$_4$/CA$_4$ | ND | 10 | 0 |
| PEG$^{5K}$-(Naproxen)$_4$/CA$_4$ | 44.8 (98.3, 35), 5364 (1.7, 684) | 10 | ~90 |
| PEG$^{5K}$-(Oxaprozin)$_4$/CA$_4$ | 31.5 (100, 19.6) | 10 | ~100 |
| PEG$^{5K}$-(Sulindac)$_4$/CA$_4$ | 39.3 (100, 35) | 10 | 100% |

ND: Not determined

Example 5: Cross-Linkable Organic Moiety Hybrid Telodendrimers

Figure 16:
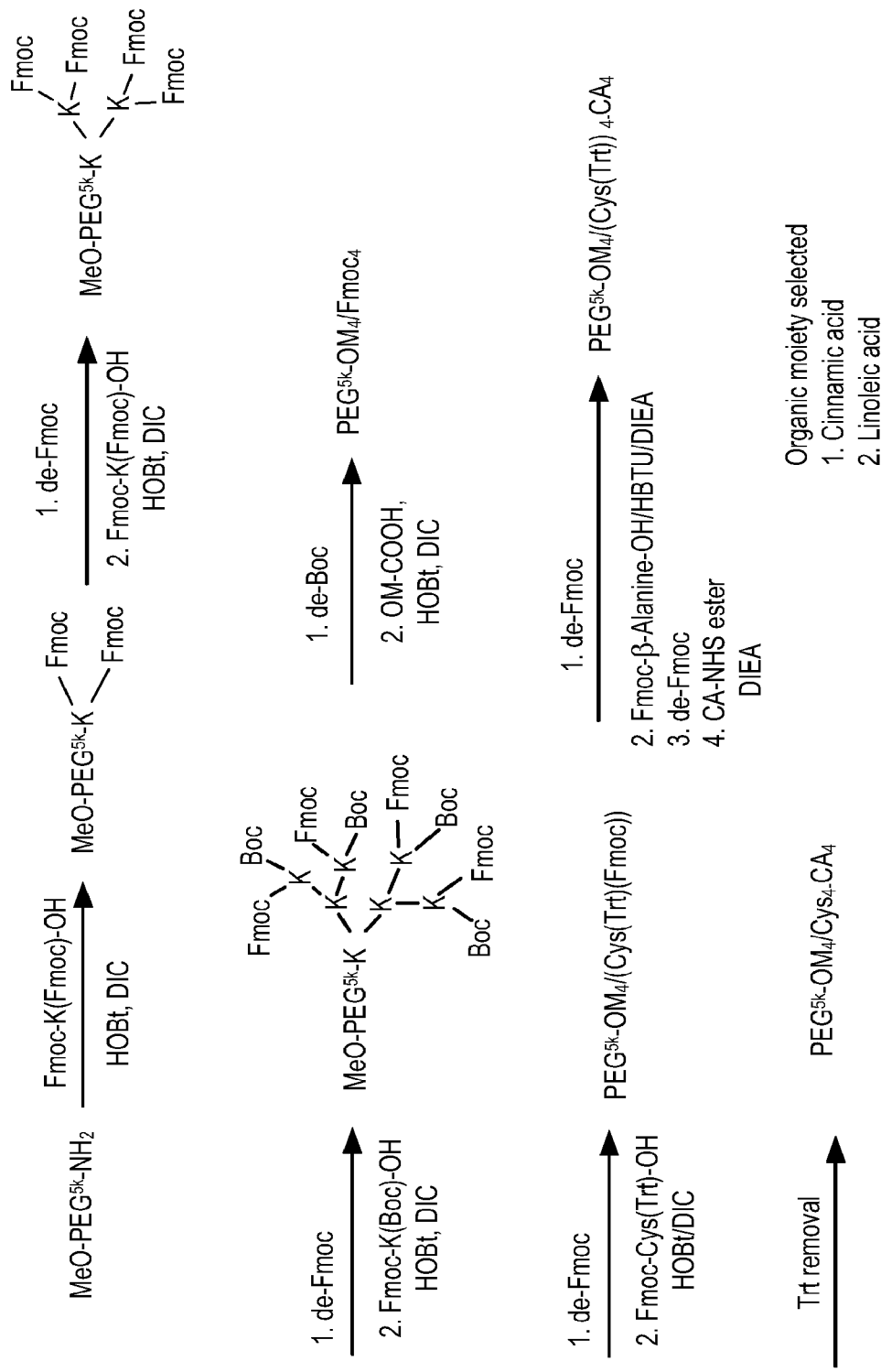
FIG. 16 illustrates Synthesis of disulfide cross linked polymers PEG5K-(cinnamic acid)4/(Cys-L-CA)4 and PEG5K-(linoleic acid)4/(Cys-L-CA)4 based on cinnamic- and linoleic acid respectively.
Figure 17:
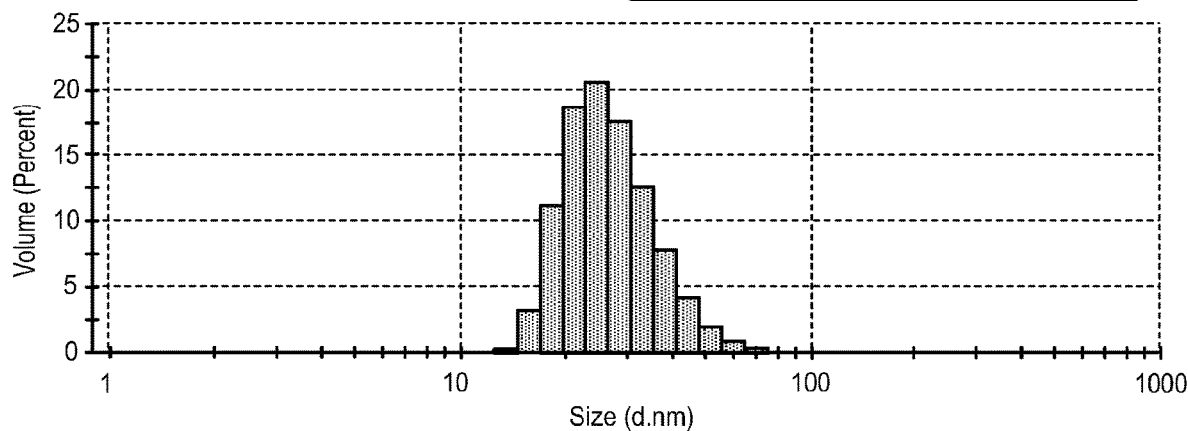
FIG. 17 illustrates the size distribution by volume for nanocarriers prepared using PEG$^{5K}$-(cinnamic acid)$_4$/(Cys-L-CA)$_4$.
Figure 18:
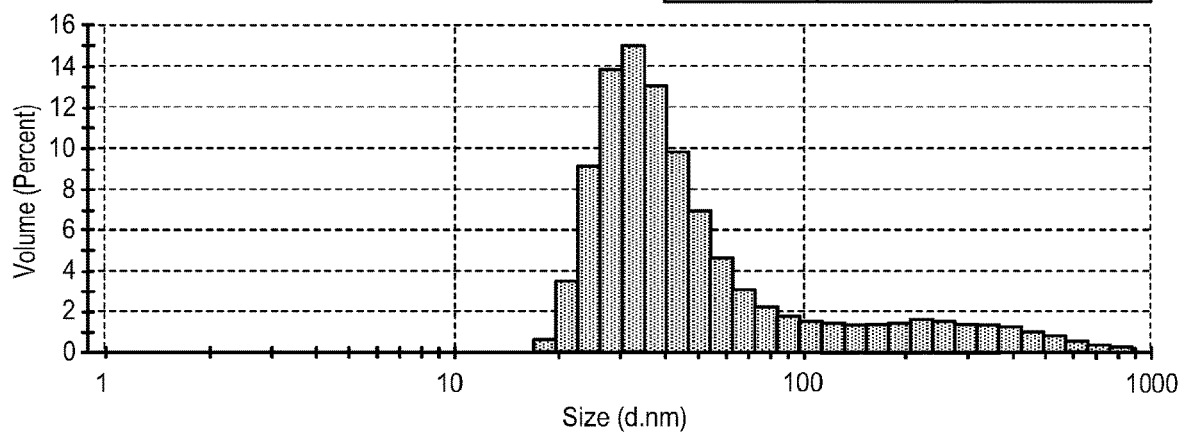
FIG. 18 illustrates the size distribution by volume for nanocarriers prepared using PEG$^{5K}$-(linoleic acid)$_4$/(Cys-L-CA)$_4$.

Preparation of PEG$^{5K}$-(Cinnamic Acid)$_4$/Cys$_4$-L-CA$_4$ and PEG$^{5K}$-(Linoleic Acid)$_4$/Cys$_4$-L-CA$_4$ was performed according to the scheme outlined in FIG. 16 using known methods.

| Polymer | Molecular weight Exp (Theo) in Da | Particle size |
|---|---|---|
| PEG$^{5K}$-(cinnamic acid)$_4$/(Cys-L-CA)$_4$ | 8061 (8761) | see Error! Reference source not found. |
| PEG$^{5K}$-(linoleic acid)$_4$/(Cys-L-CA)$_4$ | 8600 (9291) | see Error! Reference source not found. |

Figure 19:
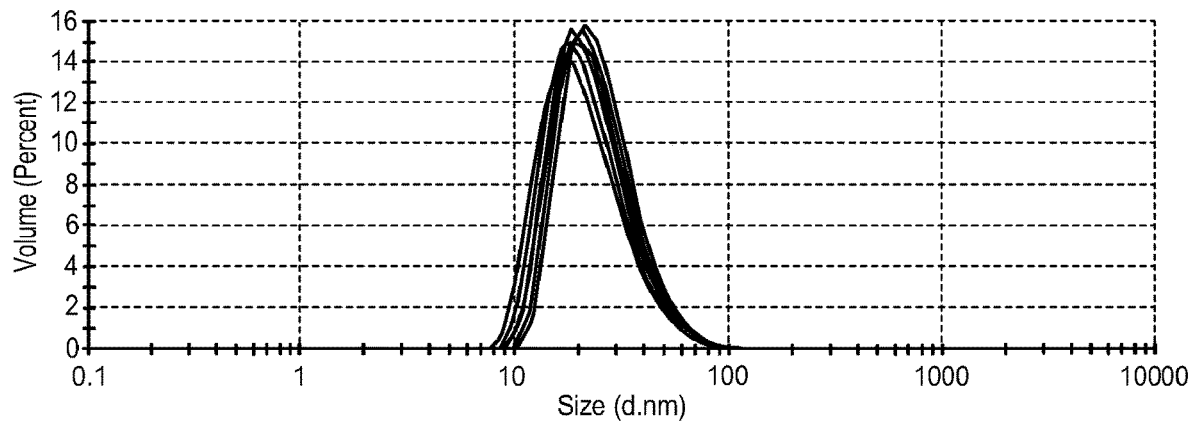
FIG. 19 illustrates the SDS stability study with PEG$^{5K}$-(linoleic acid)$_4$/(Cys-L-CA)$_4$.
Figure 20:
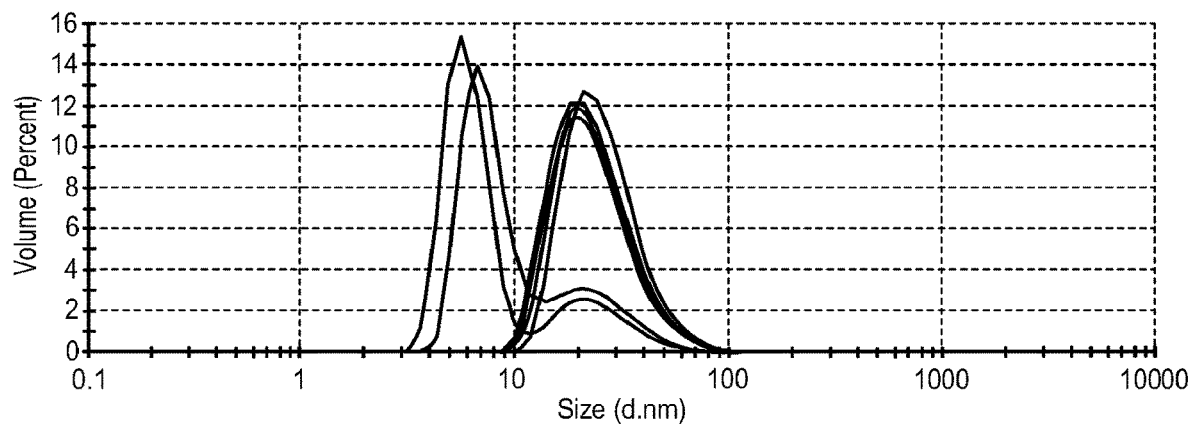
FIG. 20 illustrates the SDS stability study with PEG$^{5K}$-(linoleic acid)$_4$/(Cys-L-CA)$_4$ and DTT at 10 mM.

In presence of SDS, linoleic acid based cross-linked system retained the similar particle size indicating micellar stability under disruptive condition when observed for 45 mins. Surprisingly under similar conditions with 10 mM reducing agent added, cross-linked system still retained almost similar particle size with random fluctuation towards dissociative state (FIG. 19 and FIG. 20).

The crosslinked nanocarriers were then loaded with cabazitaxel (2 mg drug/15 mg polymer, n=1):

| Polymer | Drug | Drug/polymer (w/w) % | Loading efficiency % |
|---|---|---|---|
| PEG$^{5K}$-(cinnamic acid)$_4$/(Cys-L-CA)$_4$ | Cabazitaxel | 13.3 | 100 |
| PEG$^{5K}$-(linoleic acid)$_4$/(Cys-L-CA)$_4$ | Cabazitaxel | 13.3 | 100 |

Figure 28:
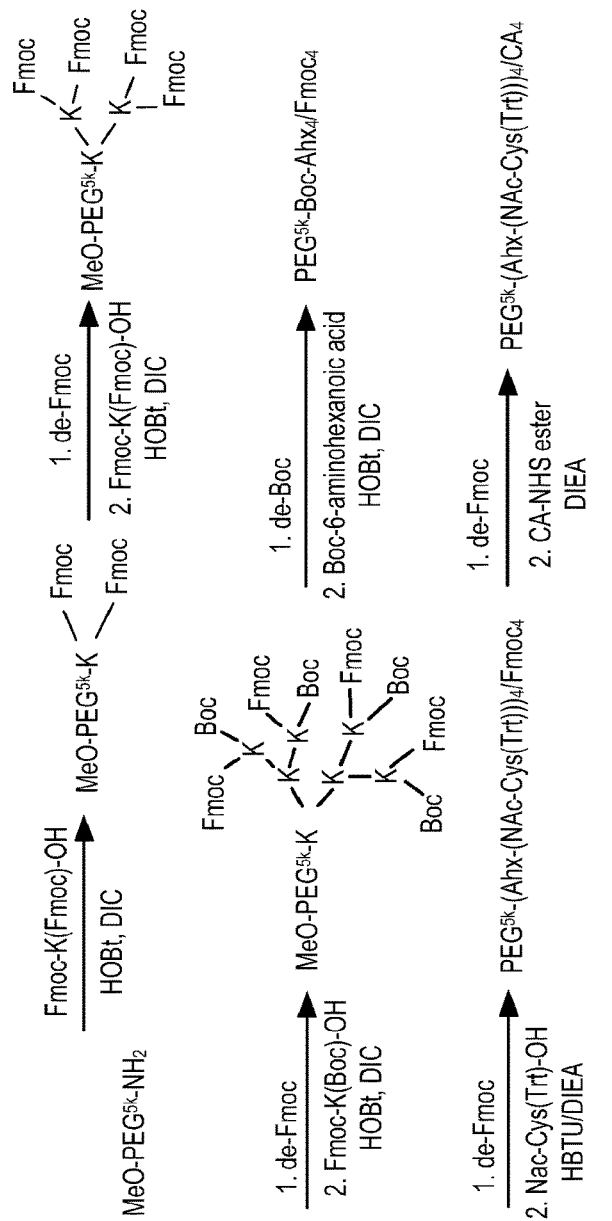
FIG. 28 illustrates preparation of the surface crosslinkable telodendrimers, such as PEG$^{5K}$-(Ahx-(NAc-Cys))$_4$/CA$_4$.
Figure 29:
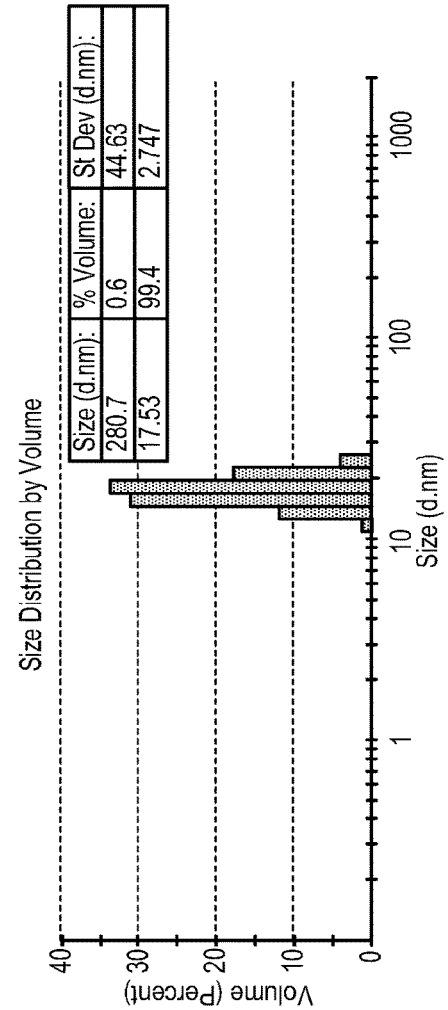
FIG. 29 illustrates the size distribution by volume for nanocarriers prepared using PEG$^{5K}$-(Ahx-(NAc-Cys))$_4$/CA$_4$.

Example 6: Preparation of Surface Crosslinkable Hybrid Telodendrimer PEG5K-(Ahx-(NAc-Cys))$_4$/CA$_4$ Preparation of PEG5K-(Ahx-(NAc-Cys))$_4$/CA$_4$ was performed according to the scheme outlined in FIG. 28 using known methods. These telodendrimers, having an experimental molecular weight of 8412 (compared to a theoretical molecular weight of 8544) were then used to prepare nanocarriers using the methods described above (see FIG. 29).

Figure 30:
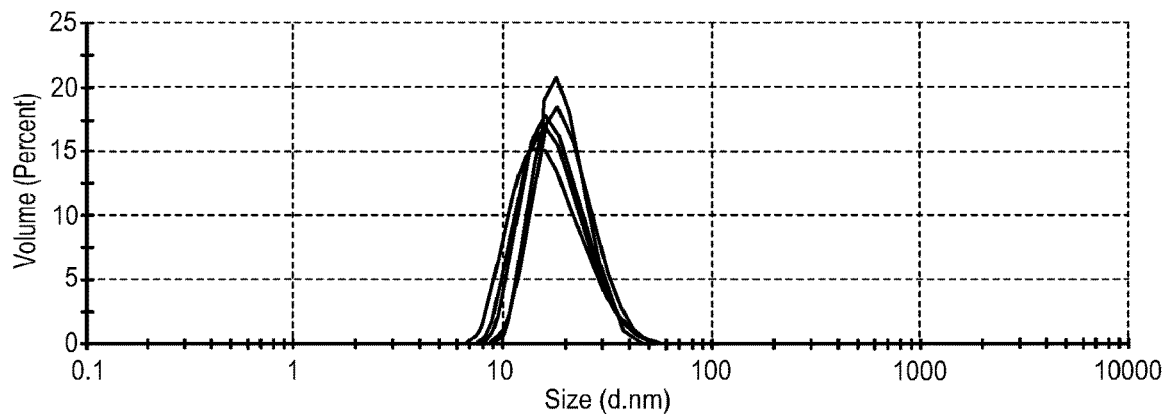
FIG. 30 illustrates the SDS stability study with PEG$^{5K}$-(Ahx-(NAc-Cys))$_4$/CA$_4$.
Figure 31:
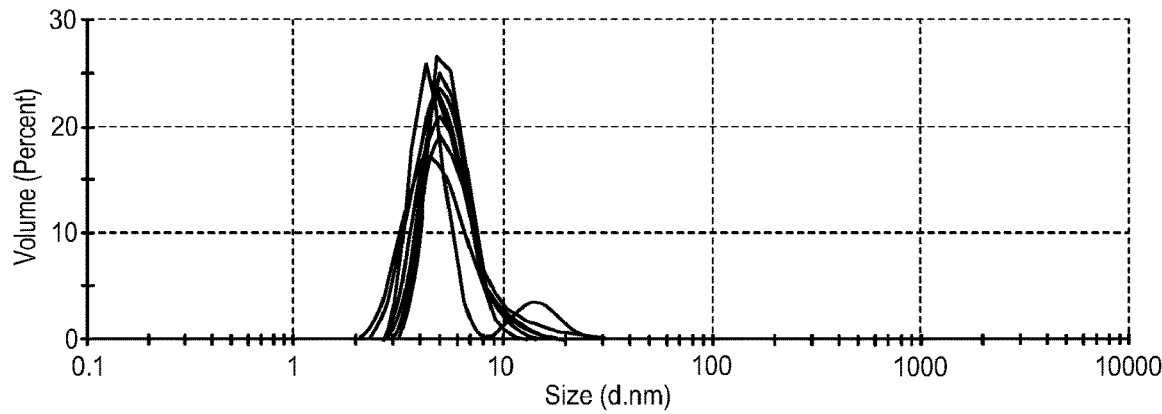
FIG. 31 illustrates the SDS stability study with PEG$^{5K}$-(Ahx-(NAc-Cys))$_4$/CA$_4$ and DTT at 10 mM.
Figure 32:
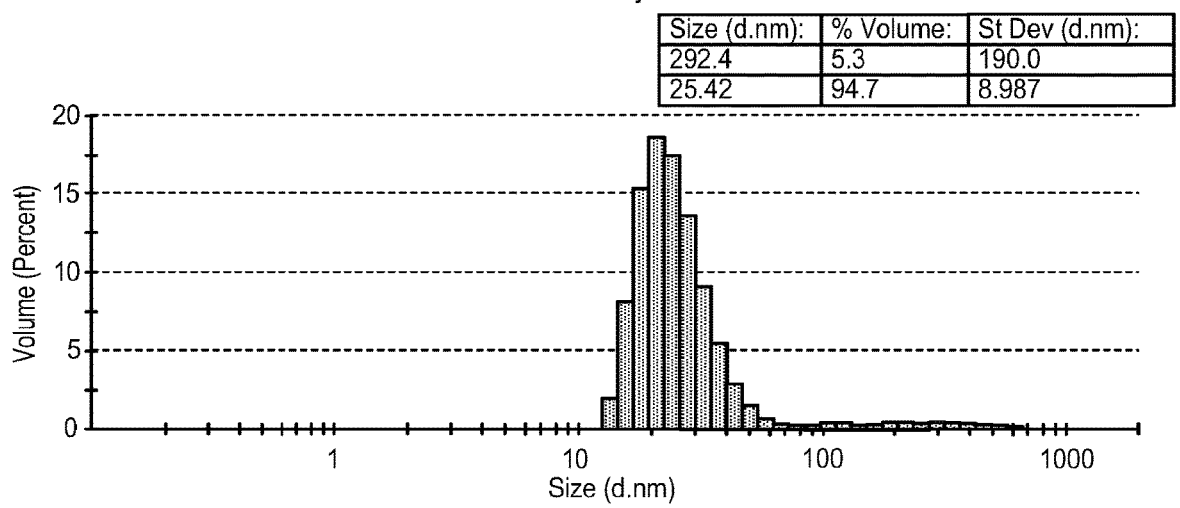
FIG. 32 illustrates the size distribution by volume for nanocarriers prepared using PEG$^{5K}$-(Ahx-(NAc-Cys))$_4$/CA$_4$ loaded with cabazitaxel.
Figure 33:
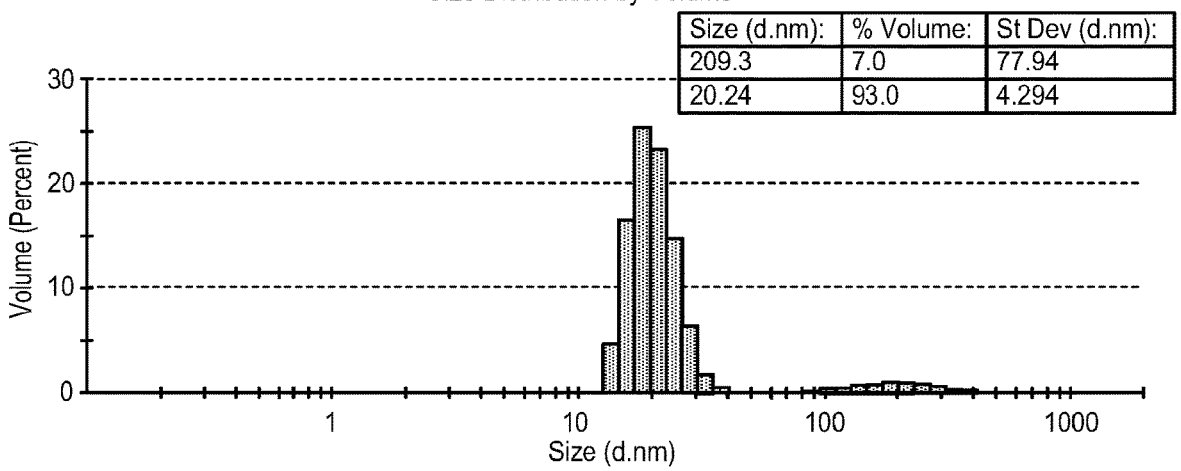
FIG. 33 illustrates the size distribution by volume for nanocarriers prepared using PEG$^{5K}$-(Ahx-(NAc-Cys))$_4$/CA$_4$ loaded with docetaxel.
Figure 34:
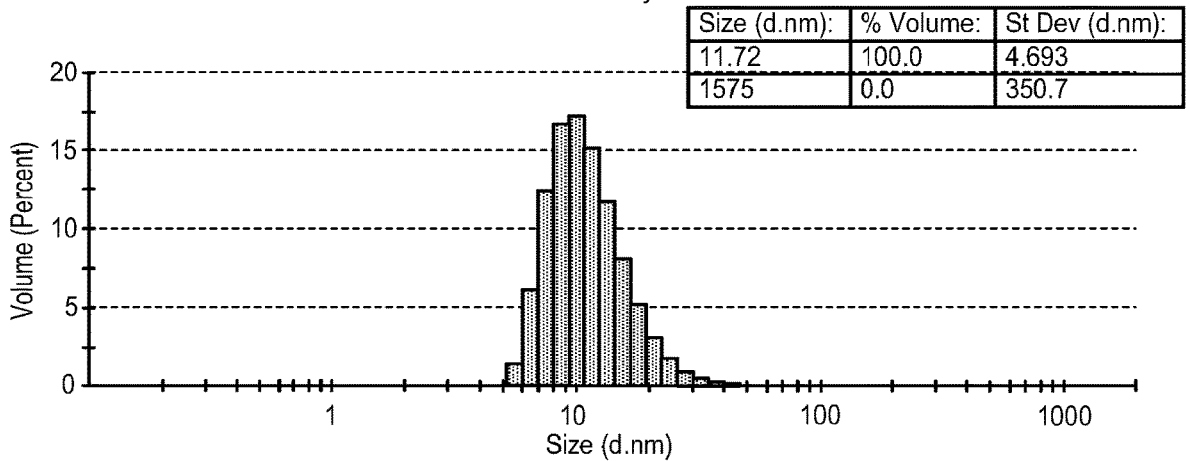
FIG. 34 illustrates the size distribution by volume for nanocarriers prepared using PEG$^{5K}$-(Ahx-(NAc-Cys))$_4$/CA$_4$ loaded with doxorubicin.
Figure 35:
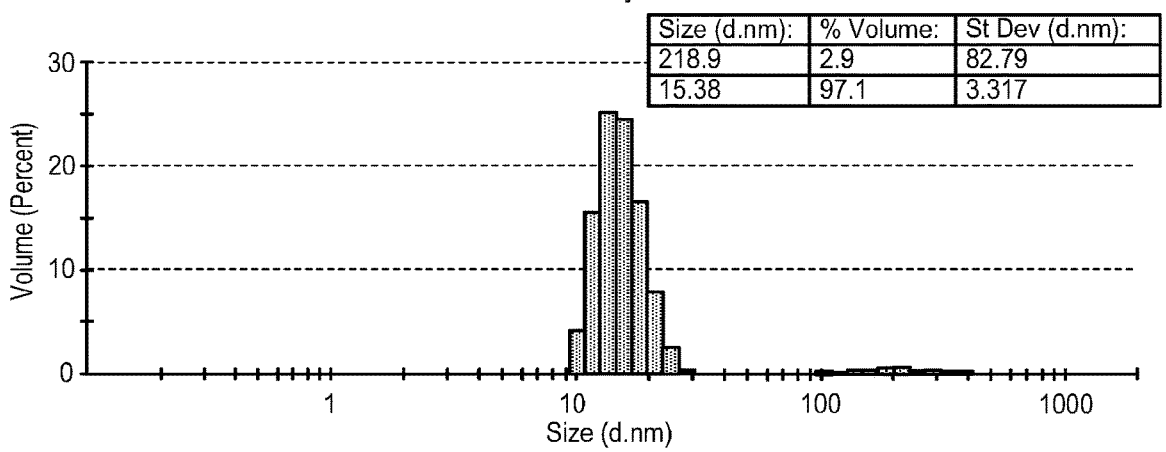
FIG. 35 illustrates the size distribution by volume for nanocarriers prepared using PEG$^{5K}$-(Ahx-(NAc-Cys))$_4$/CA$_4$ loaded with etoposide.
Figure 36:
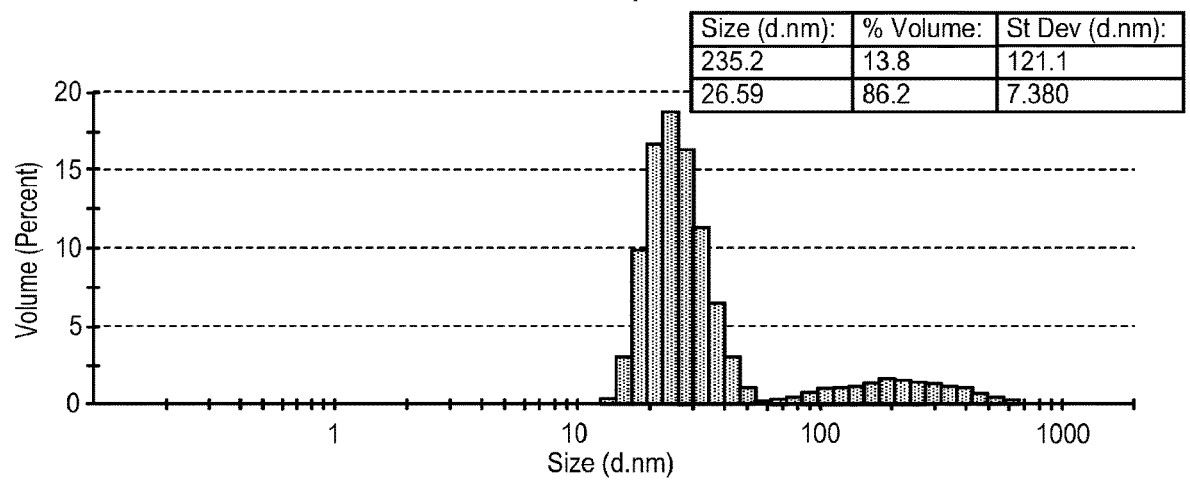
FIG. 36 illustrates the size distribution by volume for nanocarriers prepared using PEG$^{5K}$-(Ahx-(NAc-Cys))$_4$/CA$_4$ loaded with paclitaxel.
Figure 37:
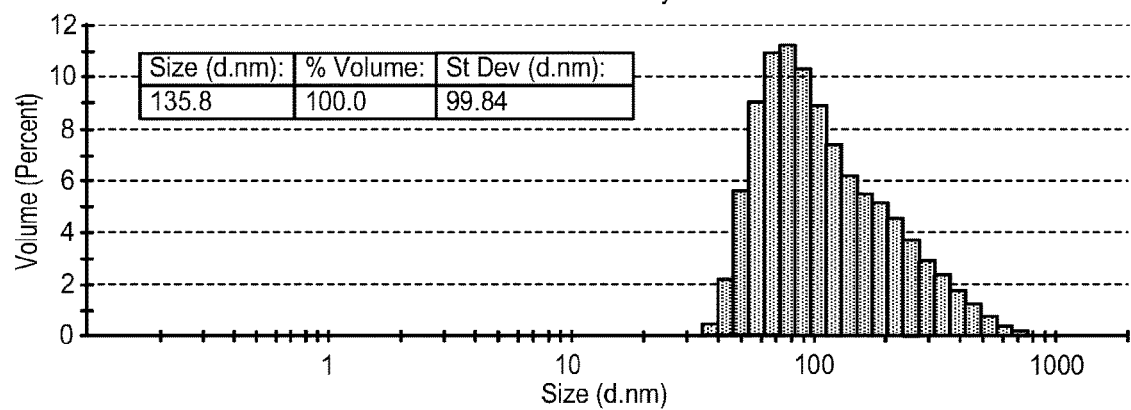
FIG. 37 illustrates the size distribution by volume for nanocarriers prepared using PEG$^{5K}$-(Ahx-(NAc-Cys))$_4$/CA$_4$ loaded with SN-38.
Figure 38:
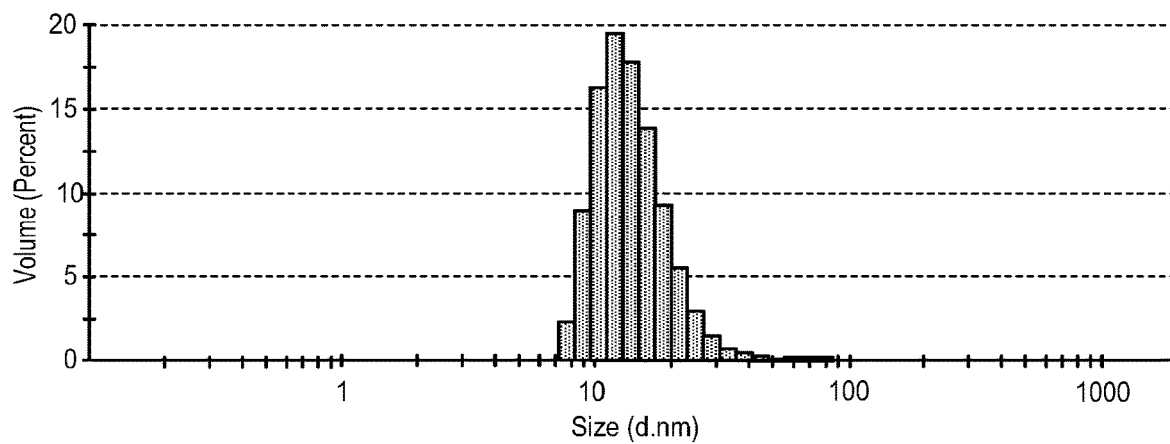
FIG. 38 illustrates the size distribution by volume for nanocarriers prepared using PEG$^{5K}$-(Ahx-(NAc-Cys))$_4$/CA$_4$ loaded with vinblastine.
Figure 39:
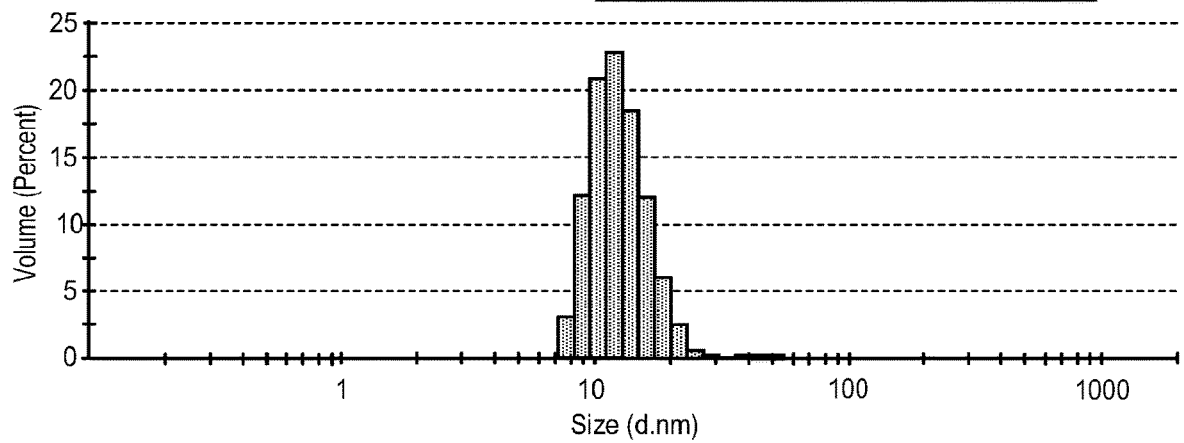
FIG. 39 illustrates the size distribution by volume for nanocarriers prepared using PEG$^{5K}$-(Ahx-(NAc-Cys))$_4$/CA$_4$ loaded with vincristine.

Additional SDS stability studies were also performed with and without DTT 10 mM (FIG. 30 and FIG. 31).

The crosslinked nanocarriers were then loaded with different drugs, as shown in the table below:

| Drug (amount)[a] | Polymer (amount)[a] | Observation | Particle size |
|---|---|---|---|
| Cabazitaxel (1 mg) | 10 mg | Clear solution | Error! Reference source not found. |
| Docetaxel (1 mg) | 10 mg | Clear solution | Error! Reference source not found. |
| Doxorubicin (1 mg) | 10 mg | Clear solution | Error! Reference source not found. |
| Etoposide (1 mg)[b] | 10 mg | Initially clear. On cross-linking yielded slightly cloudy solution | Error! Reference source not found. |
| Paclitaxel (1 mg) | 10 mg | Almost clear solution | Error! Reference source not found. |
| SN-38 (1 mg) | 10 mg | Huge precipitate | Error! Reference source not found. |
| Vinblastine (1 mg) | 10 mg | Clear | Error! Reference source not found. |
| Vincristine (1 mg)[b] | 10 mg | Tiny amount of precipitate | Error! Reference source not found. |

[a]Effective concentration 2 mg drug/20 mg polymer per ml PBS
[b]Repetition of drug loading was done at 1.5 mg/ml. Vincristine yielded clear solution but etoposide results similar to 2 mg data.

Figure 40:
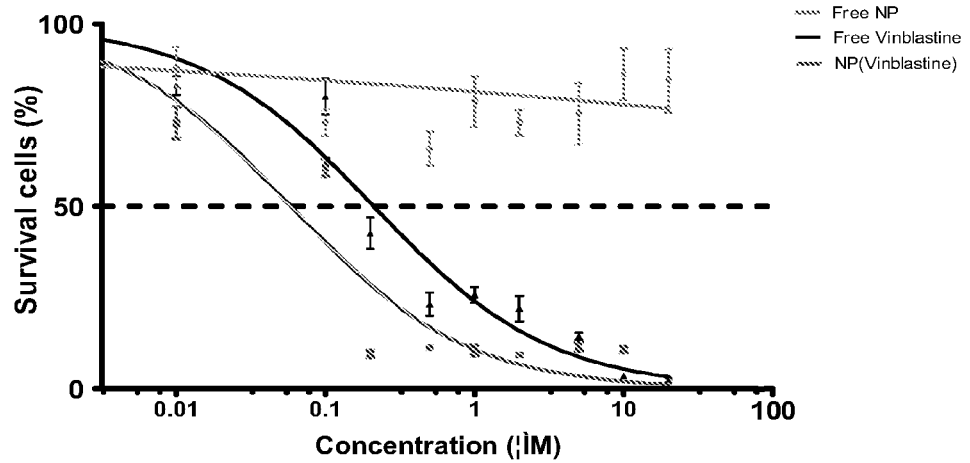
FIG. 40 illustrates the survival rate for bladder cancer cells (5637) exposed to nanocarriers prepared using PEG$^{5K}$-(Ahx-(NAc-Cys))$_4$/CA$_4$ and PEG$^{5K}$-(Ahx-(NAc-Cys))$_4$/CA4 loaded with vinblastine.
Figure 41:
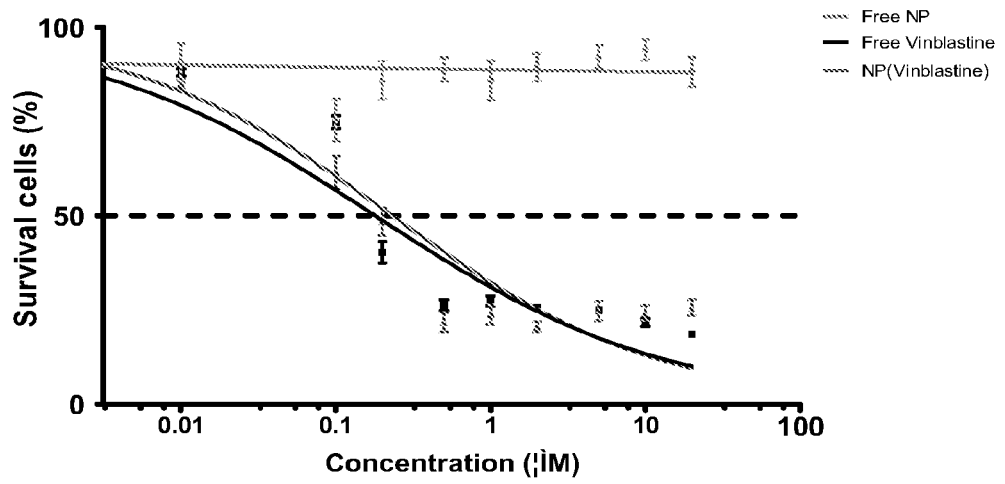
FIG. 41 illustrates the survival rate for bladder cancer cells (J82) exposed to nanocarriers prepared using PEG$^{5K}$-(Ahx-(NAc-Cys))$_4$/CA$_4$ and PEG$^{5K}$-(Ahx-(NAc-Cys))$_4$/CA4 loaded with vinblastine.
Figure 42:
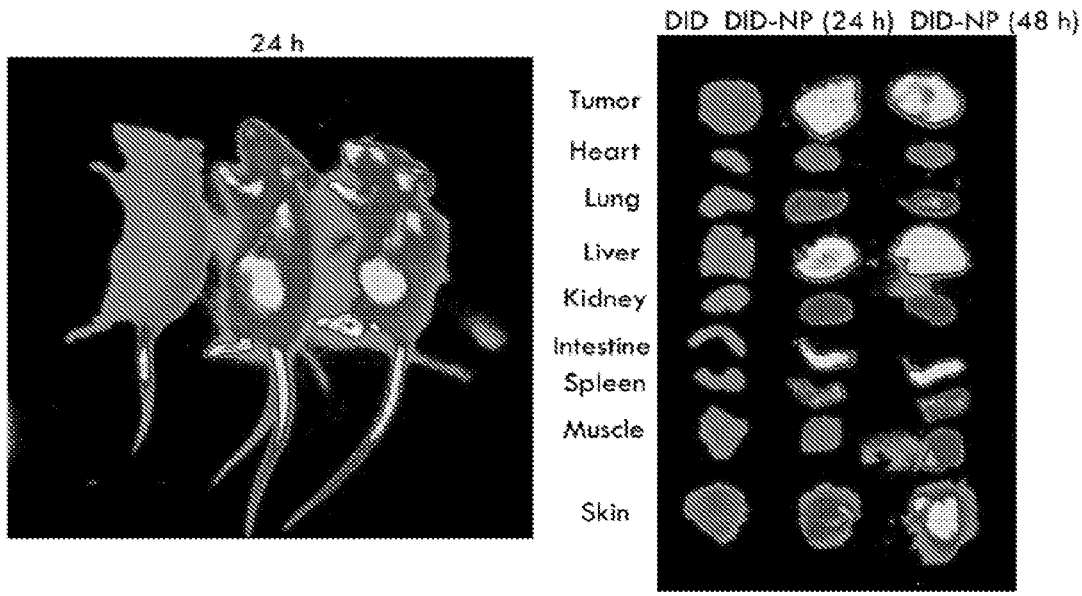
FIG. 42 illustrates the in vivo biodistribution of nanocarriers prepared using PEG$^{5K}$-(Ahx-(NAc-Cys))$_4$/CA$_4$ loaded with DiD.
Figure 43A:
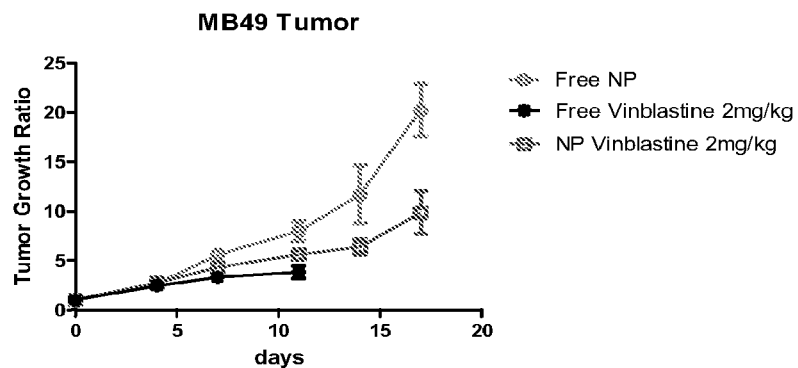
Figure 44B:
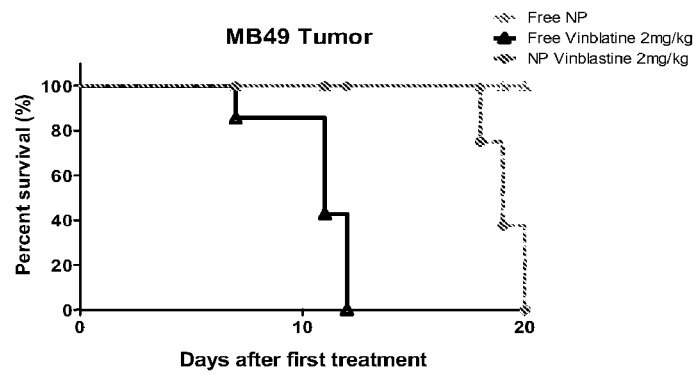
FIGS. 44A, 44B and 44C illustrate the results for an in vivo therapeutic study for a BL269 tumor using PEG$^{5K}$-(Ahx-(NAc-Cys))$_4$/CA$_4$ and PEG$^{5K}$-(Ahx-(NAc-Cys))$_4$/CA$_4$ loaded with vinblastine, and show tumor growth (FIG. 44A), survival curve (FIG. 44B) and body weight (FIG. 44C).
Figure 44C:
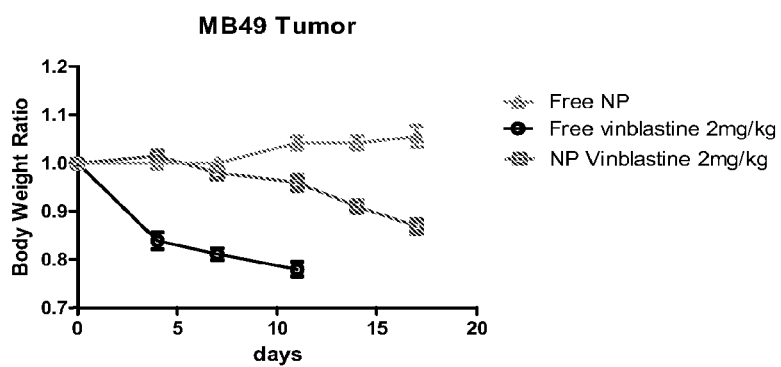
Figure 44A:
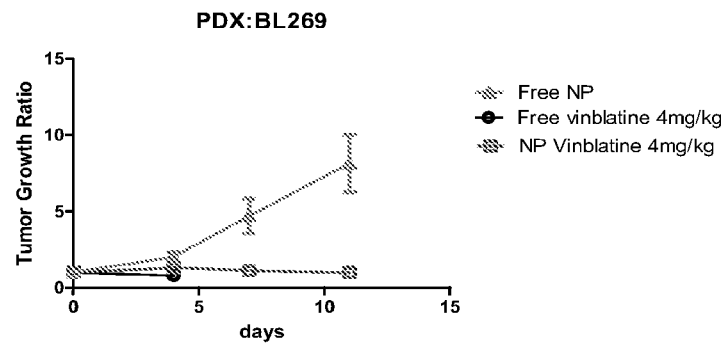
Figure 44B:
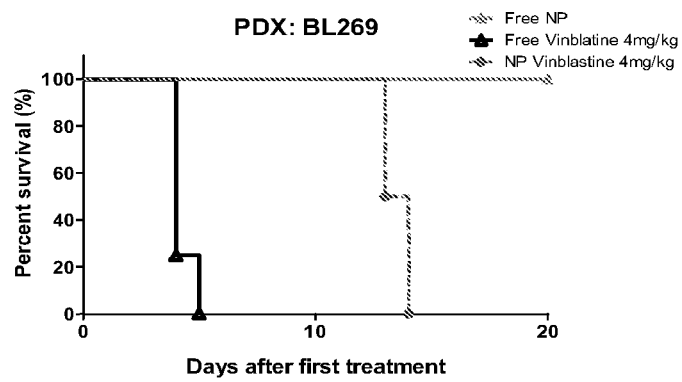
Figure 44C:
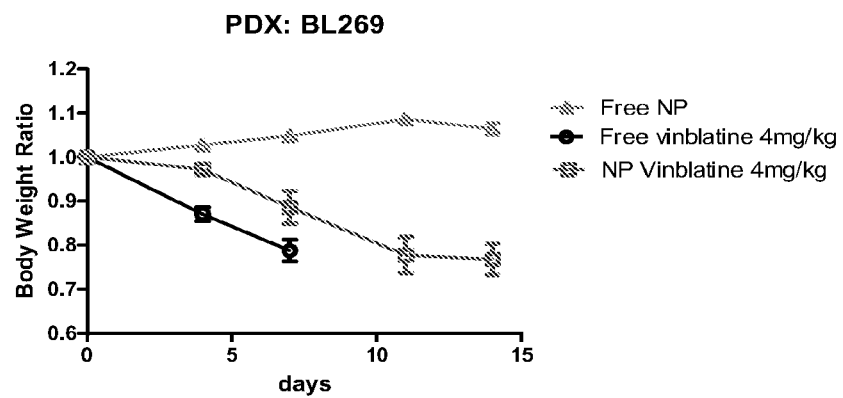

In vitro cytotoxicity of nanocarriers of PEG$^{5K}$-(Ahx-(NAc-Cys))$_4$/CA$_4$ loaded with vinblastine was then tested in bladder cancer cells 5637 (FIG. 40) and J82 (FIG. 41). The in vivo biodistribution of the nanocarriers loaded with DiD was also tested and is shown in FIG. 42. An in vivo therapeutic study was also performed using an MB49 tumor and a BL269 tumor.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the structure:

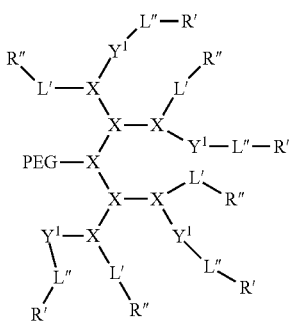

wherein
each L' and L" is independently a bond or a linker Ebes, aminocaproic acid, 5-aminopentanoic acid, 4-aminobutanoic acid, β-alanine, or succinic acid;
PEG is polyethene glycol and has a molecular weight of 1-50 kDa;
each R' is independently selected from the group consisting of cholic acid, (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), and (3α, 5β, 7α, 12α)-7,12-dihydroxy-3-(3-amino-2-hydroxy-1-propoxy)-cholic acid (CA-3OH—$NH_2$);
each R" is independently selected from the group consisting of biotin, trans-cinnamic acid, lauric acid, linoleic acid, lipoic acid, nicotinic acid, octanoic acid, oleic acid, retinoic acid, sorbic acid, piromidic acid, caffeic acid, ricinoleic acid, pantothenic acid, aminocaproic acid, riboflavin, pyridoxine, cholecalciferol, and a nonsteroidal anti-inflammatory drug;
each branched monomer unit X is a diaminocarboxylic acid; and
each $Y^1$ is independently a crosslinkable group selected from the group consisting of a thiol, a boronic acid, a 1,2-diol, or a cysteine group.

2. The compound of claim 1, wherein each branched monomer unit X is lysine.

3. The compound of claim 2, wherein
each X is lysine;
PEG is PEG5k;
each R' is Cholic acid; and
each R" is selected from the group consisting of etodolac, indomethacin, naproxen, oxaprozin and sulindac.

4. The compound of claim 1, wherein
each branched monomer unit X is lysine; and
each L' is a linker Ebes or succinic acid.

5. The compound of claim 1, wherein
each L" is independently a bond or a linker Ebes;
PEG has a molecular weight of 1-50 kDa;
each R' is cholic acid;
each R" is selected from the group consisting of cinnamic acid and linoleic acid;
each branched monomer unit X is lysine; and
each $Y^1$ is cysteine.

* * * * *